United States Patent
Hirabayashi

(10) Patent No.: US 9,265,466 B2
(45) Date of Patent: Feb. 23, 2016

(54) X-RAY RADIOGRAPHIC APPARATUS, METHOD OF MEASURING HEAD TILT IN TAKING RADIOGRAPH, STAND FOR X-RAY RADIOGRAPHIC APPARATUS, CHAIR FOR X-RAY RADIOGRAPHIC APPARATUS, AND HEAD TILT SETTING DEVICE

(71) Applicant: CEPHMEDICAL CORPORATION, Nagano (JP)

(72) Inventor: Daiki Hirabayashi, Nagano (JP)

(73) Assignee: Cephmedical Corporation, Nagano (JP)

( * ) Notice: Subject to any disclaimer, the term of this patent is extended or adjusted under 35 U.S.C. 154(b) by 0 days.

(21) Appl. No.: 14/415,804

(22) PCT Filed: Jul. 18, 2013

(86) PCT No.: PCT/JP2013/069464
§ 371 (c)(1),
(2) Date: Jan. 20, 2015

(87) PCT Pub. No.: WO2014/017366
PCT Pub. Date: Jan. 30, 2014

(65) Prior Publication Data
US 2015/0164442 A1 Jun. 18, 2015

(30) Foreign Application Priority Data

Jul. 26, 2012 (JP) ................. 2012-165495
Dec. 17, 2012 (JP) ................. 2012-274275
May 23, 2013 (JP) ................. 2013-108647

(51) Int. Cl.
*A61B 6/14* (2006.01)
*A61B 6/04* (2006.01)
*A61B 6/00* (2006.01)

(52) U.S. Cl.
CPC .............. *A61B 6/0492* (2013.01); *A61B 6/14* (2013.01); *A61B 6/501* (2013.01)

(58) Field of Classification Search
CPC .......... A61B 6/14; A61B 6/04; A61B 6/0478; A61B 6/0492; A61B 6/587; A61B 6/589; A61N 5/1049; A61N 2005/105; A61N 2005/1051; G01N 23/04; G01N 23/083
USPC ............... 378/38, 62, 68, 204, 205, 206, 208
See application file for complete search history.

(56) References Cited

U.S. PATENT DOCUMENTS 5,692,027 A * 11/1997 Yoshimura ............... A61B 6/14
378/116

FOREIGN PATENT DOCUMENTS

| JP | 45-026658 | 9/1970 |
|---|---|---|
| JP | 06-067301 | 3/1994 |

(Continued)

OTHER PUBLICATIONS

Written Opinion of the International Searching Authority issued in connection with International Patent Application No. PCT/JP2013/069464, dated Sep. 10, 2013.

(Continued)

*Primary Examiner* — Jurie Yun
(74) *Attorney, Agent, or Firm* — K&L Gates LLP

(57) ABSTRACT

Provided is an X-ray radiographic apparatus that can take a lateral cephalometric radiograph, a posteroanterior cephalometric radiograph, etc. under the same state of the tilt in the front-rear direction of the head of a subject easily and with high reproducibility, and is free of risks associated with the use of an infraorbital point pointing bar. The X-ray radiographic apparatus includes: a pair of arms provided facing each other with a reference line therebetween; ear rods provided to mutually facing inside surfaces of the pair of arms; a head tilt setting device for setting the tilt in the front-rear direction of the head of the subject provided on one arm, and a horizontal plane verification mechanism provided on the head tilt setting device or outside of the head tilt setting device.

13 Claims, 74 Drawing Sheets

(56) References Cited

FOREIGN PATENT DOCUMENTS

| JP | 2002-125962 | 5/2002 |
|---|---|---|
| JP | 2002-172120 | 6/2002 |
| JP | 2007-299038 | 11/2007 |
| JP | 2009-200612 | 9/2009 |

OTHER PUBLICATIONS

Kimura, Kazuo, "A Study on the Postero-anterior Cephalograms of Human Dry Skulls: Part 3 A Stability of Horizontal Reference Lines", Tohoku University Dental Journal, Dec. 28, 1989, 8(2), pp. 99-106. (8 pages).

Akira Kameda, "Diagnostic Method of Orthodontic Clinic", Isho Shuppan Co., Ltd., Jun. 1978, pp. 54-71. (with abridged translation) (22 pages).

Kunihiko Miyashita, "A Color Atlas Roentgen Anatomy and Cephalometric Analysis", Quintessence Publishing Co., Ltd., Jun. 10, 2009, pp. 146-149. (with abridged translation) (7 pages).

William R. Proffit (translated by Kenji Takada), "New Edition Contemporary Orthodontics of Proffit", Quintessence Publishing Co., Ltd., Jun. 10, 2004. (with abridged translation) (6 pages).

Notification of Reasons for Refusal issued in connection with Japanese Patent Application No. 2012-165495, dated Aug. 28, 2012. (9 pages).

Kazuo Kimura, et al., "A study on the postero-anterior cephalograms of human dry skulls; Part 2 Changes of cephalometric images following upper and lower rotation of head," Dentistry Magazine of Tohoku University, Jun. 30, 1989, 8(1), pp. 51-61. (with abridged translation) (12 pages).

* cited by examiner

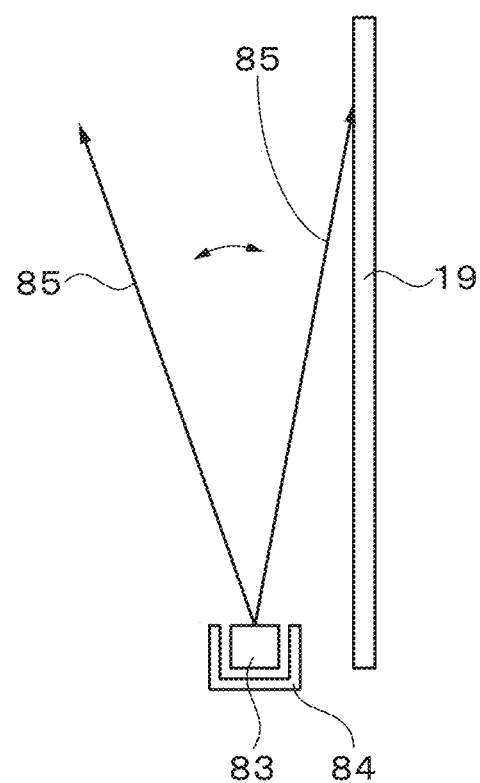

X-RAY RADIOGRAPHIC APPARATUS, METHOD OF MEASURING HEAD TILT IN TAKING RADIOGRAPH, STAND FOR X-RAY RADIOGRAPHIC APPARATUS, CHAIR FOR X-RAY RADIOGRAPHIC APPARATUS, AND HEAD TILT SETTING DEVICE

CROSS REFERENCES TO RELATED APPLICATIONS

The present application is a national stage of International Application No. PCT/JP2013/069464 filed on Jul. 18, 2013, which claims priority to Japanese Patent Application No. 2012-165495 filed on Jul. 26, 2012, Japanese Patent Application No. 2012-274275 filed on Dec. 17, 2012, and Japanese Patent Application No. 2013-108647 filed on May 23, 2013, the disclosure of which is incorporated herein by reference.

BACKGROUND

The present invention relates to an X-ray radiographic apparatus, a method of measuring head tilt in taking a radiograph, a stand for X-ray radiographic apparatus, a chair for X-ray radiographic apparatus and a head tilt setting device which are suitable, for example, for applying in taking a cephalometric radiograph by a cephalometric X-ray radiographic apparatus.

In an orthodontic treatment, etc., when deciding a treatment plan, generally, taking a cephalometric radiograph (cephalogram) of a patient, and based on the cephalometric radiograph, the cephalometric analysis is performed (for example, see Non-Patent Literatures 1 and 2). Conventionally, as a cephalometric radiograph, a lateral (side surface) cephalometric radiograph is solely taken. As necessary, there is a case where a posteroanterior (PA) cephalometric radiograph is taken, but it is quite rare, even more, the fact is that it is hard to say that effective information useful for the treatment can be obtained from the posteroanterior cephalometric radiograph. The main reason is that setting the tilt in the front-rear direction of the head when taking a posteroanterior cephalometric radiograph is quite difficult, and therefore, every time taking a posteroanterior cephalometric radiograph, the head tilt becomes different. When taking a cephalometric radiograph under the different head tilt, the posteroanterior cephalometric radiograph to be obtained gives completely different impression. For this, under the present conditions, in the first place, the posteroanterior cephalometric radiograph is considered not to be reliable materials in judging the head skeleton, etc. of a patient.

Conventionally, a lateral cephalometric radiograph is said to be taken at the position that the Frankfort plane of the head of a patient becomes parallel to the floor surface (see Non-Patent Literatures 1 and 2). Here, the Frankfort plane is a plane connecting an orbitale with a porion. In order to make the Frankfort plane of the head parallel to the floor surface when taking a lateral cephalometric radiograph, it is known that an infraorbital point pointing bar with a needle-like sharp tip is provided in the horizontal plane in a cephalometric X-ray radiographic apparatus so as to face the face of a patient (see Non-Patent Literature 2). And it is also known that a posteroanterior cephalometric radiograph is similarly taken at the position that the Frankfort plane becomes parallel to the floor surface (see Non-Patent Literature 2).

Also, in the text of Proffit with highest standing in the world as a text of orthodontics (see Non-Patent Literature 3), it is indicated that with regard to the cephalometric analysis, "A cephalometric radiograph is to be taken at the natural head position (NFP), from which the physiologically real horizontal plane can be obtained".

PRIOR ART LITERATURE

Non-Patent Literature

[NON-PATENT LITERATURE 1] "Diagnostic Method of Orthodontic Clinic" (Akira Kameda, pp. 54-71, ISHO SHUPPAN CO., Ltd., June, 1978).
[NON-PATENT LITERATURE 2] "A Color Atlas Roentgen Anatomy and Cephalometric Analysis", Kunihiko Miyashita, pp. 146-149 (Quintessence Publishing Co., Ltd., Jun. 10, 2009)
[NON-PATENT LITERATURE 3] "New Edition Contemporary Orthodontics of Proffit", William R. Proffit (translated by Kenji Takada) (Quintessence Publishing Co., Ltd., Jun. 10, 2004)

SUMMARY

Subjects to be Solved by Invention

However, in the Non-Patent Literature 2, it is only described that when taking a posteroanterior cephalometric radiograph, "The image remarkably tends to vary by variation of the head, therefore it is better to take a lateral cephalometric radiograph first, by which a patient learns the body position, then, to take a posteroanterior cephalometric radiograph." (see the literature, p. 147, lines 11-13), and no specific method of making the Frankfort plane of the head of a patient parallel to the floor surface, when taking a posteroanterior cephalometric radiograph is not described. For this, it is considered to be absolutely difficult that a posteroanterior cephalometric radiograph and a lateral cephalometric radiograph are taken under the same head tilt of a patient. Also, the method has a risk which the face, etc. of a patient would contact with the infraorbital point pointing bar.

Also, according to the method of the Non-Patent Literature 3, when taking a lateral cephalometric radiograph, not to mention a posteroanterior cephalometric radiograph, it is inevitable that the head tilt varies every time taking a cephalometric radiograph, and it is considered that taking a posteroanterior cephalometric radiograph and a lateral cephalometric radiograph under the same head tilt of a patient is very difficult.

Further, as far as the inventor of the present invention knows, a method of taking a posteroanterior cephalometric radiograph and a lateral cephalometric radiograph under the same head tilt of a patient easily is not known.

Also, in order to investigate the growth and development of the maxilla and mandible, it is important to take lateral cephalometric radiographs or posteroanterior cephalometric radiographs at different time, and investigate aging by superposing those lateral cephalometric radiographs or posteroanterior cephalometric radiographs. However, as mentioned above, it was very difficult to take a posteroanterior cephalometric radiograph and a lateral cephalometric radiograph under the same head tilt of a patient, and therefore the investigation of aging was practically difficult.

Therefore, a subject to be solved by the present invention is to provide an X-ray radiographic apparatus wherein a lateral cephalometric radiograph, a posteroanterior cephalometric radiograph, an anteroposterior cephalometric radiograph, and a cephalometric radiograph in any direction between the posteroanterior direction and anteroposterior direction, etc.

can be taken under the same tilt in the front-rear direction of the head of a subject easily and with high reproducibility, furthermore there is no risk associated with the use of an infraorbital point pointing bar, and a method of measuring head tilt when taking a radiograph.

Another subject to be solved by the present invention is to provide a stand for X-ray radiographic apparatus, a chair for X-ray radiographic apparatus, and a head tilt setting device wherein a lateral cephalometric radiograph, a posteroanterior cephalometric radiograph, an anteroposterior cephalometric radiograph, a cephalometric radiograph in any direction between the posteroanterior direction and anteroposterior direction, etc. can be taken easily and with high reproducibility under the same tilt in the front-rear direction of the head of a subject, and furthermore, there is no risk associated with the use of an infraorbital point pointing bar.

The above subjects and the other subjects will be apparent from the following description referring to the attached drawings.

Means for Solving the Subjects

In order to solve the above subject, according to the present invention, there is provided an X-ray radiographic apparatus, comprising:
 a pair of arms provided facing each other,
 ear rods respectively provided on inside surfaces facing each other of the pair of arms,
 a head tilt setting device for setting the tilt in the front-rear direction of the head of a subject which is provided at at least one of the pair of arms, having a transparent plate provided vertically to the central axis of the ear rods integrally with the arm, or provided vertically to the central axis of the ear rods on the exterior surface of the arm; and
 a horizontal plane verification mechanism.

The pair of arms is typically provided facing each other with a reference line therebetween, and is constituted to be able to rotate around the reference line. The head tilt setting device typically sets the head tilt of a subject under the state inserting the ear rods of the pair of arms in the external acoustic openings of both ears of the subject. The head tilt setting device typically sets the head tilt so that when looking at the head from the lateral side (side surface), a straight line connecting the first reference point on the arms or the ear rods with the second reference point of the face of the subject becomes the horizontal line, or a straight line tilted at a predetermined angle to the horizontal line. The head tilt setting device has preferably the function of a protractor for measuring the inclination angle to the horizontal line centered on the first reference point. By using the function of a protractor, the tilt in the front-rear direction of the head can be set accurately. The inclination angle to the horizontal line centered on the first reference point may be a positive angle (when the straight line connecting the first reference point with the second reference point tilts upward to the horizontal line), or a negative angle (when the straight line connecting the first reference point with the second reference point tilts downward to the horizontal line).

The horizontal plane verification mechanism can be used for an inspector to recognize the horizontal plane when setting the head tilt using the head tilt setting device. The horizontal plane verification mechanism may be provided to the transparent plate or may be provided outside of the transparent plate. When providing the horizontal plane verification mechanism to the transparent plate, as the horizontal plane verification mechanism, for example, a horizontal plate provided on the transparent plate protruding inside vertically to the transparent plate is used, and further, a colored horizontal line provided at the position of both sides of the transparent plate facing each other can be used. The horizontal plate may be a simple plate, and further, for example, the one having a foldable scale-like constitution which is able to open and close in the horizontal plane. Further, the horizontal plane verification mechanism may be, for example, an optical device (including a light source and a scanning mechanism) which is able to irradiate a visible light beam or scan it in the horizontal plane, or a horizontal colored line. The visible light beam is a laser beam or a beam-like light which is made from the light emitted from a light-emitting diode. The colored line is, for example, a thin linear wire made of metal, carbon fiber, plastics, etc. of which surface is colored, or a linear transparent fiber colored by making a visible light such as a red light or a green light, etc. wave guide from the end face. Further, the colored line may be the visible light beam itself. When providing the horizontal plane verification mechanism outside of the transparent plate, as the horizontal plane verification mechanism, for example, a horizontal plate which is able to move up and down or move in the horizontal plane, and further, the various kinds mentioned as examples of the horizontal plane verification mechanism when providing the horizontal plane verification mechanism to the transparent plate can be used. On the transparent plate constituting the head tilt setting device, as necessary, a scale showing a length made of X-ray shielding materials is provided. Preferably, the transparent plate is provided on one of the pair of arms, and another transparent plate provided with a scale showing a length made of X-ray shielding materials is provided on the other arm of the pair of arms. These scales can serve as a reference of the length in radiographs or images obtained by cephalometric radiography.

In order to make the straight line connecting the first reference point with the second reference point become the Frankfort plane of the head or a plane near to it, the first reference point is selected to be, for example, the uppermost point of the ear rods (which coincides with the porions of both ears of a subject at the time of taking a radiograph), and the second reference point is selected to be, for example, the orbitale, the orbital margin just under the center of the pupil, or the center of the palpebral fissure, etc. In case the straight line connecting the first reference point with the second reference point does not need to be the Frankfort plane or a plane near to it, the first reference point and the second reference point can be selected arbitrarily.

The X-ray radiographic apparatus is, for example, a cephalometric X-ray radiographic apparatus, but may be the other X-ray radiographic apparatus for medical and dental use, or may be a computed tomography (CT) apparatus, etc. The region to be taken a radiograph of a subject is typically a head, but may include the cervical region in addition to the head or may be only the cervical region.

Further, according to the present invention, there is also provided a method of measuring head tilt in taking a radiograph, comprising:
 when taking a radiograph of the head of a subject, measuring the tilt in the front-rear direction of the head of a subject under the state that the ear rods respectively provided on inside surfaces facing each other of a pair of arms provided to mutually facing each other are inserted in the external acoustic openings of both ears of the subject, using a head tilt setting device provided at at least one of the pair of arms for setting a straight line connecting the first reference point on the arm or the ear rods with the second reference point of the face of the subject becomes the horizontal line or a straight line tilted at a predetermined angle to the horizontal line when looking at the head from the lateral direction, having a transparent plate provided vertically to the central axis of the ear rods integrally with the arm, or provided vertically to the central axis of the ear rods on the exterior surface of the arm; and a horizontal plane verification mechanism.

In the present invention of a method of measuring head tilt in taking a radiograph, unless otherwise violating the character, the explanation concerning the invention of the X-ray radiographic apparatus comes into effect.

Further, according to the present invention, there is also provided a stand for X-ray radiographic apparatus used when taking a radiograph of the head of a subject by an X-ray radiographic apparatus having a pair of arms provided facing each other and ear rods respectively provided on inside surfaces facing each other of the pair of arms, comprising:

a head tilt setting device for setting the tilt in the front-rear direction of the head of the subject under the state that the ear rods of the pair of arms are inserted in the external acoustic openings of both ears of the subject so that a straight line connecting the first reference point on the arm or the ear rods with the second reference point of the face of the subject becomes the horizontal line or a straight line tilted at a predetermined angle to the horizontal line when looking at the head from the lateral direction, having a transparent plate provided vertically to the central axis of the ear rods integrally with the arm, or provided vertically to the central axis of the ear rods on the exterior surface of the arm; and a horizontal plane verification mechanism.

Here, the stand for X-ray radiographic apparatus is typically set so that the head tilt setting device comes to the same position as the head tilt setting device in the X-ray radiographic apparatus at the time of taking a radiograph.

Further, according to the present invention, there is also provided a chair for X-ray radiographic apparatus used when taking a radiograph of the head of a subject by an X-ray radiographic apparatus having a pair of arms provided facing each other and ear rods respectively provided on inside surfaces facing each other of the pair of arms, comprising:

a head tilt setting device for setting the tilt in the front-rear direction of the head of the subject under the state that the ear rods of the pair of arms are inserted in the external acoustic openings of both ears of the subject so that a straight line connecting the first reference point on the arm or the ear rods with the second reference point of the face of the subject becomes the horizontal line or a straight line tilted at a predetermined angle to the horizontal line when looking at the head from the lateral direction, having a transparent plate provided vertically to the central axis of the ear rods integrally with the arm, or provided vertically to the central axis of the ear rods on the exterior surface of the arm; and a horizontal plane verification mechanism.

Here, the head tilt setting device of the chair for X-ray radiographic apparatus is typically set at the same position as the head tilt setting device in the X-ray radiographic apparatus at the time of taking a radiograph.

Further, according to the present invention, there is also provided a head tilt setting device to be provided at at least one of a pair of arms of an X-ray radiographic apparatus having the pair of arms provided facing each other, and ear rods respectively provided on inside surfaces facing each other of the pair of arms, used, when taking a radiograph of the head of a subject, to set the tilt in the front-rear direction of the head of the subject under the state that the ear rods of the pair of arms are inserted in the external acoustic openings of both ears of the subject so that a straight line connecting the first reference point on the arm or the ear rods with the second reference point of the face of the subject becomes the horizontal line or a straight line tilted at a predetermined angle to the horizontal line when looking at the head from the lateral direction, comprising:

a transparent plate provided vertically to the central axis of the ear rods on the exterior surface of the arm, the transparent plate having a horizontal plane verification mechanism, the head tilt setting device having the function of a protractor for measuring the inclination angle to the horizontal line centered on the first reference point.

In the present invention of the stand for X-ray radiographic apparatus, the chair for X-ray radiographic apparatus, and the head tilt setting device, regarding other than those of mentioned above, the explanation concerning the invention of the X-ray radiographic apparatus comes into effect unless it is contrary to its character.

Effect of the Invention

According to the present invention, a lateral cephalometric radiograph, a posteroanterior cephalometric radiograph, an anteroposterior cephalometric radiograph, and a cephalometric radiograph in any direction between the posteroanterior direction and the anteroposterior direction, etc. can be taken under the same tilt in the front-rear direction of the head of a subject easily and with high reproducibility, moreover there is no risk associated with the use of an infraorbital point pointing bar.

Additional features and advantages are described herein, and will be apparent from the following Detailed Description and the figures.

BRIEF DESCRIPTION OF THE FIGURES

FIG. 57 A plan view showing an optical device to be used as a horizontal plane verification mechanism in a cephalometric X-ray radiographic apparatus according to the eighth embodiment of the present invention.

DETAILED DESCRIPTION

Modes for carrying out the invention (hereafter referred as "embodiments") will now be explained below.

1. The First Embodiment

Figure 1:
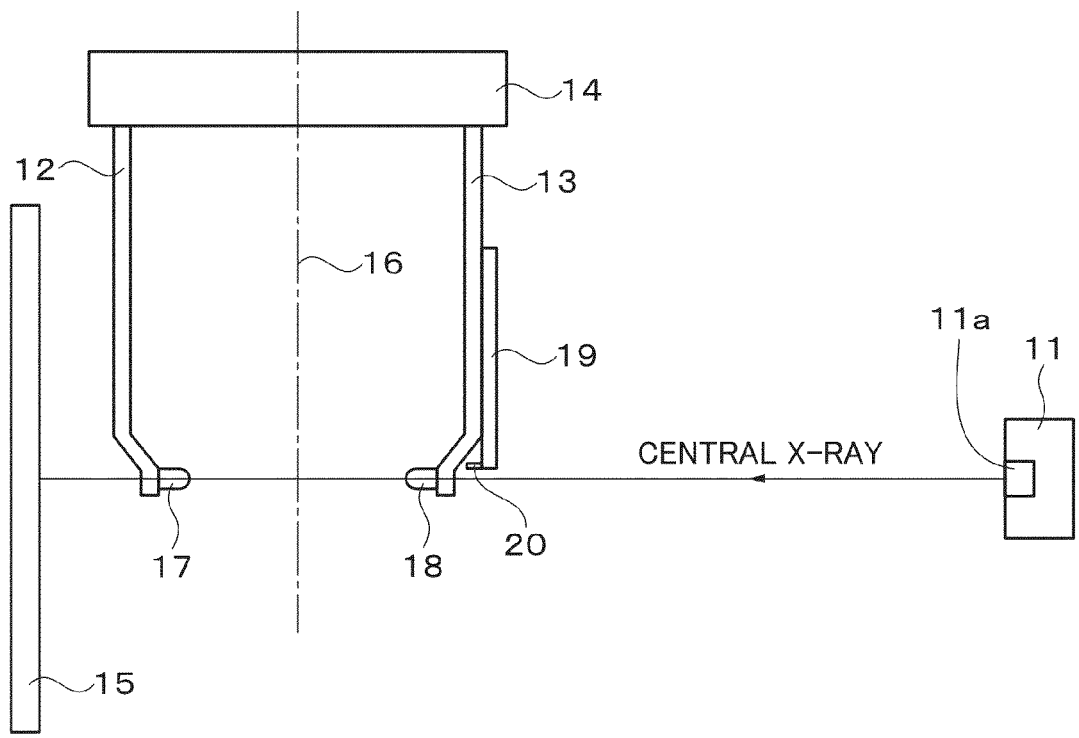
FIG. 1 A schematic drawing looking at a cephalometric X-ray radiographic apparatus according to the first embodiment of the present invention from the horizontal direction and the vertical direction to the central X-ray.

FIG. 1 shows the cephalometric X-ray radiographic apparatus according to the first embodiment. As shown in FIG. 1, the cephalometric X-ray radiographic apparatus has an X-ray generator 11, arms 12 and 13, an arm control device 14, and an X-ray detector 15. The X-ray generator 11 has an X-ray tube 11a, and from the X-ray tube 11a, the X-ray is generated. The arm control device 14 is supported for the floor surface by a support part of which drawing is omitted.

The X-ray generated from the X-ray tube 11a is irradiated to the head of a subject, the X-ray transmitted through the head enters into the X-ray detector 15, and the transmission X-ray image is obtained. The X-ray detector 15 is not specifically limited, but, for example, an X-ray film, an imaging plate, a semiconductor detector, etc. are used. The transmission X-ray image is, as necessary, converted to a digital image signal, for example.

The arms 12 and 13 are provided facing each other with a reference line 16 parallel to the vertical line and perpendicular to the central X-ray therebetween. The upper parts of the arms 12 and 13 are fixed to an arm control device 14. And by the arm control device 14, the arms 12 and 13 are able to rotate around the reference line 16, move up and down in a parallel direction to the reference line 16, and move translatory in an opposite direction each other in the horizontal direction. The width of the lower parts of the arms 12 and 13 becomes gradually narrowing towards the bottom edge, and the bottom edge becomes a circular shape (see FIG. 2). Also, the bottom edges of the arms 12 and 13, after folded back at a predetermined angle inward to the vertical line respectively, again becomes parallel to the vertical line. However, the arms 12 and 13 may be parallel to the vertical line on the whole. At least the parts of the arms 12 and 13 irradiated by the X-ray at the time of taking a radiograph are constituted of transparent materials. Generally, almost all the parts of the arms 12 and 13 are constituted of the transparent materials. The inside surfaces facing each other of the bottom edges of the arms 12 and 13 are respectively provided concentrically with column-shaped ear rods 17 and 18 with pointed tips. As the ear rods 17 and 18, publicly known ear rods can be used. The outlines of the ear rods 17 and 18 come out at the time of taking a radiograph.

At least on one of the exterior surfaces of the arms 12 and 13, a head tilt setting device 19 for setting the tilt in the front-rear direction of the head of a subject is fixed. In FIG. 1, an example that the head tilt setting device 19 is fixed to the exterior surface of the arm 13 is shown. In this case, the head tilt setting device 19 is constituted of a rectangular transparent plate vertically to the central axis of the ear rod 18. As the transparent plate, a transparent plastic plate such as an acrylic plate, a PET (polyethylene terephthalate) plate, etc. or a glass plate, etc. can be used. The transparent plate may be that a necessary mechanical strength can be obtained, and is thick enough not to fold easily. Thickness of the transparent plate may be, for example, 2 mm or more and 10 mm or less. The method of fixing the head tilt setting device 19 is not specifically limited, but may be adhesion, clip-on, screwed down, etc.

Figure 2:
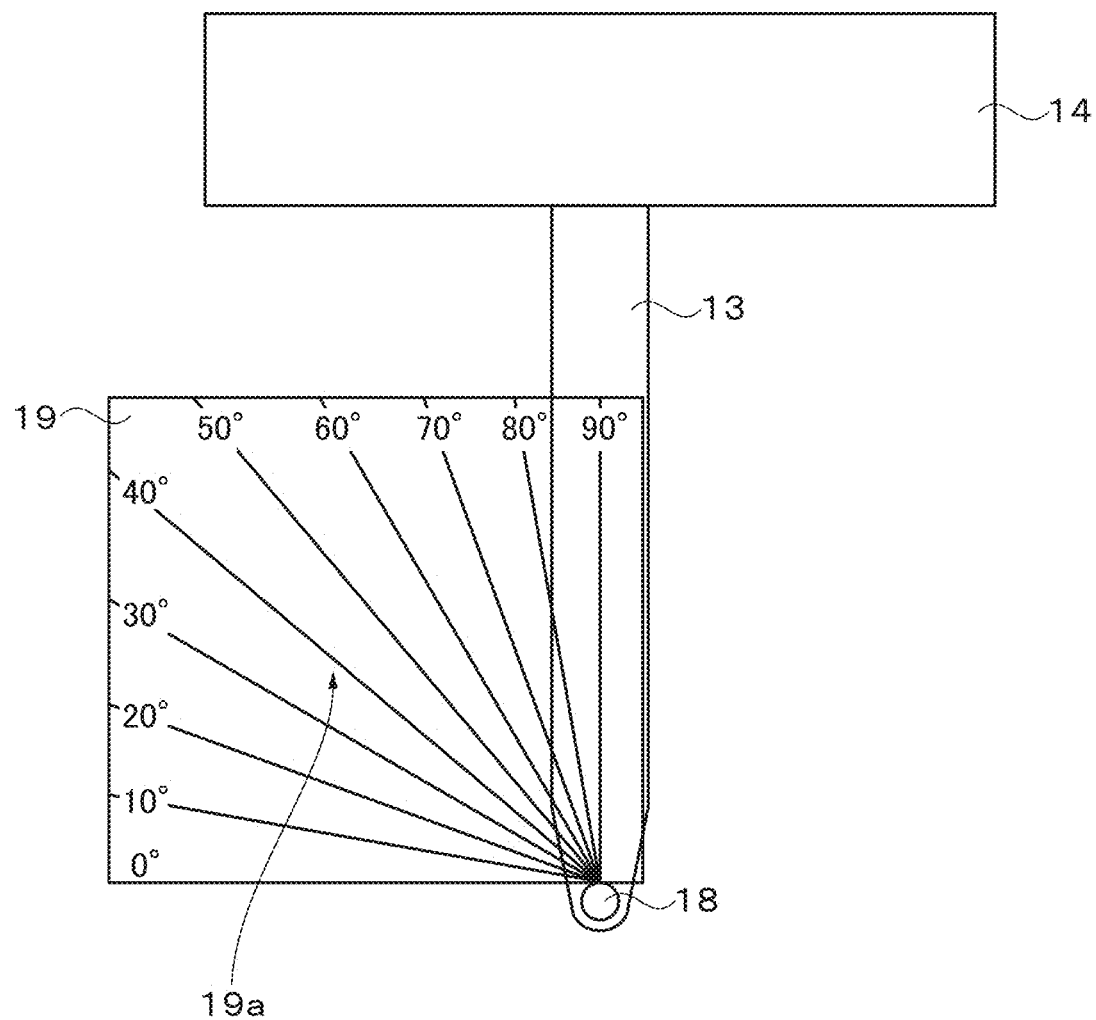
FIG. 2 A schematic drawing showing an arm of the cephalometric X-ray radiographic apparatus according to the first embodiment of the present invention, and a head tilt setting device provided on the arm.
Figure 3:
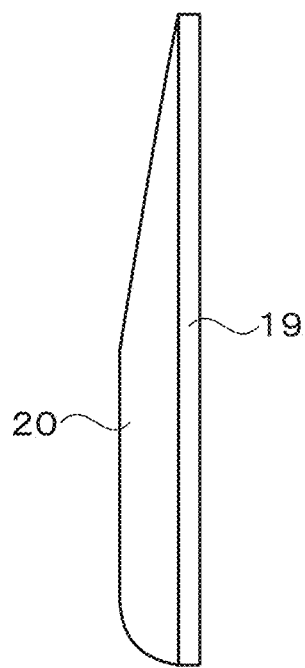
FIG. 3 A plan view showing a horizontal plate provided at the bottom edge of the head tilt setting device of the cephalometric X-ray radiographic apparatus according to the first embodiment of the present invention.

The details of the head tilt setting device 19 are shown in FIG. 2. FIG. 2 is a drawing looking at the head tilt setting device 19 from the vertical direction to the surface. As shown in FIG. 2, the bottom edge surface (the base) of the head tilt setting device 19 is parallel to the horizontal plane. The bottom edge surface of the head tilt setting device 19 coincides with the tangential direction drawn to the vertical direction to the central axis of the ear rod 18 at the uppermost point of the ear rod 18. At the head tilt setting device 19, an angle scale 19a centered on the uppermost point of the ear rod 18 is formed, and has the function of a protractor. In FIG. 2, the angle scale 19a is formed from 0° to 90° marked every 10°, but a method of marking the angle scale 19a is not limited to this. For example, the angle scale 19a may be formed, marked every 5° or 1°. Or the angle scale 19a may be formed only within a specific angle range, for example, from 0° to 30°. The line at a 0° of the angle scale 19a coincides with the bottom edge surface of the head tilt setting device 19. The angle scale 19a is typically formed with a black colored line as the same as a general protractor, for example, but is not limited to this. The angle scale 19a except for the 0° may be provided on one surface of the head tilt setting device 19 and is preferably provided respectively on the corresponding position each other to both surfaces. Like this, by providing the angle scale 19a at the corresponding position each other to the both surfaces of the head tilt setting device 19, when looking at the angle scale 19a from the horizontal direction, the direction that the angle scales 19a of the both surfaces coincide is the horizontal direction, and in case not coinciding, it can be judged to go off from the horizontal direction. As shown in FIG. 3, at the bottom edge surface of the head tilt setting device 19, a horizontal plate 20 protruding inward vertically to the head tilt setting device 19 is provided. FIG. 3 shows a plan view of the head tilt setting device 19 and the horizontal plate 20. As shown in FIG. 3, the horizontal plate 20 has a wide part at the part distant from the ear rod 18. In order to make the visual confirmation easy when confirming the horizontal plane, the horizontal plate 20 is preferably colored, specifically, for example, is colored in black. Materials, thickness, width in the horizontal direction, etc. of the horizontal plate 20 are selected, preferably so as to come out to the X-ray transmission images. The materials of the horizontal plate 20 are, for example, transparent plastics such as acryl, etc., opaque plastics, metal, etc. The thickness of the horizontal plate 20 is, for example, 0.2 mm or more and 2 mm or less, but is not limited to this. The width in the horizontal direction of the horizontal plate 20 is, for example, 1 mm or more and 30 mm or less, but not limited to this.

Next, a method of taking a cephalometric radiograph of a subject using the cephalometric X-ray radiographic apparatus will be explained.

(1) A Method of Taking a Lateral Cephalometric Radiograph

Figure 4:
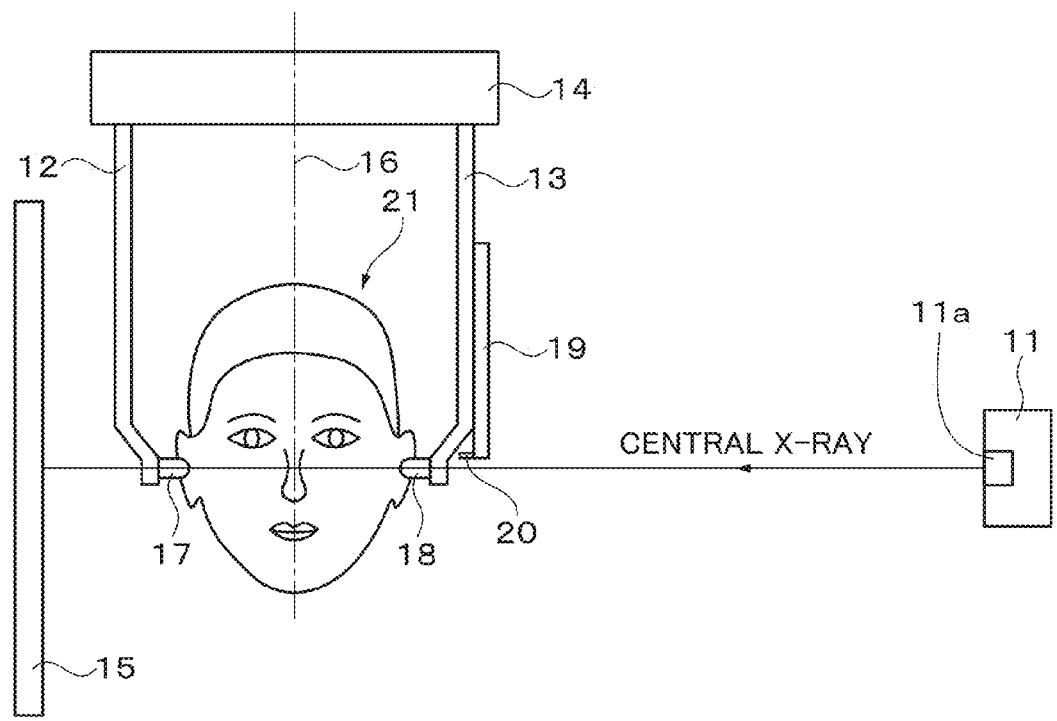
FIG. 4 A schematic drawing for explaining a method of taking a lateral cephalometric radiograph using the cephalometric X-ray radiographic apparatus according to the first embodiment of the present invention.
Figure 5:
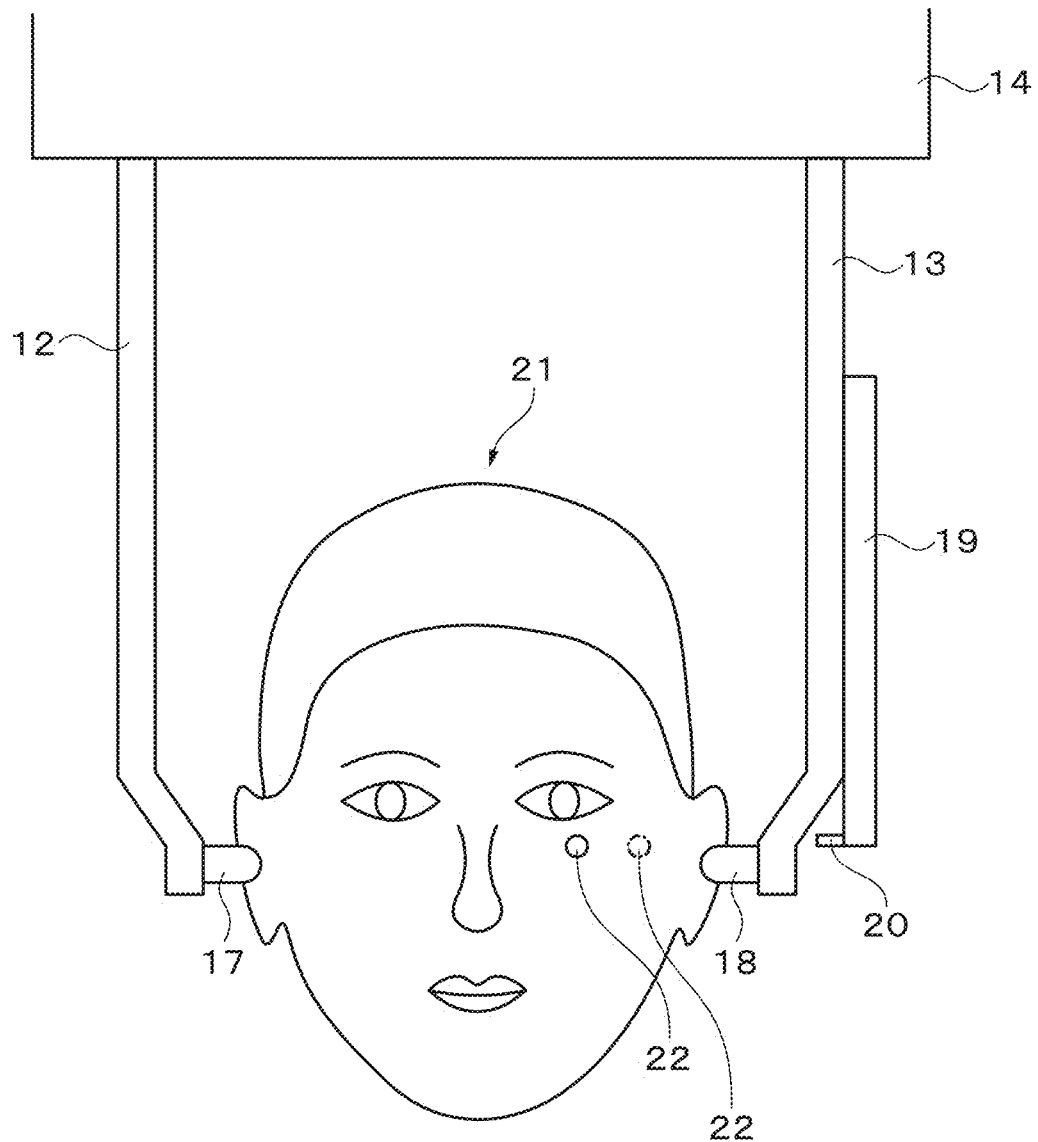
FIG. 5 A schematic drawing for explaining a method of taking a lateral cephalometric radiograph using the cephalometric X-ray radiographic apparatus according to the first embodiment of the present invention.
Figure 6:
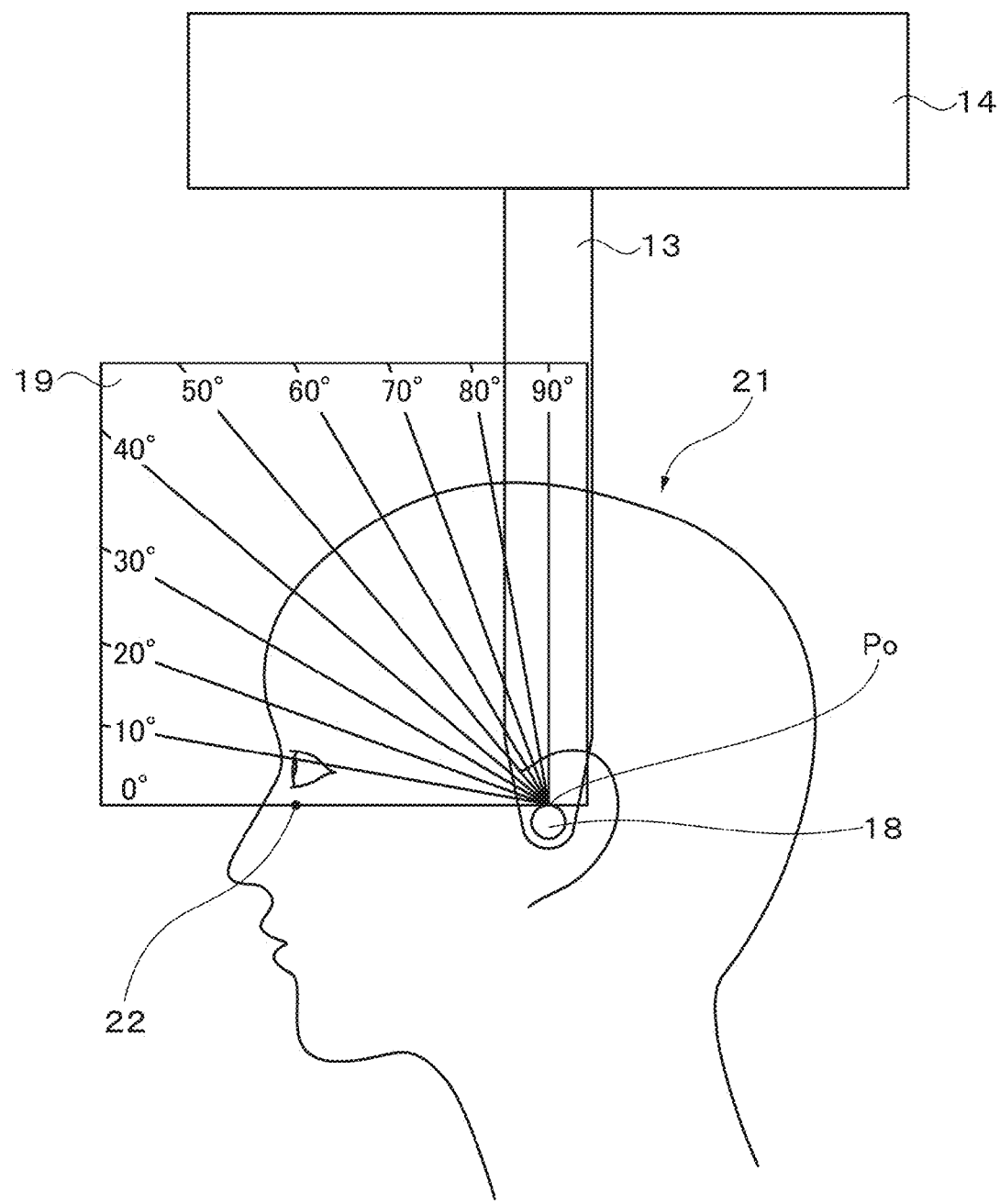
FIG. 6 A schematic drawing for explaining a method of taking a lateral cephalometric radiograph using the cephalometric X-ray radiographic apparatus according to the first embodiment of the present invention.

In FIG. 1, the arms 12 and 13 are made to move translatory to the outside in the horizontal direction, well away from each other, and to move to a high enough position. Under the state, as shown in FIG. 4, the head 21 of a subject is positioned between the arms 12 and 13 so that its median sagittal plane becomes vertical to the central X-ray from the X-ray tube 11a. The subject may be in a sitting position, sitting on a chair or in a standing position, standing up. Next, by descending the arms 12 and 13, the ear rods 17 and 18 are made to come to the position of the height of the right and left external acoustic openings of the head 21 of the subject. Next, the arms 12 and 13 are made to move translatory inward in the horizontal direction, and the ear rods 17 and 18 are inserted in the right and left external acoustic openings of the head 21 of the subject. And by making the uppermost points of the ear rods 17 and 18 contact with the porions, the head 21 is fixed so that the irradiation direction of the central X-ray coincides with the central axis of the ear rods 17 and 18. Next, an inspector searches for a predetermined reference point (the second reference point) of the face of the head 21, for example, the orbitale (Or), the orbital margin just under the center of the pupil, the center of the palpebral fissure, etc. For example, when making the orbitale as a reference point, the inspector can search by touching the vicinity of the infraorbital margin with a fingertip. And as shown in FIG. 5, a circular small colored seal 22 is put on the reference point that is searched for like this. The color of the seal 22 may be basically any color, but, for example, may be red, yellow, green, blue, white, black, etc. In case that it is difficult to look the seal 22 put on the reference point from the lateral direction of the head 21, another seal 22 is also put on the outside of the horizontal direction from the seal 22 on the face, for example, at the position apart from 5 to 20 mm. Next, as shown in FIG. 6, the inspector looks at the head tilt setting device 19 in the horizontal direction from the outside. At this time, the seal 22 can be seen through the head tilt setting device 19 made of the transparent plate. And, using the angle scale 19a of the head tilt setting device 19, a straight line connecting the porion (that coincides with the uppermost point of the ear rod 18) with the orbitale is set at an intended angle. In FIG. 6, as an example, a case where a plane connecting the porion with the orbitale, that is, the Frankfort plane is set horizontally. In case the Frankfort plane is set horizontally like this, the horizontal plate 20 that coincides with a 0° of the angle scale 19a is observed from the outside. In case the horizontal plate 20 is seen like a line, the observation is made from the horizontal direction, and the tilt in the front-rear direction of the head 21 is set so that a straight line connecting the porion with the orbitale coincides with the horizontal plate 20. Thus, the Frankfort plane of the head 21 is set to parallel to the horizontal plane (floor surface).

By taking a radiograph under the state that the tilt of the head 21 is set at an intended tilt as mentioned above, a lateral cephalometric radiograph is taken.

Figure 7:
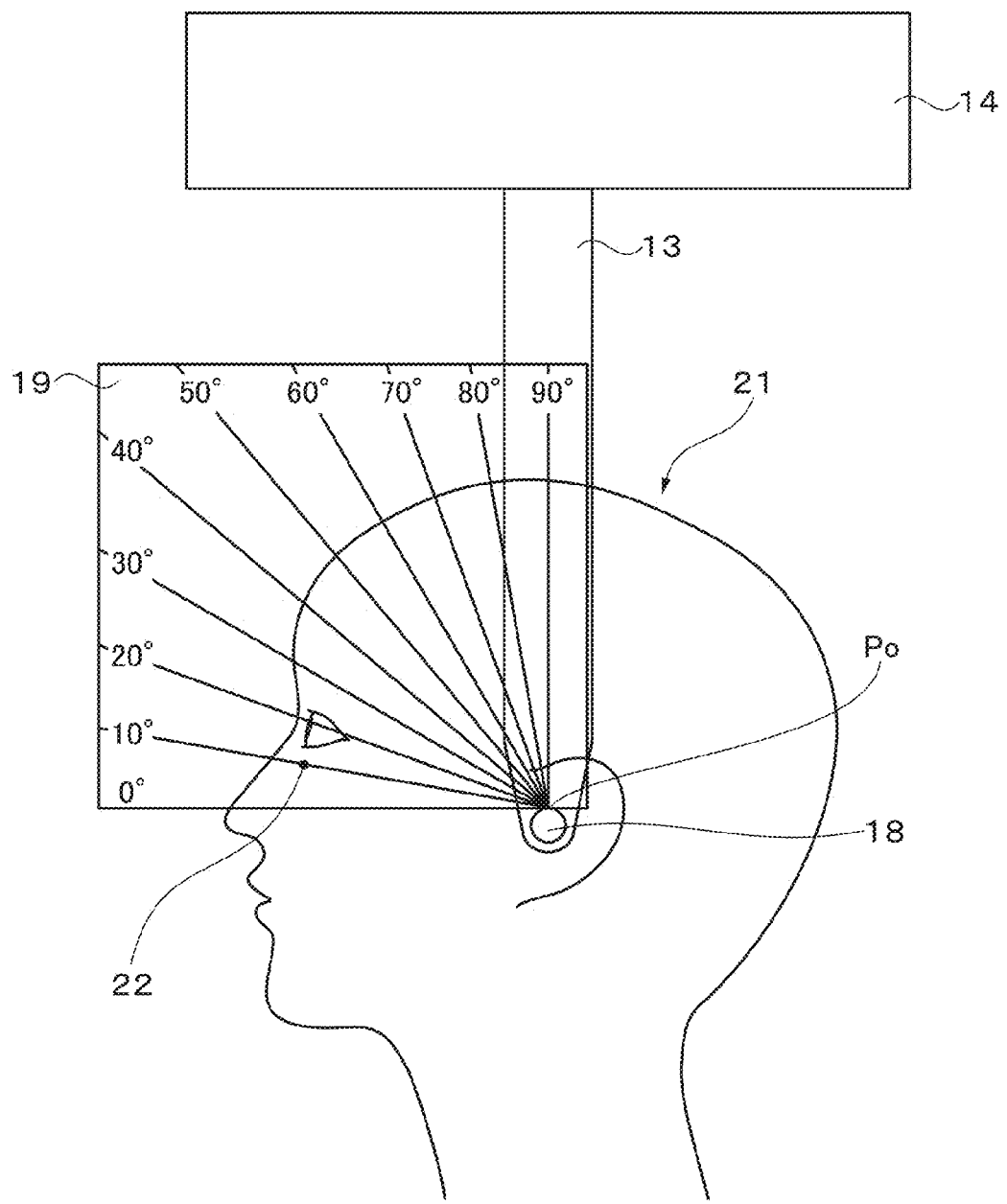
FIG. 7 A schematic drawing for explaining a method of taking a lateral cephalometric radiograph, facing the face upward and tilting the head at a 10° in the front-rear direction using the cephalometric X-ray radiographic apparatus according to the first embodiment of the present invention.

As an example of taking a lateral cephalometric radiograph at the position that the Frankfort plane of the head 21 is tilted at positive or negative angle to the horizontal plane, a case of taking a lateral cephalometric radiograph under the state that the Frankfort plane of the head 21 is tilted at a 10° (the face faces upward) to the horizontal plane is shown in FIG. 7. As shown in FIG. 7, in this case, using the angle scale 19a of the head tilt setting device 19, adjusting the tilt in the front-rear direction of the head 21, the straight line connecting the porion with the orbitale is set at an angle of 10°.

(2) A Method of Taking a Posteroanterior Cephalometric Radiograph

Figure 8:
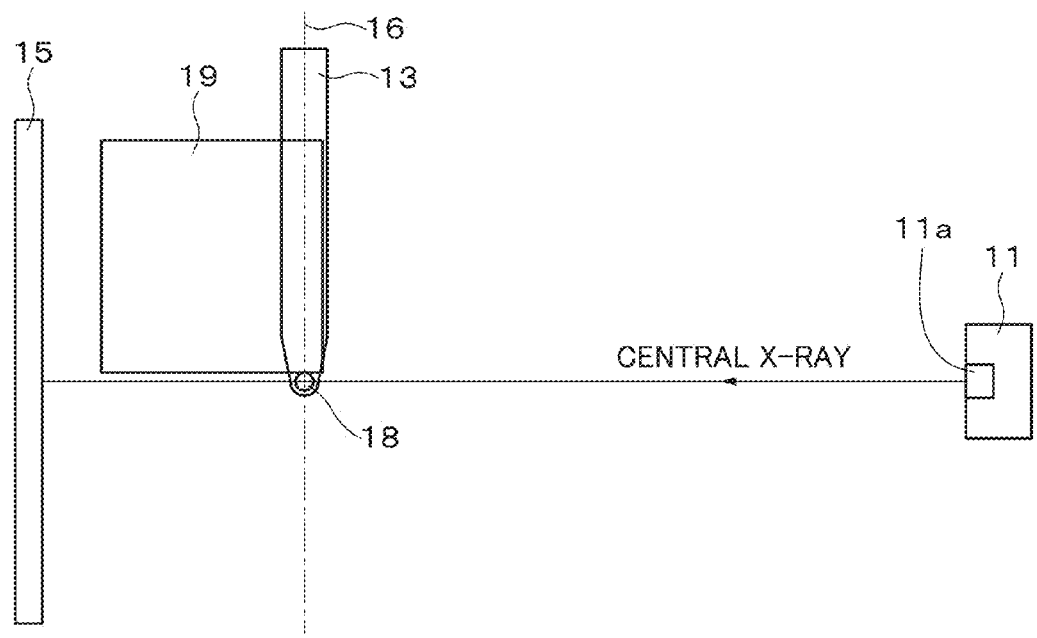
FIG. 8 A schematic drawing for explaining a method of taking a posteroanterior cephalometric radiograph using the cephalometric X-ray radiographic apparatus according to the first embodiment of the present invention.
Figure 9:
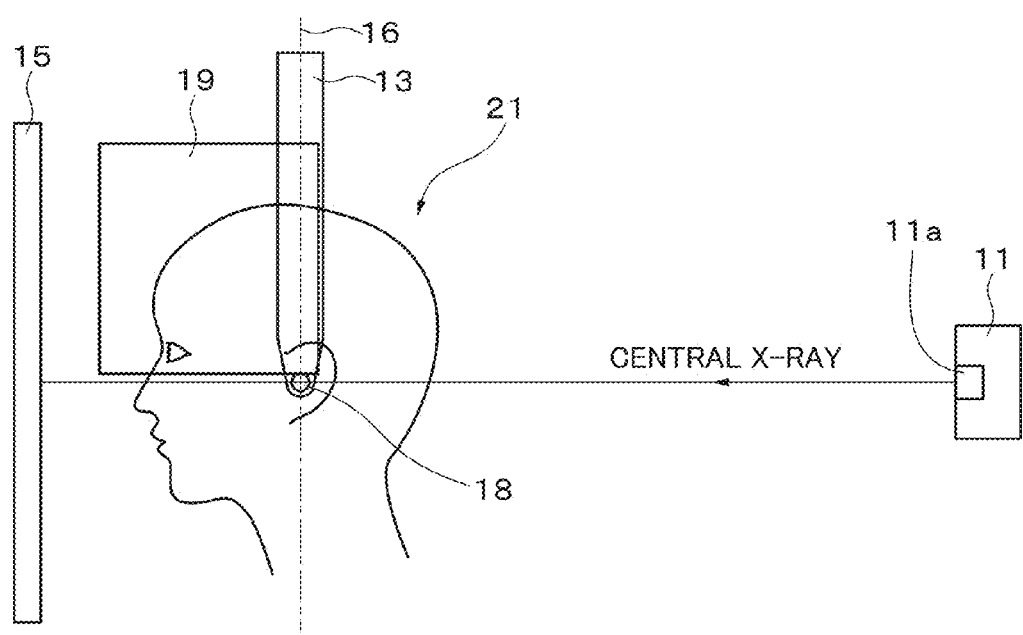
FIG. 9 A schematic drawing for explaining a method of taking a posteroanterior cephalometric radiograph using the cephalometric X-ray radiographic apparatus according to the first embodiment of the present invention.

As shown in FIG. 8, the arms 12 and 13 are rotated 90° around the reference line 16 from the position shown in FIG. 1. And as shown in FIG. 9, as the same as the case of taking a lateral cephalometric radiograph, inserting the ear rods 17 and 18 in the right and left external acoustic openings of the head 21 of a subject, and by contacting the uppermost point of the ear rods 17 and 18 with the porion, the head 21 is fixed. In this case, the face of the head 21 faces the X-ray detector 15. Also, the irradiation direction of the central X-ray intersects at right angles with the central axis of the ear rods 17 and 18. On the predetermined reference point of the face of the head 21, specifically, for example, on the orbitale, the seal 22 is kept putting. Next, the inspector looks at the head tilt setting device 19 from the outside in the horizontal direction. At this time, the seal 22 can be seen through the head tilt setting device 19. And, as the same as the case of taking a lateral cephalometric radiograph, using the angle scale 19a of the head tilt setting device 19, the straight line connecting the porion with the orbitale is set at the same angle as in the case of taking the lateral cephalometric radiograph. And, by taking a radiograph at the position, the posteroanterior cephalometric radiograph can be taken under the state that the tilt in the front-rear direction of the head 21 is the same as when taking the lateral cephalometric radiograph. For example, a lateral cephalometric radiograph and also a posteroanterior cephalometric radiograph can be taken at the position that the Frankfort plane of the head 21 becomes parallel to the horizontal plane (floor surface).

(3) A Method of Taking an Anteroposterior Cephalometric Radiograph

A method of taking an anteroposterior cephalometric radiograph is the same as the method of taking a posteroanterior cephalometric radiograph, except that the head 21 is positioned so that the face of the head 21 faces to the X-ray generator 11.

Figure 10:
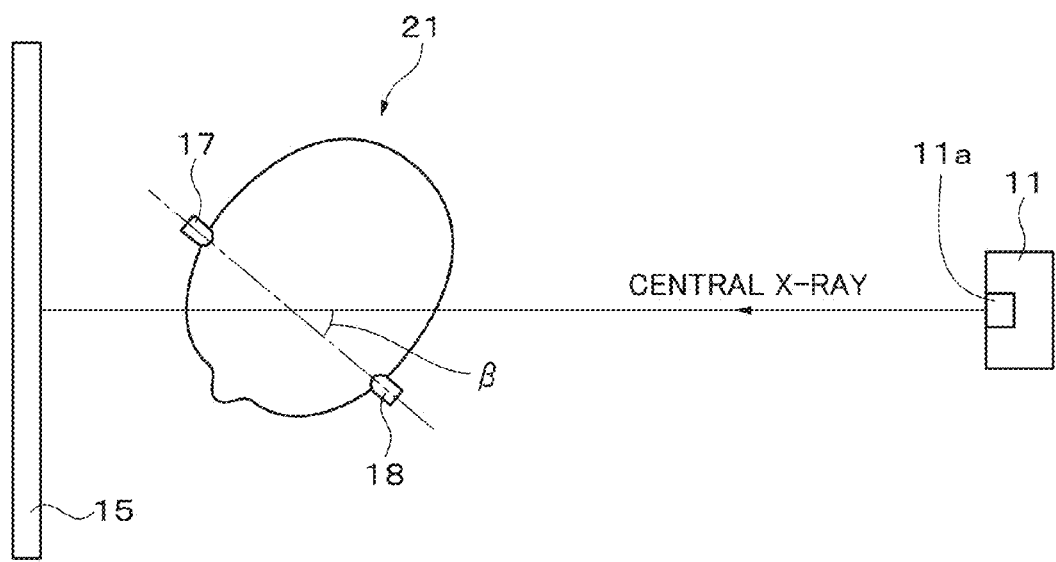
FIG. 10 A schematic drawing for explaining a method of taking a cephalometric radiograph in any direction between the posteroanterior direction and anteroposterior direction using the cephalometric X-ray radiographic apparatus according to the first embodiment of the present invention.

(4) A Method of Taking a Cephalometric Radiograph from any Direction Between the Posteroanterior Direction and the Anteroposterior Direction The arms 12 and 13 are rotated by an angle β (0°<β<360°) around the reference line 16 from the position shown in FIG. 1. The plan view of the cephalometric X-ray radiographic apparatus and the head in this state is shown in FIG. 10. And, as the same as the case of taking a lateral cephalometric radiograph, inserting the ear rods 17 and 18 in the right and left external acoustic openings of the head 21 of a subject, by making the uppermost point of the ear rods 17 and 18 contact with the porion, the head 21 is fixed. In this case, the irradiation direction of the central X-ray is tilted at an angle β to the central axis of the ear rods 17 and 18. On the predetermined reference point of the face of the head 21, specifically, for example, on the orbitale, the seal 22 is kept putting. Next, the inspector looks at the head tilt setting device 19 from the outside in the horizontal direction. At this time, the seal 22 can be seen through the head tilt setting device 19. And, as the same as the case of taking a lateral cephalometric radiograph, using the angle scale 19a of the head tilt setting device 19, the straight line connecting the porion with the orbitale is set at the same angle as the case of taking a lateral cephalometric radiograph. And by taking a radiograph at this position, a cephalometric radiograph can be taken under the state that the tilt in the front-rear direction of the head 21 is the same as the case of taking a lateral cephalometric radiograph. For example, the radiograph can be taken at the position that the Frankfort plane of the head 21 becomes parallel to the horizontal plane (floor surface) as the same as a lateral cephalometric radiograph and a posteroanterior cephalometric radiograph.

By the cephalometric X-ray radiographic apparatus according to the first embodiment, the following various advantages can be obtained. That is, using the head tilt setting device 19, the tilt in the front-rear direction of the head 21 at the time of taking a radiograph can be set at the intended tilt. By this, a lateral cephalometric radiograph, a posteroanterior cephalometric radiograph, an anteroposterior cephalometric radiograph, a cephalometric radiograph in any direction between the posteroanterior direction and anteroposterior direction, etc. can be taken easily and with high reproducibility under the same state of the tilt in the front-rear direction of the head 21 of a subject. For this, for example, when taking a lateral cephalometric radiograph or a posteroanterior cephalometric radiograph at different time, for example, when taking a radiograph one year after from a certain time taking a radiograph, a radiograph can be taken under the same state of the tilt in the front-rear direction of the head 21. Like this, because of being able to take a radiograph any time under the same tilt in the front-rear direction of the head 21, the superposition of a lateral cephalometric radiograph or an anteroposterior cephalometric radiograph can be made easily. By this, the aging of the maxilla and mandible of the head 21 can be investigated correctly, and the growth and development of the maxilla and mandible can be investigated correctly. In addition, in the first embodiment, as the infraorbital point pointing bar is not used, there is no risk with regards to the use of the infraorbital point pointing bar.

2. The Second Embodiment

In the cephalometric X-ray radiographic apparatus according to the second embodiment, unlike the cephalometric X-ray radiographic apparatus according to the first embodiment, the head tilt setting device 19 is not provided to the arm 13, but the head tilt setting device 19 is provided to a stand for X-ray radiographic apparatus attached to the cephalometric X-ray radiographic apparatus.

Figure 11:
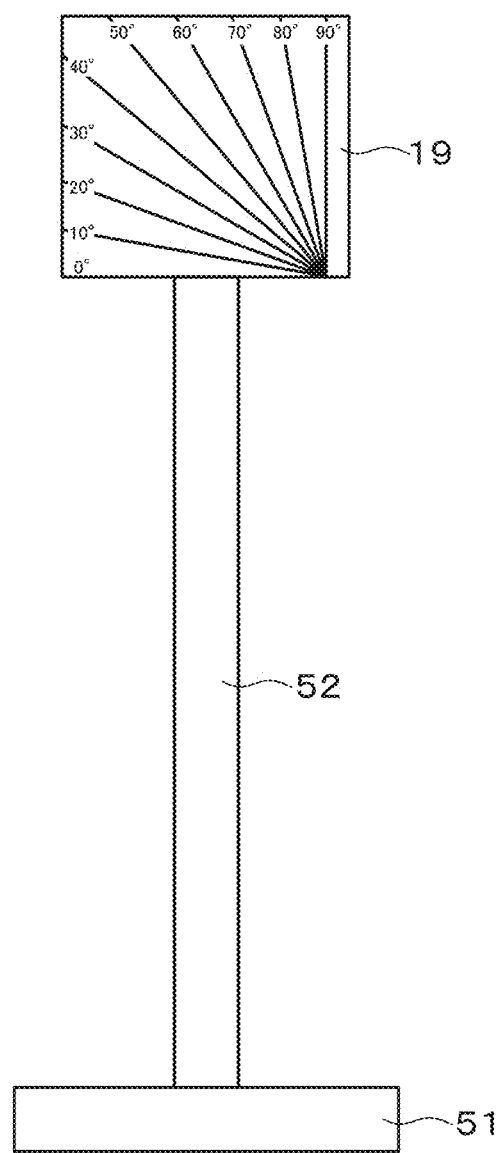
FIG. 11 A front view showing a stand for X-ray radiographic apparatus to be used in a cephalometric X-ray radiographic apparatus according to the second embodiment of the present invention.

FIG. 11 shows the stand for X-ray radiographic apparatus. As shown in FIG. 11, the stand for X-ray radiographic apparatus has a support platform 51 to be placed on the floor surface, a support bar 52 being stood vertically to the support platform 51, and the head tilt setting device 19 fixed to the upper edge of the support bar 52. The support bar 52 is constituted telescopically, and its length can be adjusted within a predetermined range. For this, by adjusting the length of the support bar 52, the height of the head tilt setting device 19 can be adjusted, and by this, the positional relation between the head tilt setting device 19 and the head 21 can be set as the same as the first embodiment. With regards to the head tilt setting device 19, it is the same as the first embodiment.

Next, a method of taking a cephalometric radiograph of a subject using the cephalometric X-ray radiographic apparatus will be explained.

(1) A Method of Taking a Lateral Cephalometric Radiograph

In the cephalometric X-ray radiographic apparatus shown in FIG. 1 which is not provided with the head tilt setting device 19 to the arm 12, the arms 12 and 13 are made to move translatory towards the outside in the horizontal direction, set apart enough distance from each other, and to move to a high enough position. Under the state, as shown in FIG. 4, the head 21 of a subject is positioned between the arms 12 and 13 so that the median sagittal plane becomes vertically to the central X-ray from the X-ray tube 11a. The subject may be in a sitting position, sitting on a chair or a standing position, standing up. Next, by descending the arms 12 and 13, the ear rods 17 and 18 are made to come to the height position of the right and left external acoustic openings of the head 21 of the subject. Next, the arms 12 and 13 are made to move translatory inside in the horizontal direction, inserting the ear rods 17 and 18 in the right and left external acoustic openings of the head 21 of the subject, fixing the head by making the uppermost point of the ear rods 17 and 18 contact with the porion, so that the irradiation direction of the central X-ray coincides with the central axis of the ear rods 17 and 18. Next, the inspector searches for the predetermined reference point of the face of the head 21, specifically, for example, the orbitale. And, as shown in FIG. 5, the seal 21 is put on the reference point. Next, the stand for X-ray radiographic apparatus shown in FIG. 11 is made to move on the floor surface, and the head tilt setting device 19 provided on the upper edge of the support bar 52 is made to come to the same position as the position shown in FIG. 4 for the head 21 of the subject. That is, the head tilt setting device 19 is made to contact with the exterior surface of the arm 13. And, under the state, as the same as the first embodiment, the inspector, using the angle scale 19a of the head tilt setting device 19, sets the straight line connecting the porion with the orbitale at an intended angle. And, by taking a radiograph at the position, a lateral cephalometric radiograph is taken.

(2) A Method of Taking a Posteroanterior Cephalometric Radiograph

When taking a posteroanterior cephalometric radiograph, using the head tilt setting device 19 provided on the upper edge of the support bar 52, as the same as the first embodiment, a posteroanterior cephalometric radiograph can be taken.

(3) A Method of Taking an Anteroposterior Cephalometric Radiograph

When taking an anteroposterior cephalometric radiograph, using the head tilt setting device 19 provided on the upper edge of the support bar 52, as the same as the first embodiment, an anteroposterior cephalometric radiograph can be taken.

(4) A Method of Taking a Cephalometric Radiograph from any Direction Between the Posteroanterior Direction and the Anteroposterior Direction When taking a cephalometric radiograph from any direction between the posteroanterior direction and the anteroposterior direction, using the head tilt setting device 19 provided on the upper edge of the support bar 52, as the same as the first embodiment, a cephalometric radiograph can be taken.

According to the second embodiment, the same advantages as the first embodiment can be obtained.

3. The Third Embodiment

In the cephalometric X-ray radiographic apparatus according to the third embodiment, unlike the cephalometric X-ray radiographic apparatus according to the first embodiment, the head tilt setting device 19 is not provided to the arm 13, but the head tilt setting device 19 is provided to a chair for X-ray radiographic apparatus attached to the cephalometric X-ray radiographic apparatus.

Figure 12:
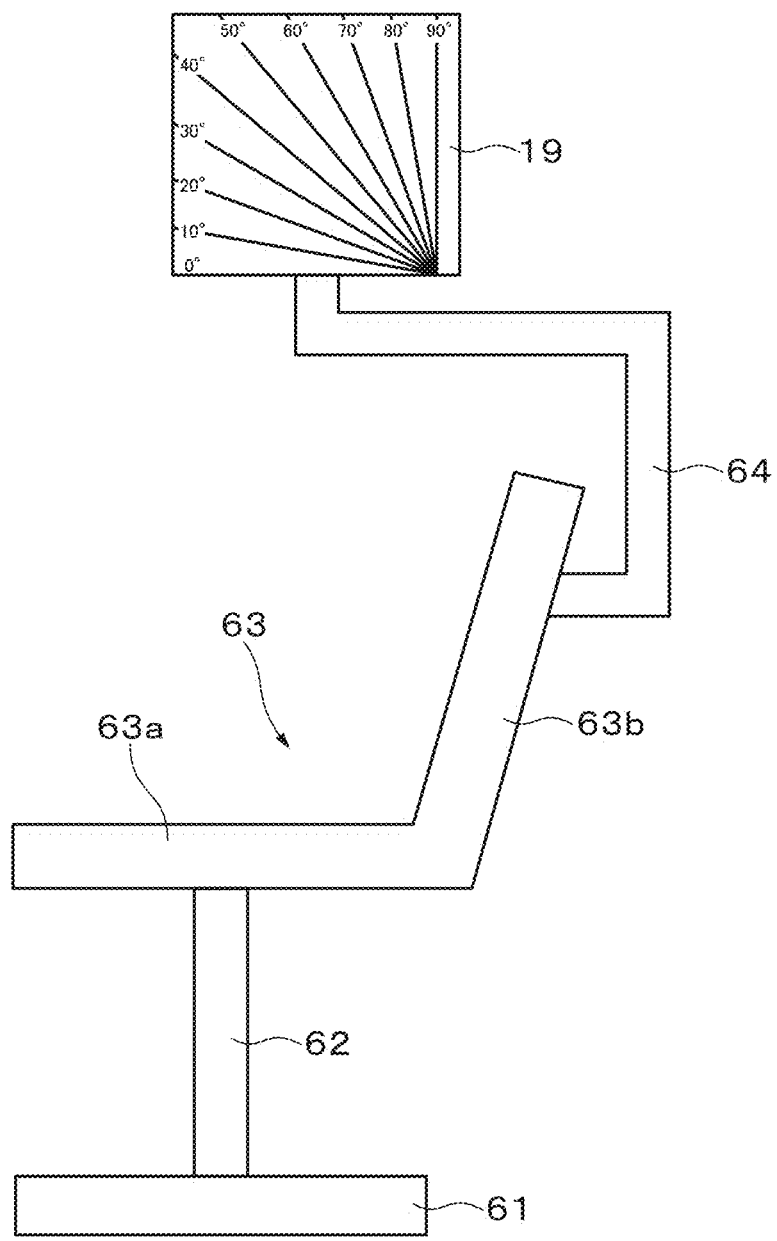
FIG. 12 A side view showing a chair for X-ray radiographic apparatus to be used in a cephalometric X-ray radiographic apparatus according to the third embodiment of the present invention.

FIG. 12 shows the chair for X-ray radiographic apparatus. As shown in FIG. 12, the chair for X-ray radiographic apparatus has a support platform 61 to be placed on the floor surface, a support bar 62 being stood vertically to the support platform 61, a main part 63 provided to the upper edge of the support bar 62, a support member 64 provided to the main part 63, and the head tilt setting device 19 provided to the upper edge of the support member 64. The main part 63 is comprised of a seating face 63a and a backrest 63b. The support bar 62 is constituted telescopically, and the height of the seating face 63a can be adjusted. The support member 64 is provided to the back of the backrest 63b of the main part 63. The support member 64 is comprised of a horizontal part and a vertical part, and the horizontal part is constituted telescopically in the horizontal direction for the backrest 63b, and the vertical part is constituted telescopically in the direction of the vertical line. For this, by adjusting the position on the floor surface of the chair for X-ray radiographic apparatus, the height of the seating face 63a, the length of the horizontal part and vertical part of the support member 64, etc., the positional relation between the head tilt setting device 19 and the head 21 can be set as the same as the first embodiment. With regards to the head tilt setting device 19, it is the same as the first embodiment.

Next, a method of taking a cephalometric radiograph of a subject using the cephalometric X-ray radiographic apparatus will be explained.

(1) A Method of Taking a Lateral Cephalometric Radiograph

In the cephalometric X-ray radiographic apparatus shown in FIG. 1 which is not provided with the head tilt setting device 19 to the arm 13, the arms 12 and 13 are made to move translatory outside in the horizontal direction, set apart enough distance from each other, and to move to high enough position. Under the state, as shown in FIG. 4, the head 21 of a subject is positioned between the arms 12 and 13 so that the median sagittal plane becomes vertically to the central X-ray from the X-ray tube 11a. The subject sits on the chair for X-ray radiographic apparatus shown in FIG. 12. Next, by descending the arms 12 and 13, the ear rods 17 and 18 are made to come to the height position of the right and left external acoustic openings of the head 21 of the subject. Next, the arms 12 and 13 are made to move translatory inside in the horizontal direction, the ear rods 17 and 18 are inserted in the right and left external acoustic openings of the head 21 of the subject, and the head is fixed by making the uppermost point of the ear rods 17 and 18 contact with the porion, so that the irradiation direction of the central X-ray coincides with the central axis of the ear rods 17 and 18. Next, the inspector searches for the predetermined reference point of the face of the head 21, specifically, for example, the orbitale. And as shown in FIG. 5, the seal 21 is put on the reference point. Next, by adjusting the position on the floor surface of the chair for X-ray radiographic apparatus, the height of the sitting face 63a, and the length of the horizontal part and the vertical part of the support member 64, etc., the head tilt setting device 19 is made to come to the same position with the position shown in FIG. 4 for the head 21 of the subject. That is, the head tilt setting device 19 is made to contact with the exterior surface of the arm 13. And, under the state, as the same as the first embodiment, the inspector sets the straight line connecting the porion with the orbitale at the intended angle by using the angle scale 19a of the head tilt setting device 19. And, by taking a radiograph at the position, a lateral cephalometric radiograph is taken.

(2) A Method of Taking a Posteroanterior Cephalometric Radiograph

When taking a posteroanterior cephalometric radiograph, using the head tilt setting device 19 provided to the chair for X-ray radiographic apparatus shown in FIG. 12, as the same as the first embodiment, a posteroanterior cephalometric radiograph can be taken.

(3) A Method of Taking an Anteroposterior Cephalometric Radiograph

When taking an anteroposterior cephalometric radiograph, using the head tilt setting device 19 provided to the chair for X-ray radiographic apparatus shown in FIG. 12, as the same as the first embodiment, an anteroposterior cephalometric radiograph can be taken.

(4) A Method of Taking a Cephalometric Radiograph from any Direction Between the Posteroanterior Direction and the Anteroposterior Direction When taking a cephalometric radiograph from any direction between the posteroanterior direction and the anteroposterior direction, using the head tilt setting device 19 provided to the chair for X-ray radiographic apparatus shown in FIG. 12, as the same as the first embodiment, a cephalometric radiograph can be taken.

According to the third embodiment, the same advantages as the first embodiment can be obtained.

4. The Fourth Embodiment

Figure 13:
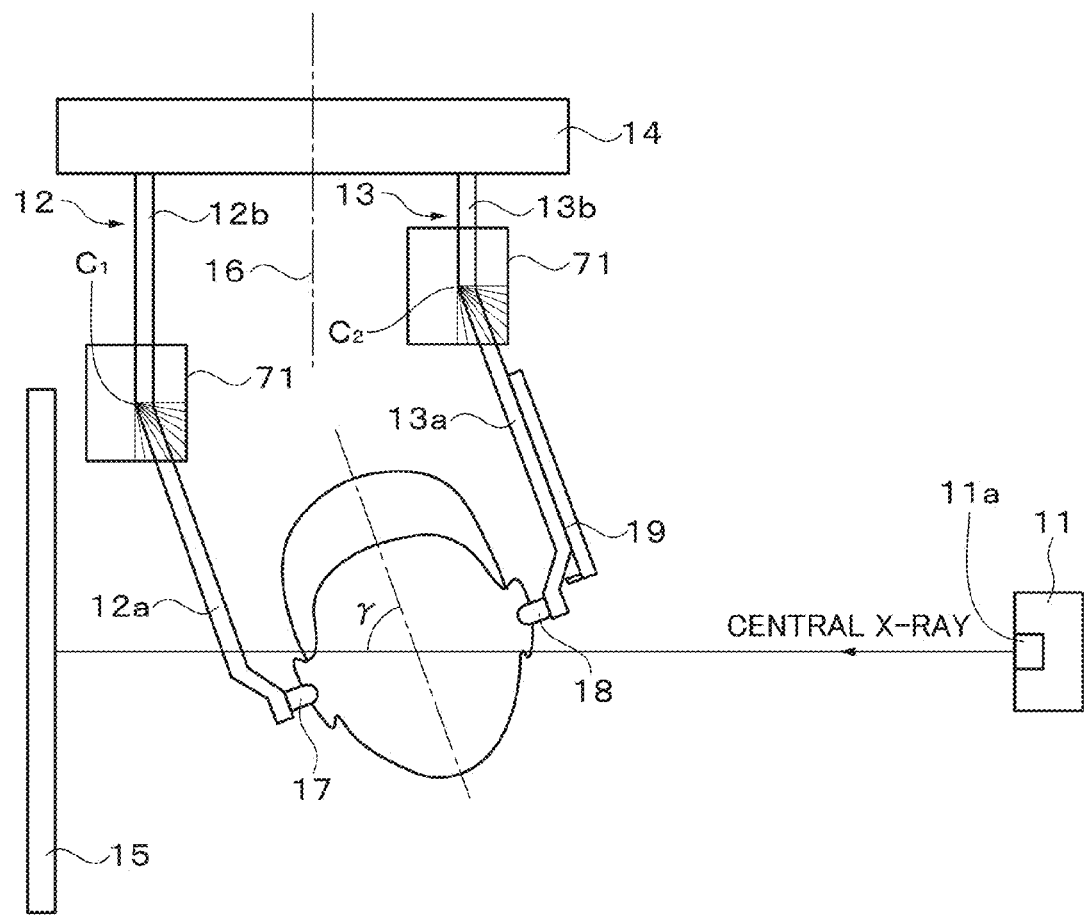
FIG. 13 A schematic drawing for explaining a cephalometric X-ray radiographic apparatus according to the fourth embodiment of the present invention.

FIG. 13 shows the cephalometric X-ray radiographic apparatus according to the fourth embodiment. As shown in FIG. 13, in the cephalometric X-ray radiographic apparatus, the lower parts 12a and 13a of the arms 12 and 13 can be folded at an angle in the predetermined range relative to the upper parts 12b and 13b, and can be fixed at the angle. Here, the lower part 12a of the arm 12 can rotate around the point $C_1$ of FIG. 13, and the lower part 13a of the arm 13 can rotate around the point $C_2$ of FIG. 13. Also, by the arm control device 14, the arms 12 and 13 can move up and down in the direction parallel to the reference line 16 independently from each other. In other words, the lower parts 12a and 13a of the arms 12 and 13 can be positioned at the different height each other.

At one of the edges of the upper parts 12b and 13b of the arms 12 and 13, a lower part of the arm tilt setting device 71 composed of a rectangular transparent plate parallel to the vertical line for setting the inclination angle (angle γ relative to the vertical line, in case the upper parts 12b and 13b are parallel to the vertical line) relative to the upper parts 12b and 13b of the lower parts 12a and 13a of the arms 12 and 13 is provided. A method of fixing the lower part of the arm tilt setting device 71 is not specifically limited, may be adhesion, clip-on, screwed, etc.

Figure 14:
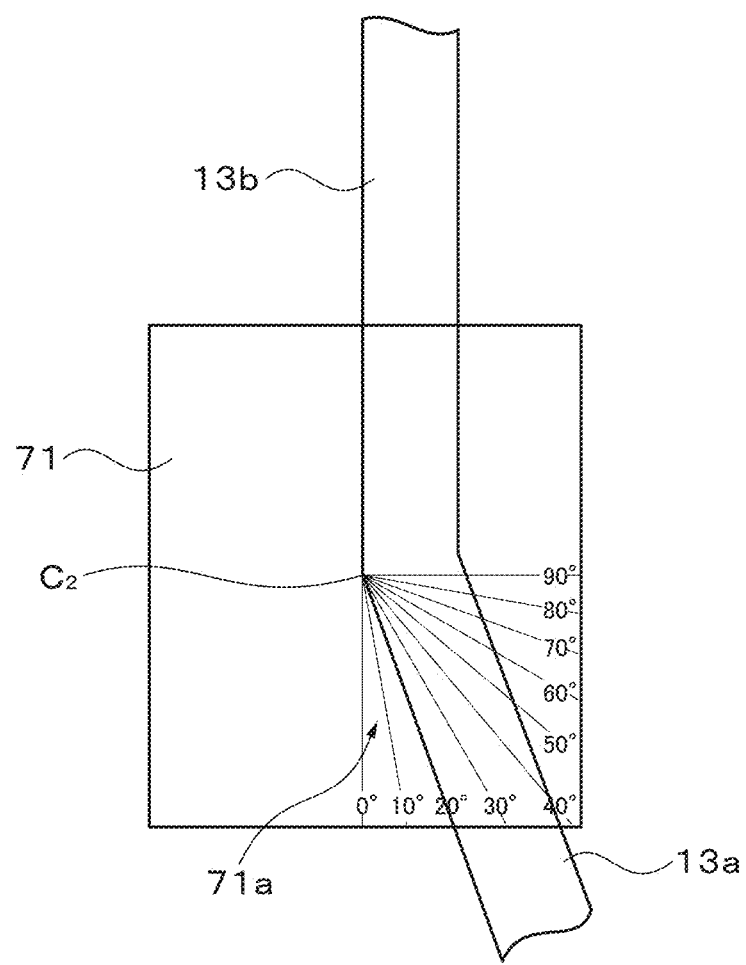
FIG. 14 A schematic drawing showing an arm of the cephalometric X-ray radiographic apparatus according to the fourth embodiment of the present invention, and a lower part of the arm tilt setting device provided on the arm.
Figure 15:
FIG. 15 A substitute picture for a drawing showing a lateral cephalometric radiograph of a subject 1 taken by using the cephalometric X-ray radiographic apparatus according to the first embodiment of the present invention.
Figure 16:
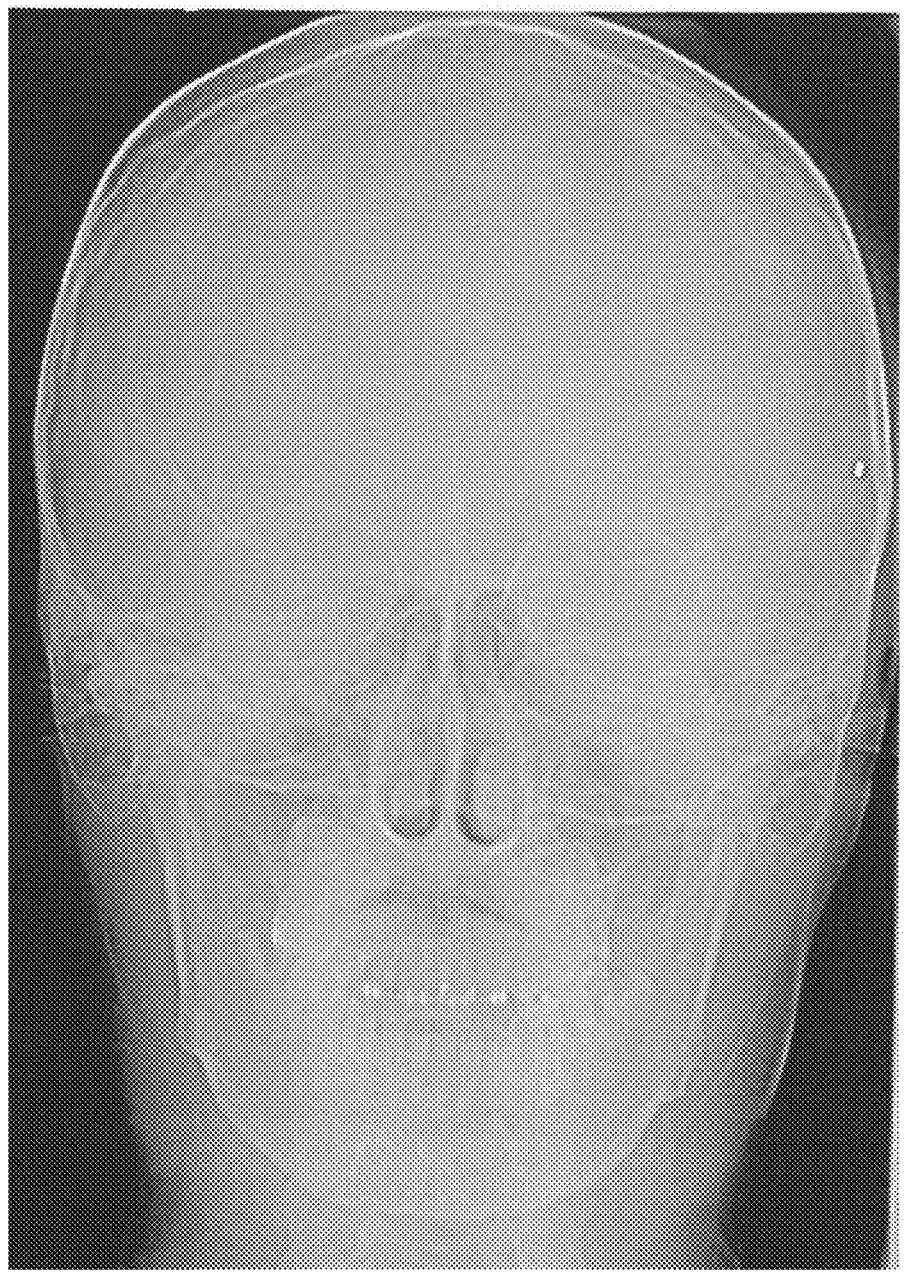
FIG. 16 A substitute picture for a drawing showing a posteroanterior cephalometric radiograph of the subject 1 taken by using the cephalometric X-ray radiographic apparatus according to the first embodiment of the present invention.
Figure 17:
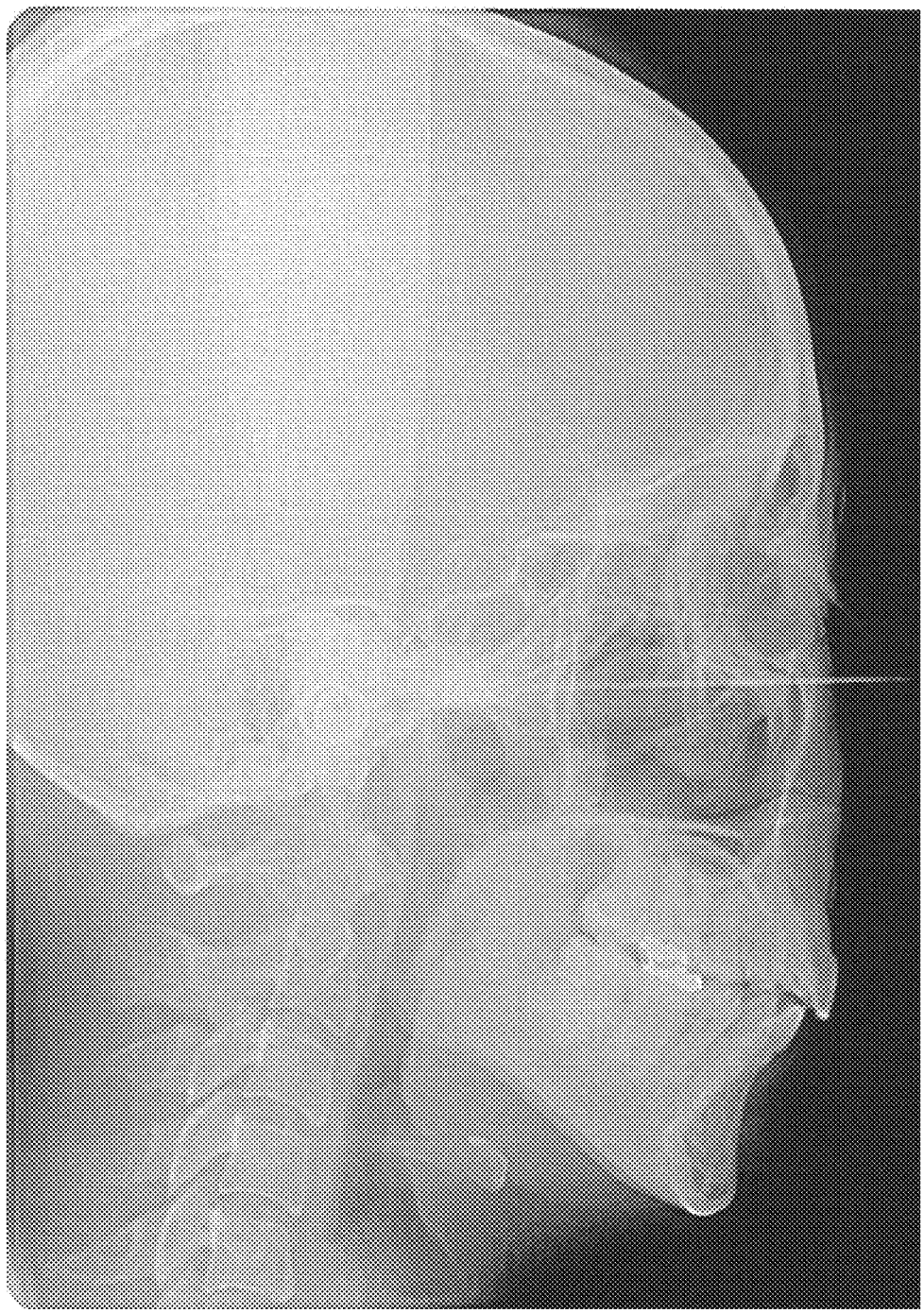
FIG. 17 A substitute picture for a drawing showing a lateral cephalometric radiograph of a subject 2 taken by using the cephalometric X-ray radiographic apparatus according to the first embodiment of the present invention.
Figure 18:
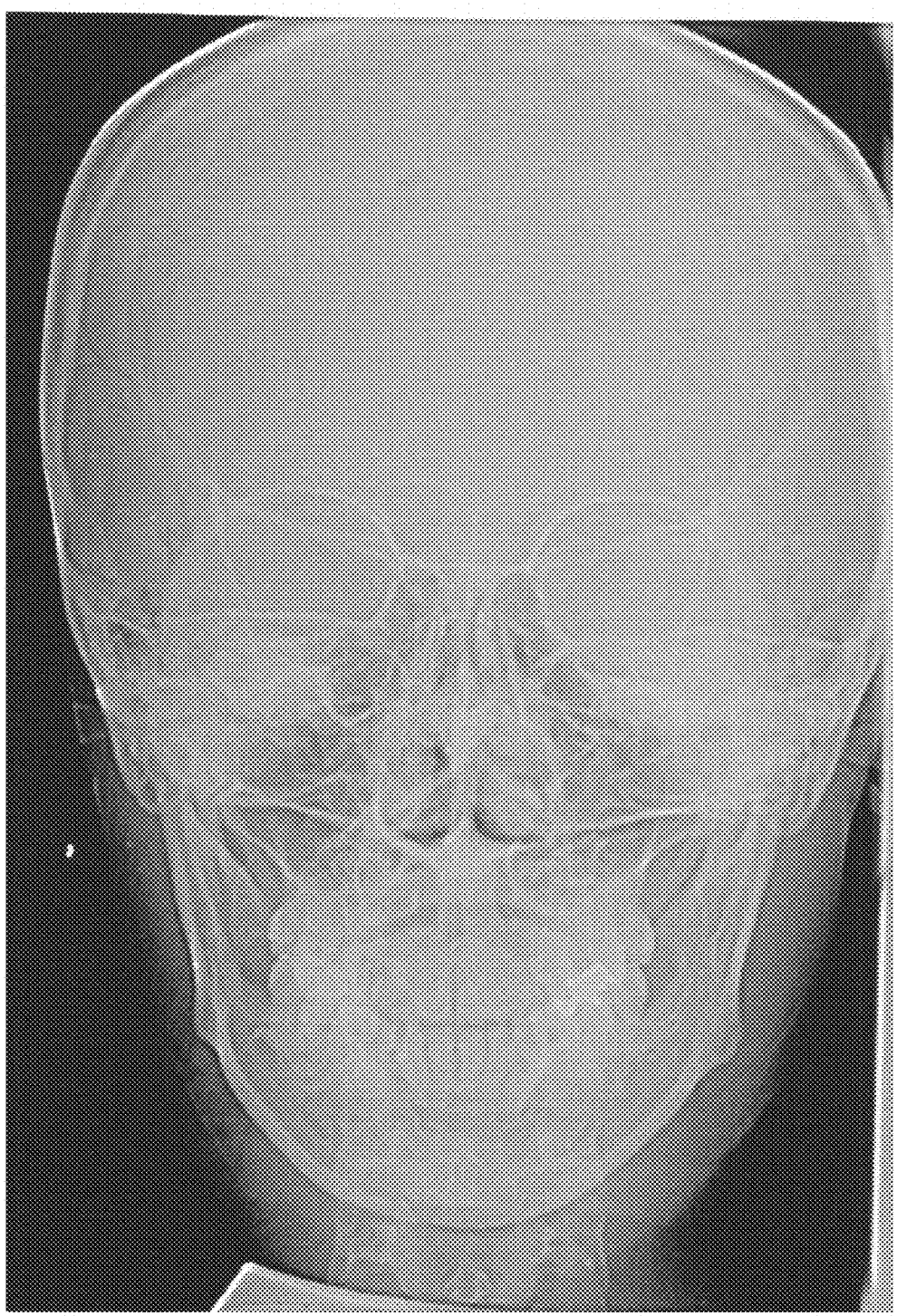
FIG. 18 A substitute picture for a drawing showing a posteroanterior cephalometric radiograph of the subject 2 taken by using the cephalometric X-ray radiographic apparatus according to the first embodiment of the present invention.
Figure 19:
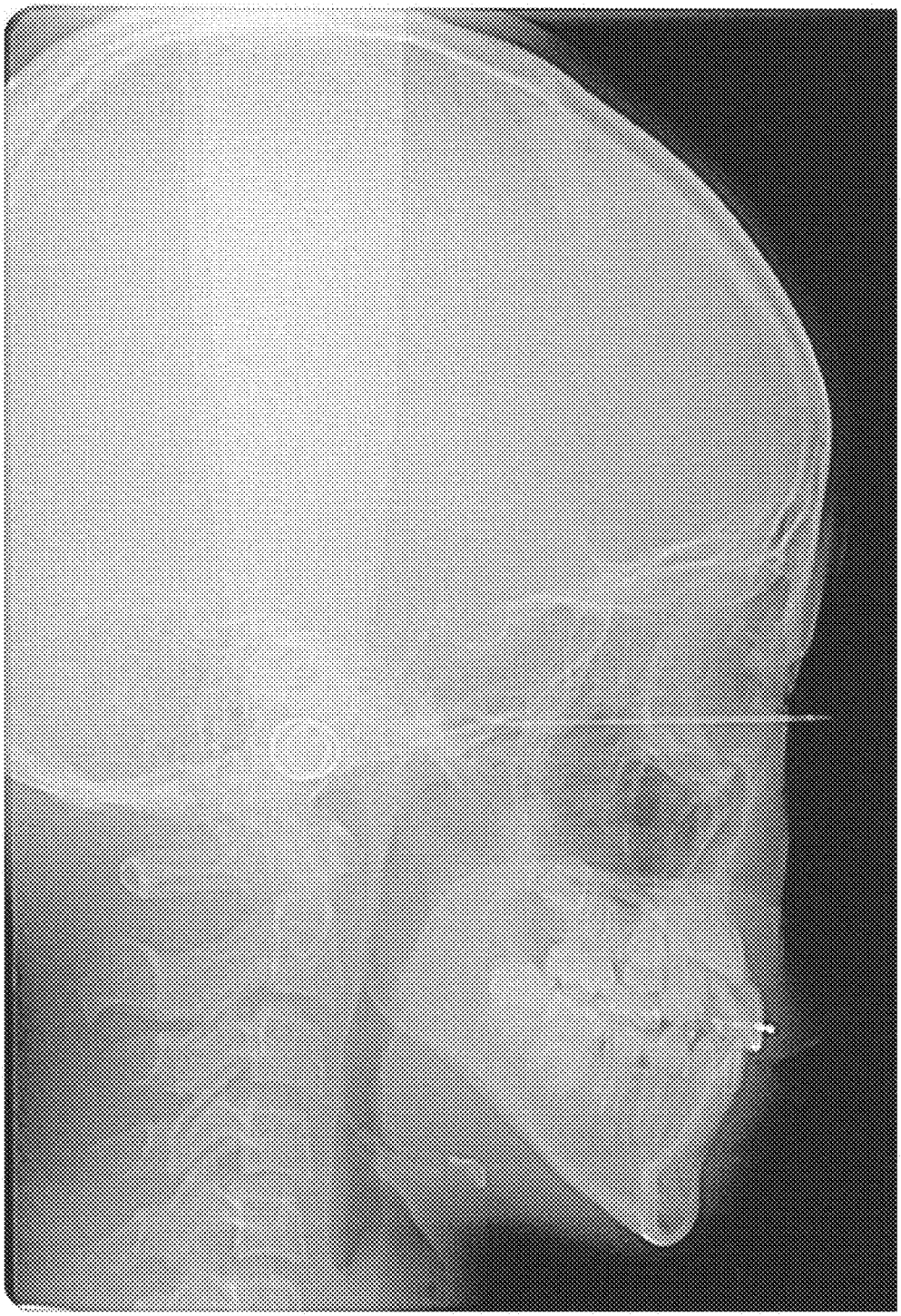
FIG. 19 A substitute picture for a drawing showing a lateral cephalometric radiograph of a subject 3 taken by using the cephalometric X-ray radiographic apparatus according to the first embodiment of the present invention.
Figure 20:
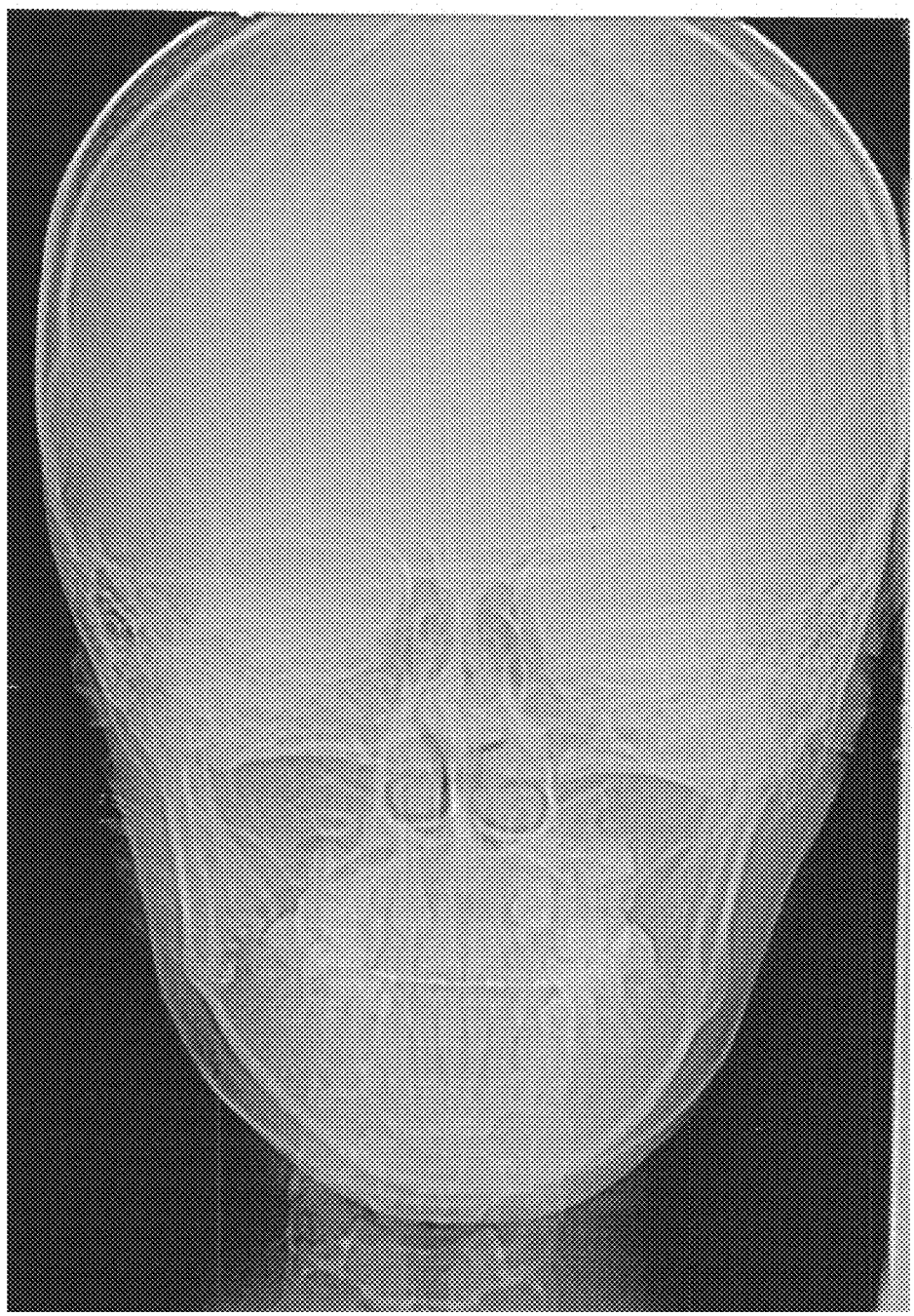
FIG. 20 A substitute picture for a drawing showing a posteroanterior cephalometric radiograph of the subject 3 taken by using the cephalometric X-ray radiographic apparatus according to the first embodiment of the present invention.
Figure 21:
FIG. 21 A substitute picture for a drawing showing a lateral cephalometric radiograph of a subject 4 taken by using the cephalometric X-ray radiographic apparatus according to the first embodiment of the present invention.
Figure 22:
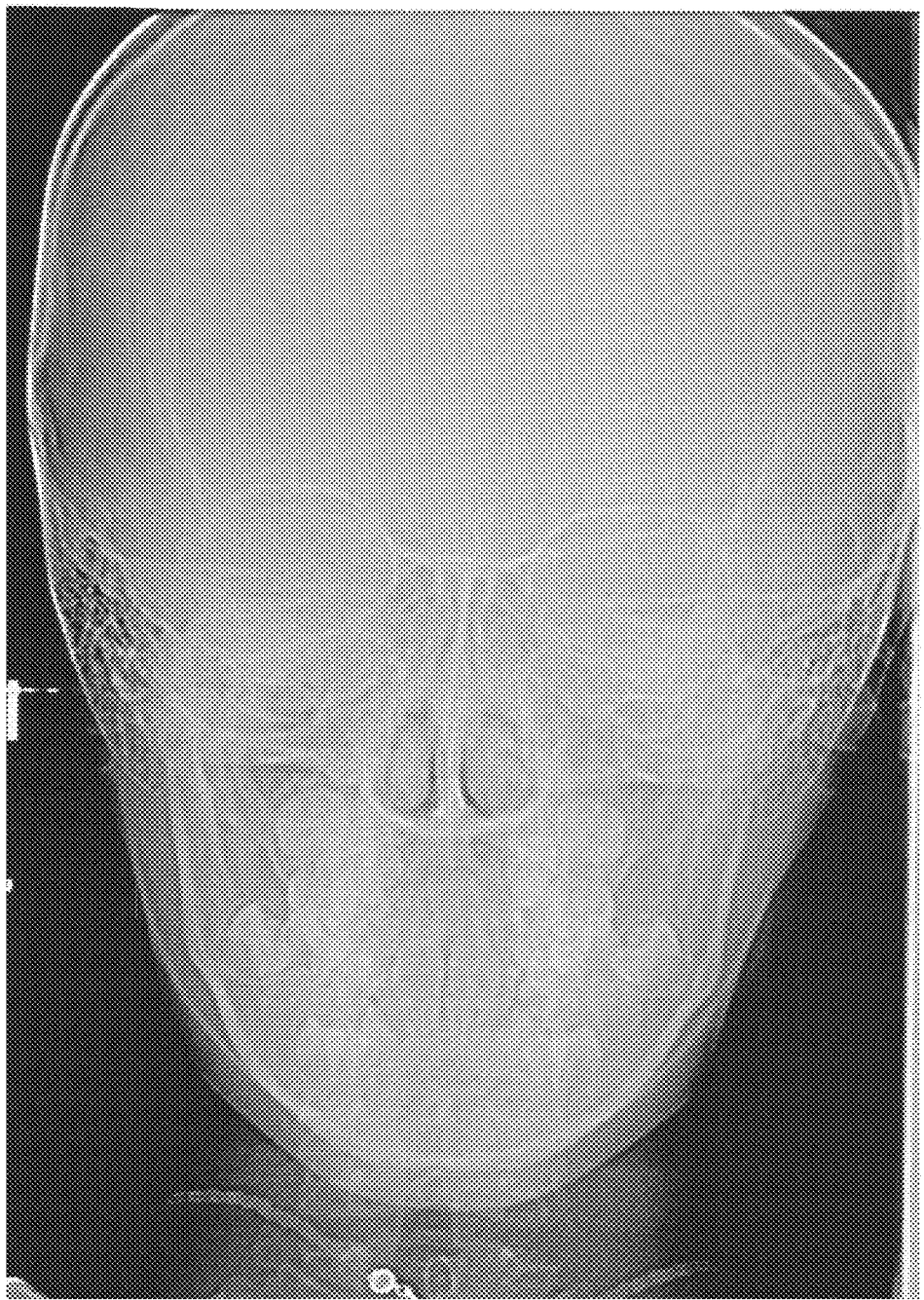
FIG. 22 A substitute picture for a drawing showing a posteroanterior cephalometric radiograph of the subject 4 taken by using the cephalometric X-ray radiographic apparatus according to the first embodiment of the present invention.
Figure 23:
FIG. 23 A substitute picture for a drawing showing a lateral cephalometric radiograph of a subject 5 taken by using the cephalometric X-ray radiographic apparatus according to the first embodiment of the present invention.
Figure 24:
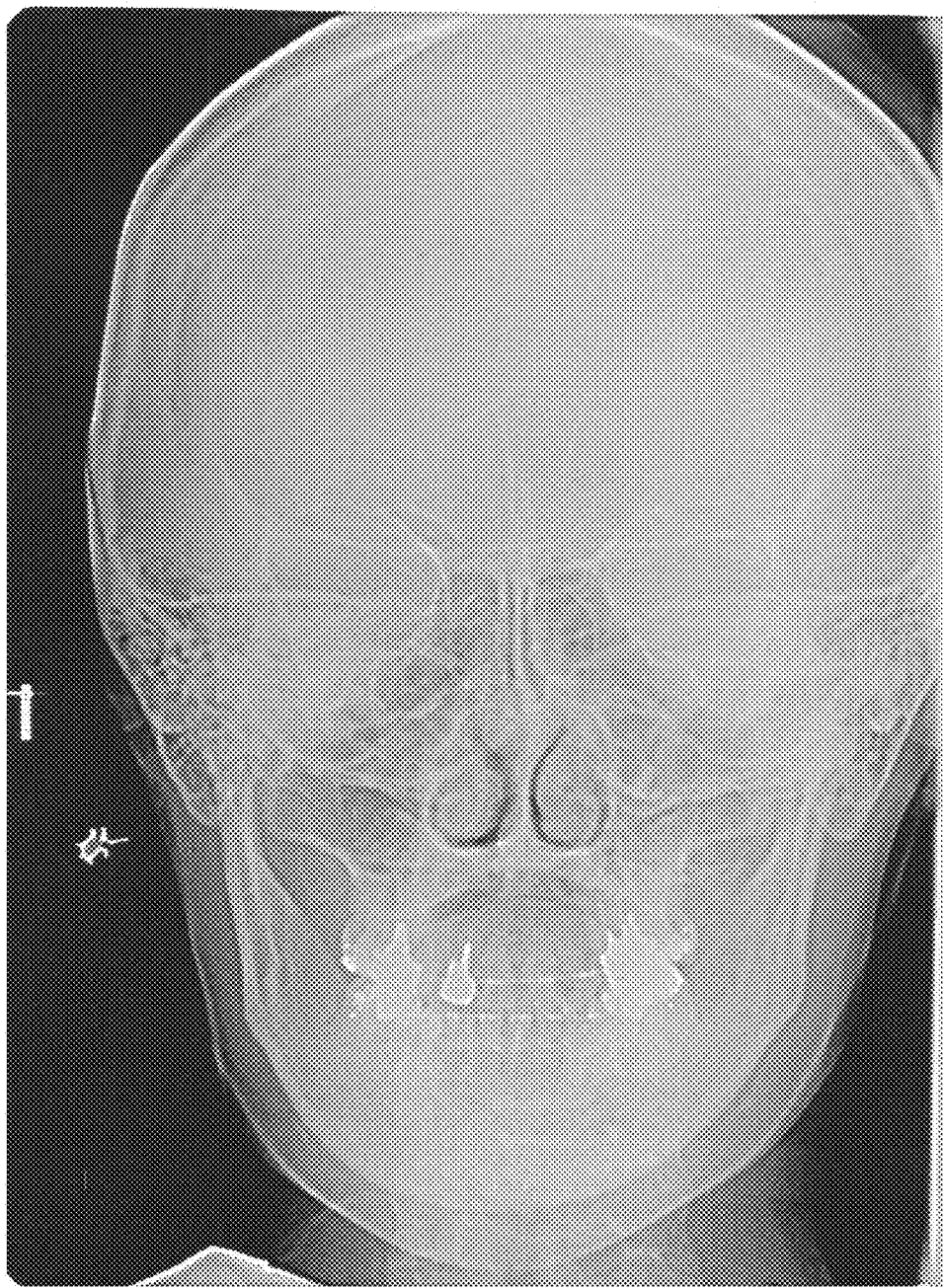
FIG. 24 A substitute picture for a drawing showing a posteroanterior cephalometric radiograph of the subject 5 taken by using the cephalometric X-ray radiographic apparatus according to the first embodiment of the present invention.
Figure 25:
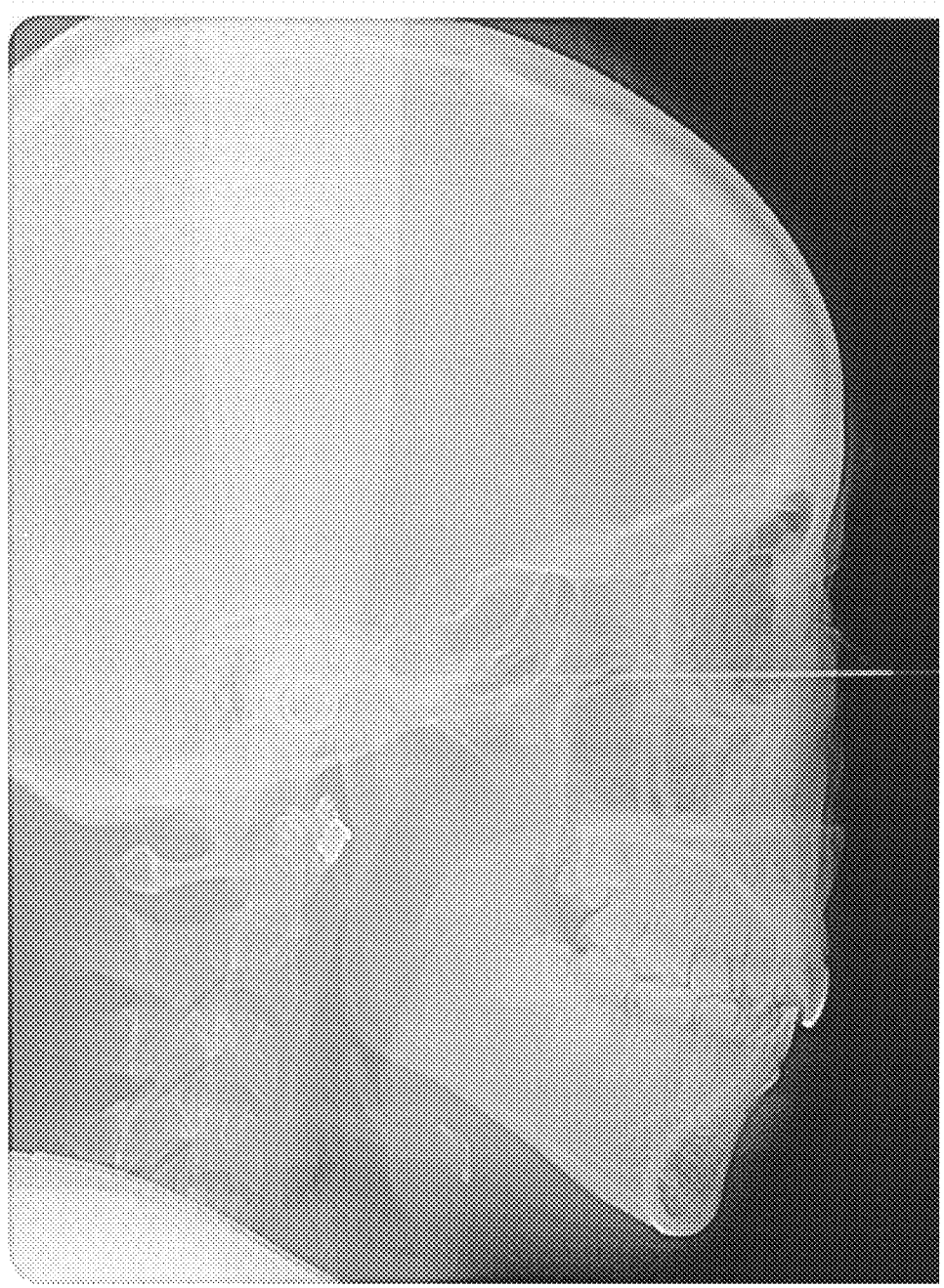
FIG. 25 A substitute picture for a drawing showing a lateral cephalometric radiograph of a subject 6 taken by using the cephalometric X-ray radiographic apparatus according to the first embodiment of the present invention.
Figure 26:
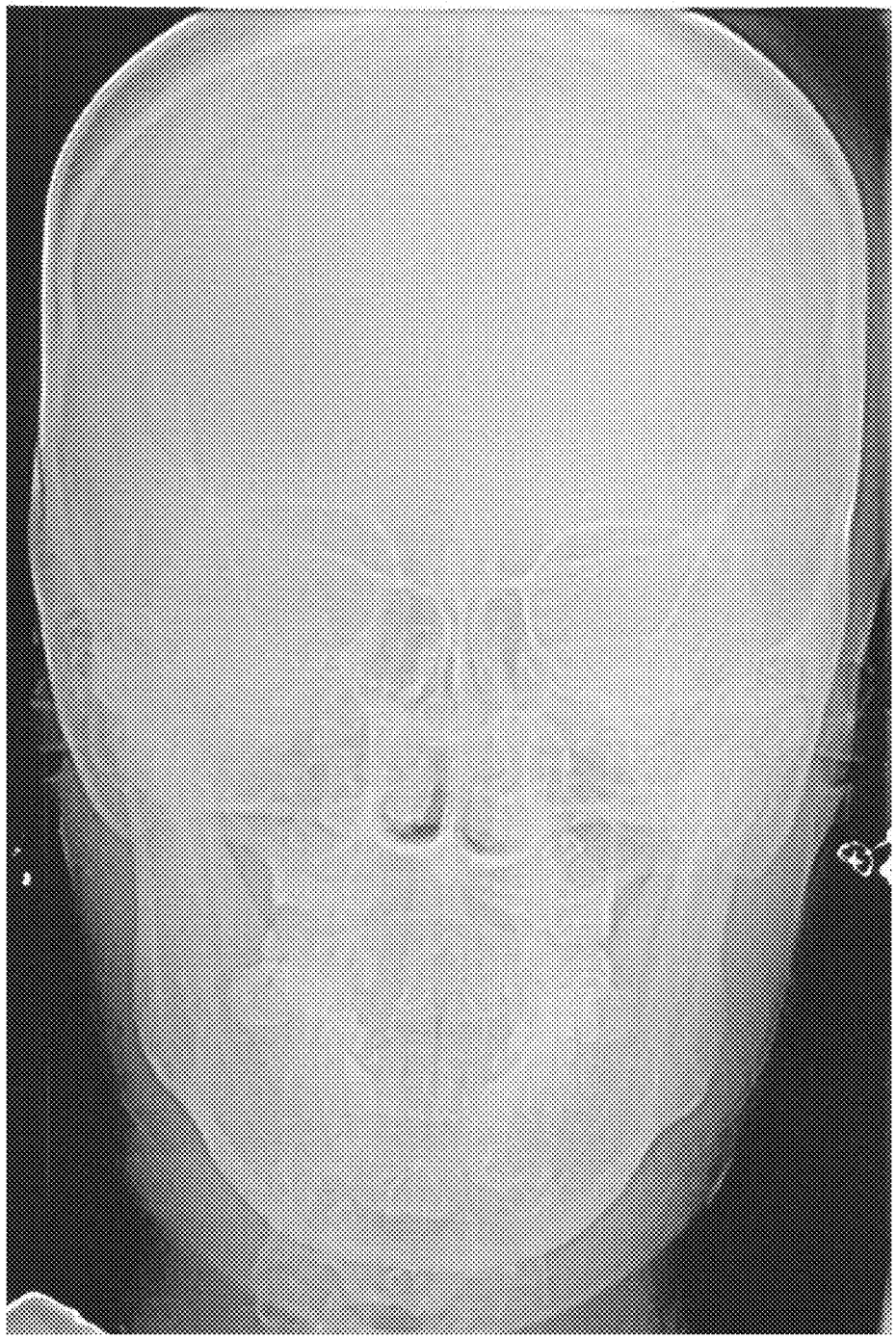
FIG. 26 A substitute picture for a drawing showing a posteroanterior cephalometric radiograph of the subject 6 taken by using the cephalometric X-ray radiographic apparatus according to the first embodiment of the present invention.
Figure 27:
FIG. 27 A substitute picture for a drawing showing a lateral cephalometric radiograph of a subject 7 taken by using the cephalometric X-ray radiographic apparatus according to the first embodiment of the present invention.
Figure 28:
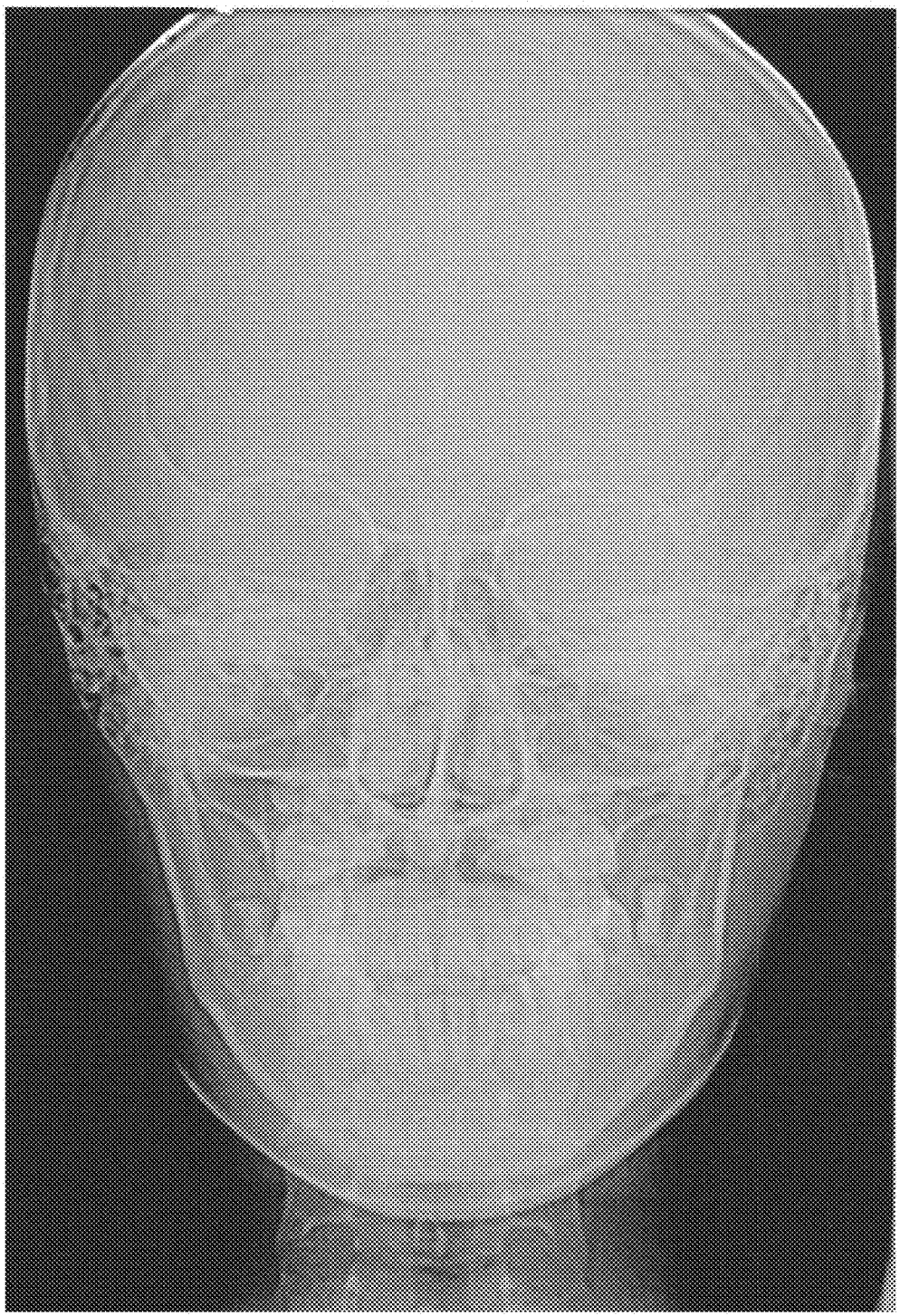
FIG. 28 A substitute picture for a drawing showing a posteroanterior cephalometric radiograph of the subject 7 taken by using the cephalometric X-ray radiographic apparatus according to the first embodiment of the present invention.
Figure 29:
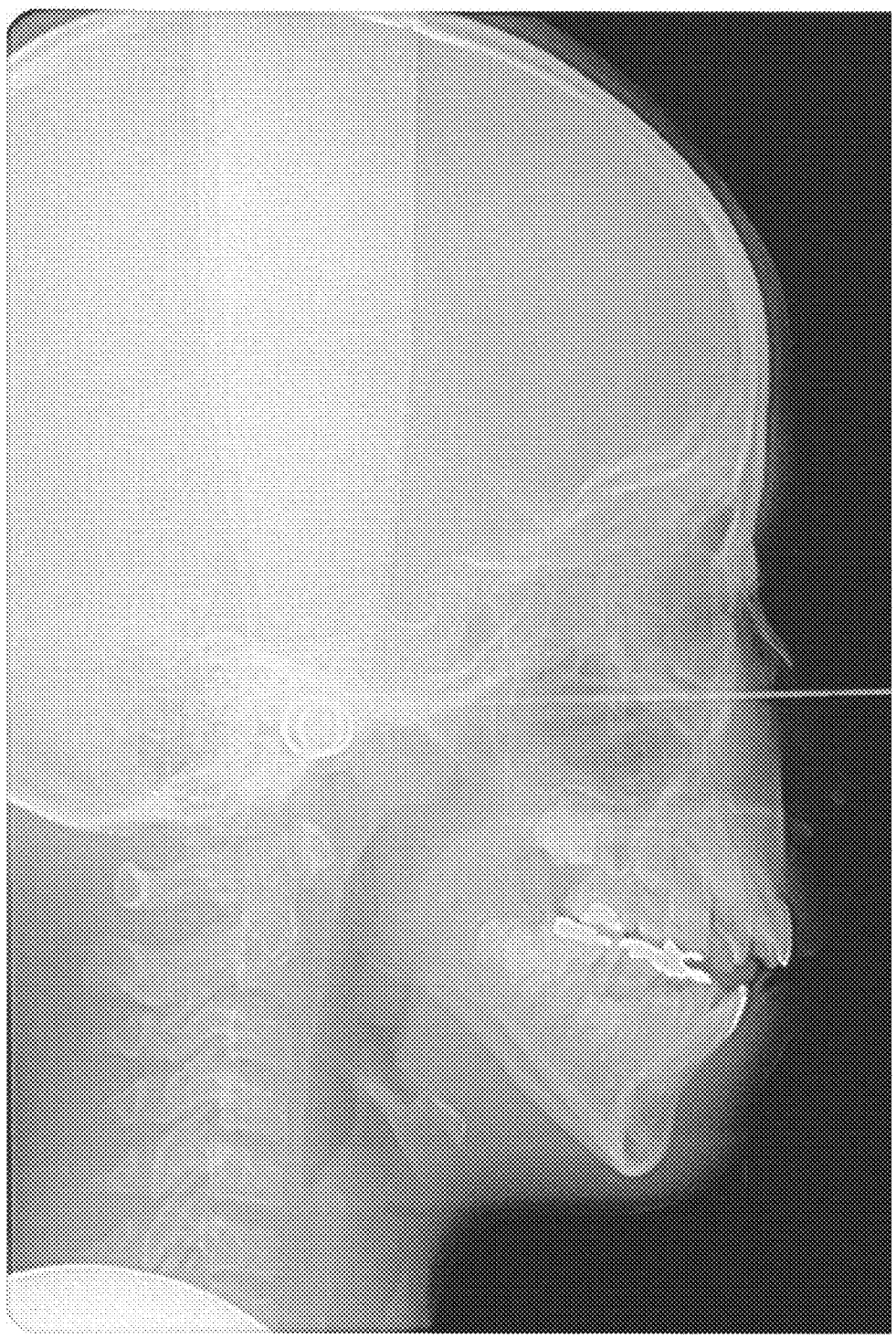
FIG. 29 A substitute picture for a drawing showing a lateral cephalometric radiograph of a subject 8 taken by using the cephalometric X-ray radiographic apparatus according to the first embodiment of the present invention.
Figure 30:
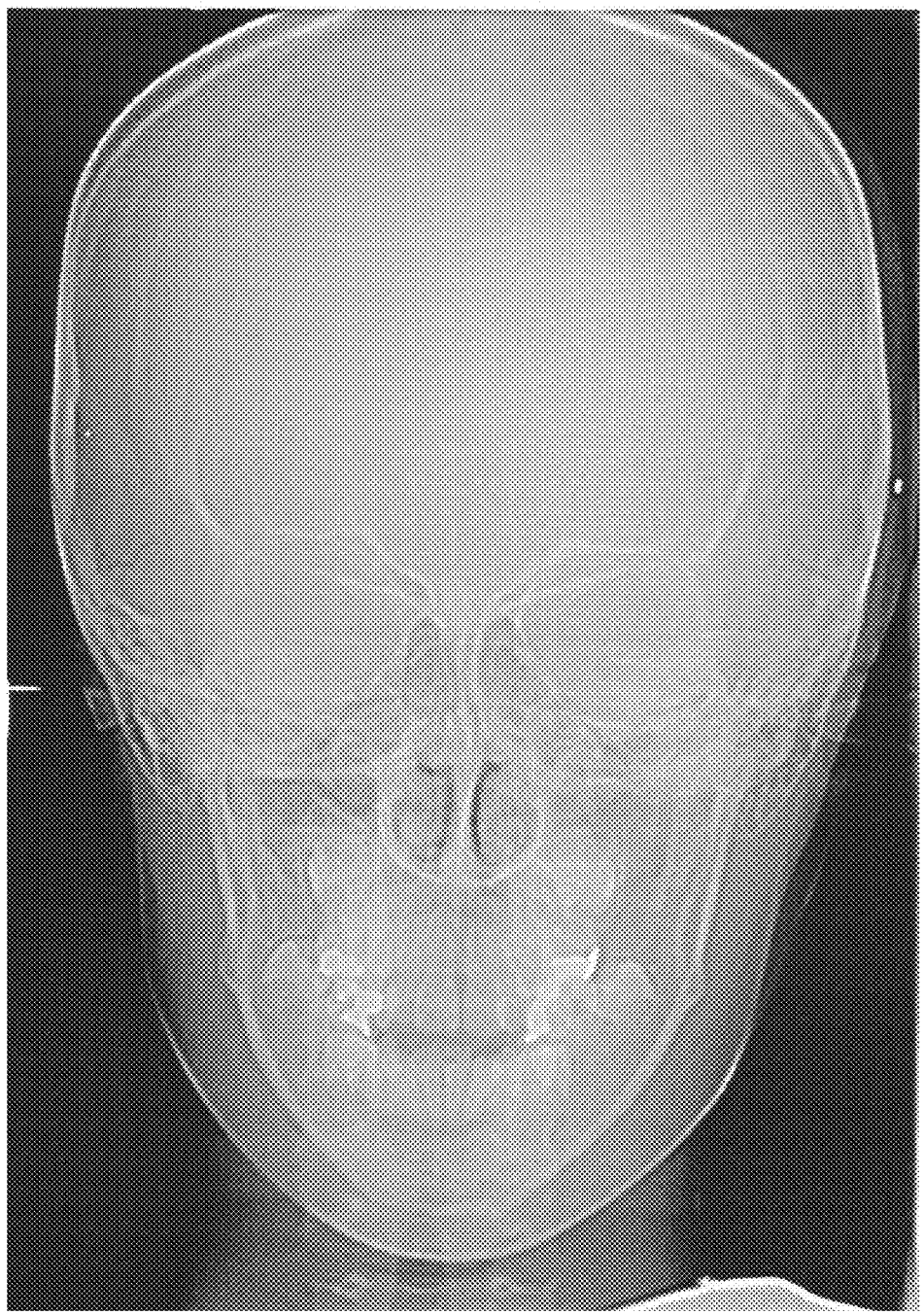
FIG. 30 A substitute picture for a drawing showing a posteroanterior cephalometric radiograph of the subject 8 taken by using the cephalometric X-ray radiographic apparatus according to the first embodiment of the present invention.
Figure 31:
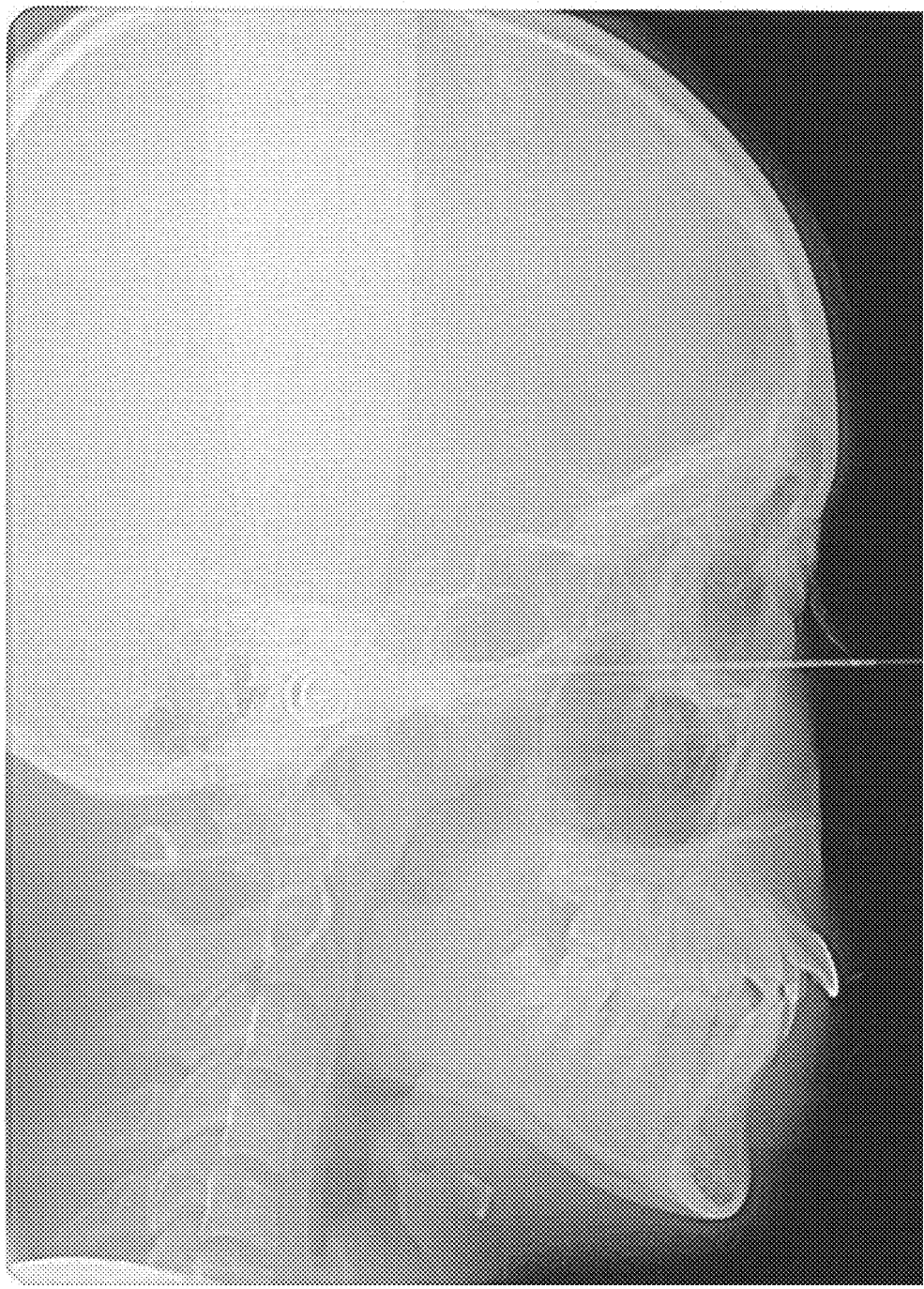
FIG. 31 A substitute picture for a drawing showing a lateral cephalometric radiograph of a subject 9 taken by using the cephalometric X-ray radiographic apparatus according to the first embodiment of the present invention.
Figure 32:
FIG. 32 A substitute picture for a drawing showing a posteroanterior cephalometric radiograph of the subject 9 taken by using the cephalometric X-ray radiographic apparatus according to the first embodiment of the present invention.
Figure 33:
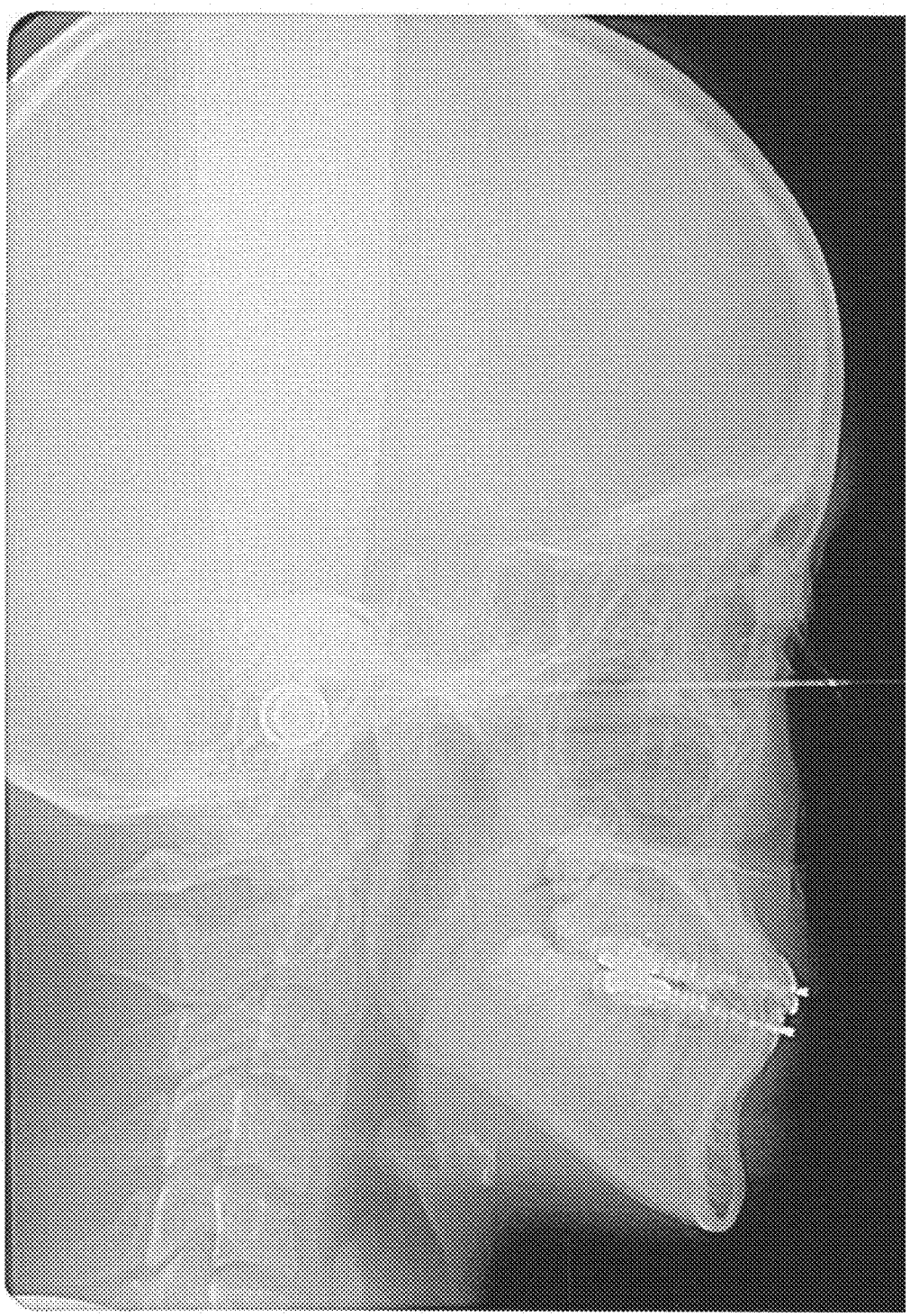
FIG. 33 A substitute picture for a drawing showing a lateral cephalometric radiograph of a subject 10 taken by using the cephalometric X-ray radiographic apparatus according to the first embodiment of the present invention.
Figure 34:
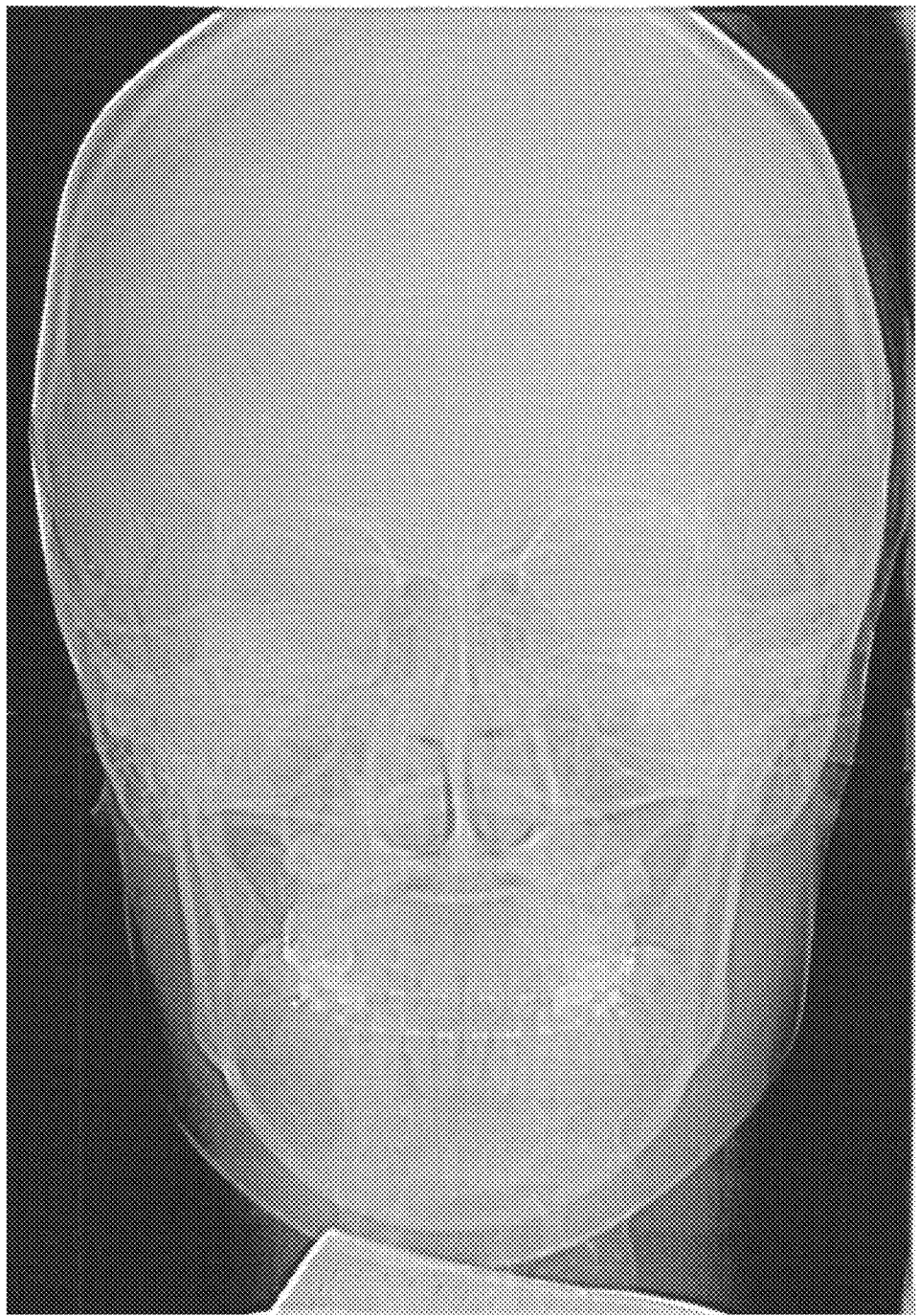
FIG. 34 A substitute picture for a drawing showing a posteroanterior cephalometric radiograph of the subject 10 taken by using the cephalometric X-ray radiographic apparatus according to the first embodiment of the present invention.
Figure 35:
FIG. 35 A substitute picture for a drawing showing a lateral cephalometric radiograph of a subject 11 taken by using the cephalometric X-ray radiographic apparatus according to the first embodiment of the present invention.
Figure 36:
FIG. 36 A substitute picture for a drawing showing a posteroanterior cephalometric radiograph of the subject 11 taken by using the cephalometric X-ray radiographic apparatus according to the first embodiment of the present invention.
Figure 37:
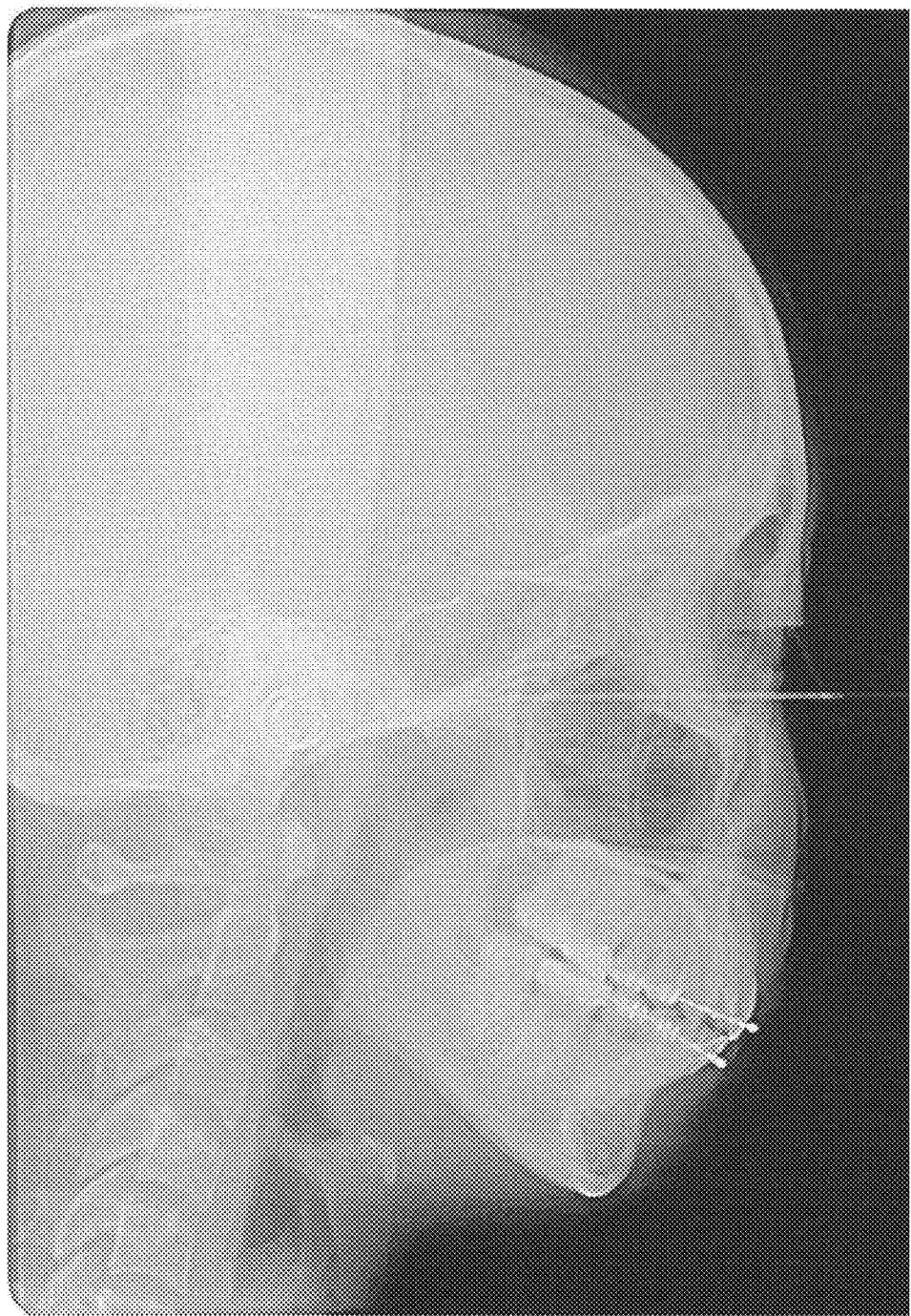
FIG. 37 A substitute picture for a drawing showing a lateral cephalometric radiograph of a subject 12 taken by using the cephalometric X-ray radiographic apparatus according to the first embodiment of the present invention.
Figure 38:
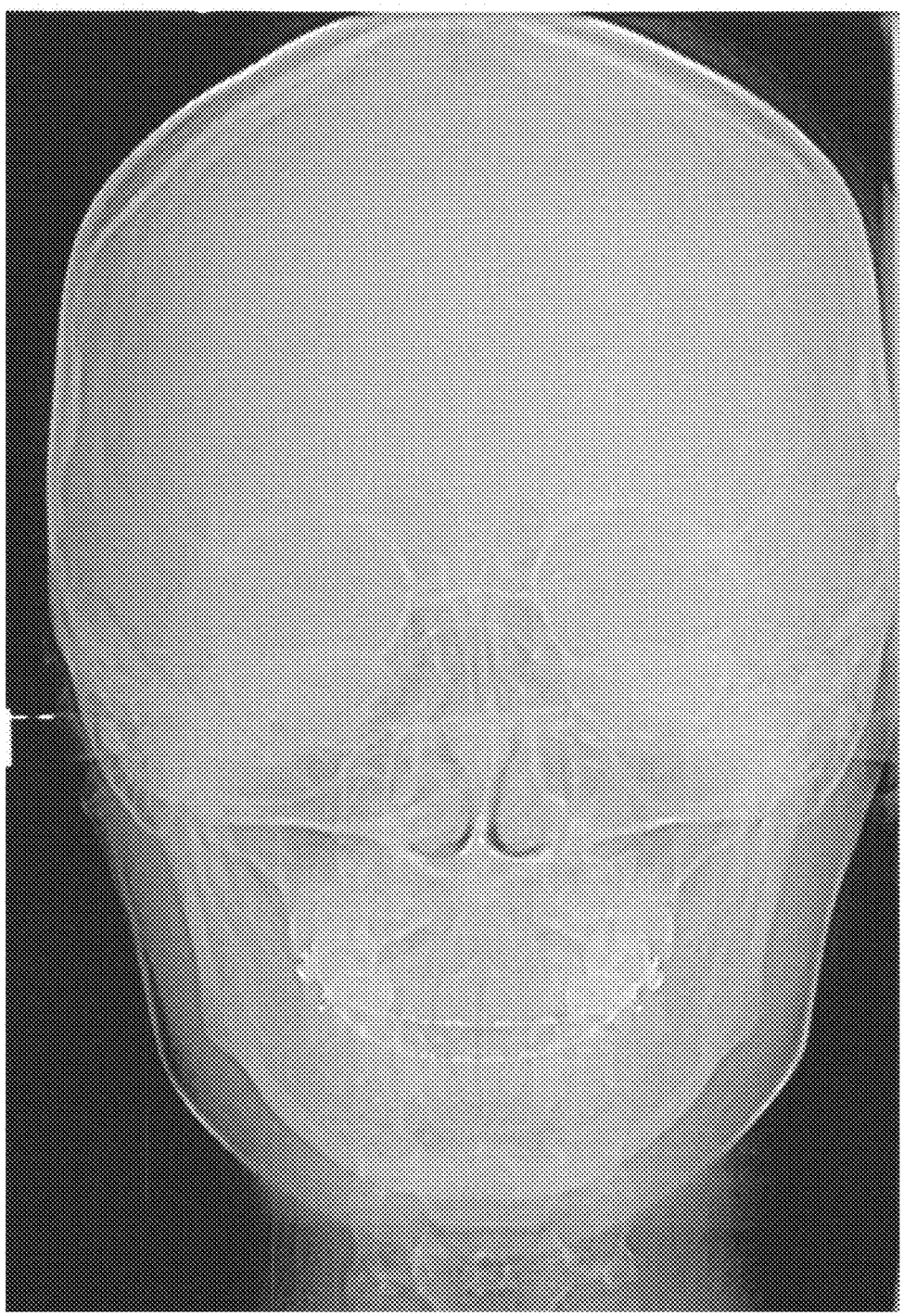
FIG. 38 A substitute picture for a drawing showing a posteroanterior cephalometric radiograph of the subject 12 taken by using the cephalometric X-ray radiographic apparatus according to the first embodiment of the present invention.
Figure 39:
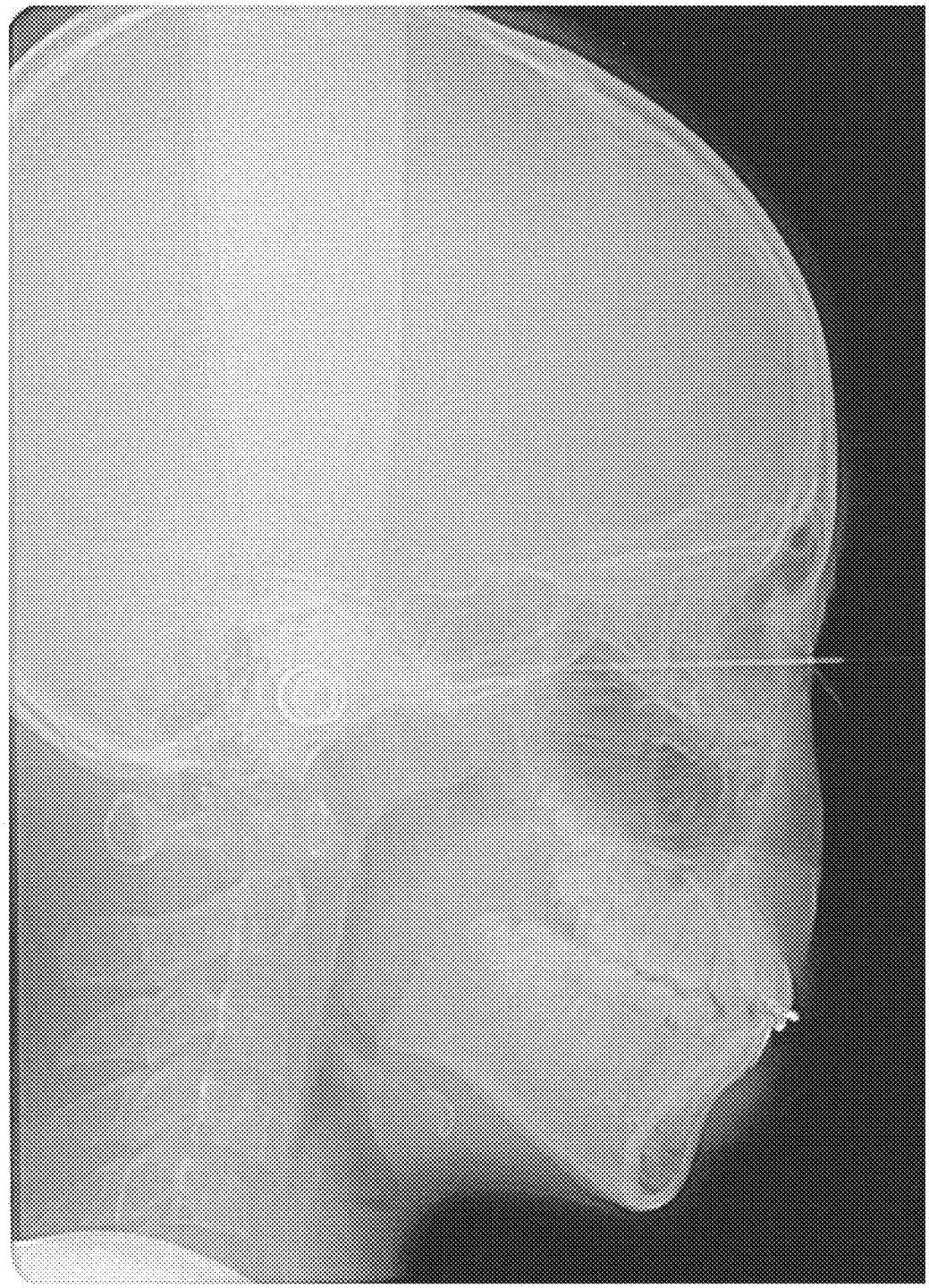
FIG. 39 A substitute picture for a drawing showing a lateral cephalometric radiograph of a subject 13 taken by using the cephalometric X-ray radiographic apparatus according to the first embodiment of the present invention.
Figure 40:
FIG. 40 A substitute picture for a drawing showing a posteroanterior cephalometric radiograph of the subject 13 taken by using the cephalometric X-ray radiographic apparatus according to the first embodiment of the present invention.
Figure 41:
FIG. 41 A substitute picture for a drawing showing a lateral cephalometric radiograph of a subject 14 taken by using the cephalometric X-ray radiographic apparatus according to the first embodiment of the present invention.
Figure 42:
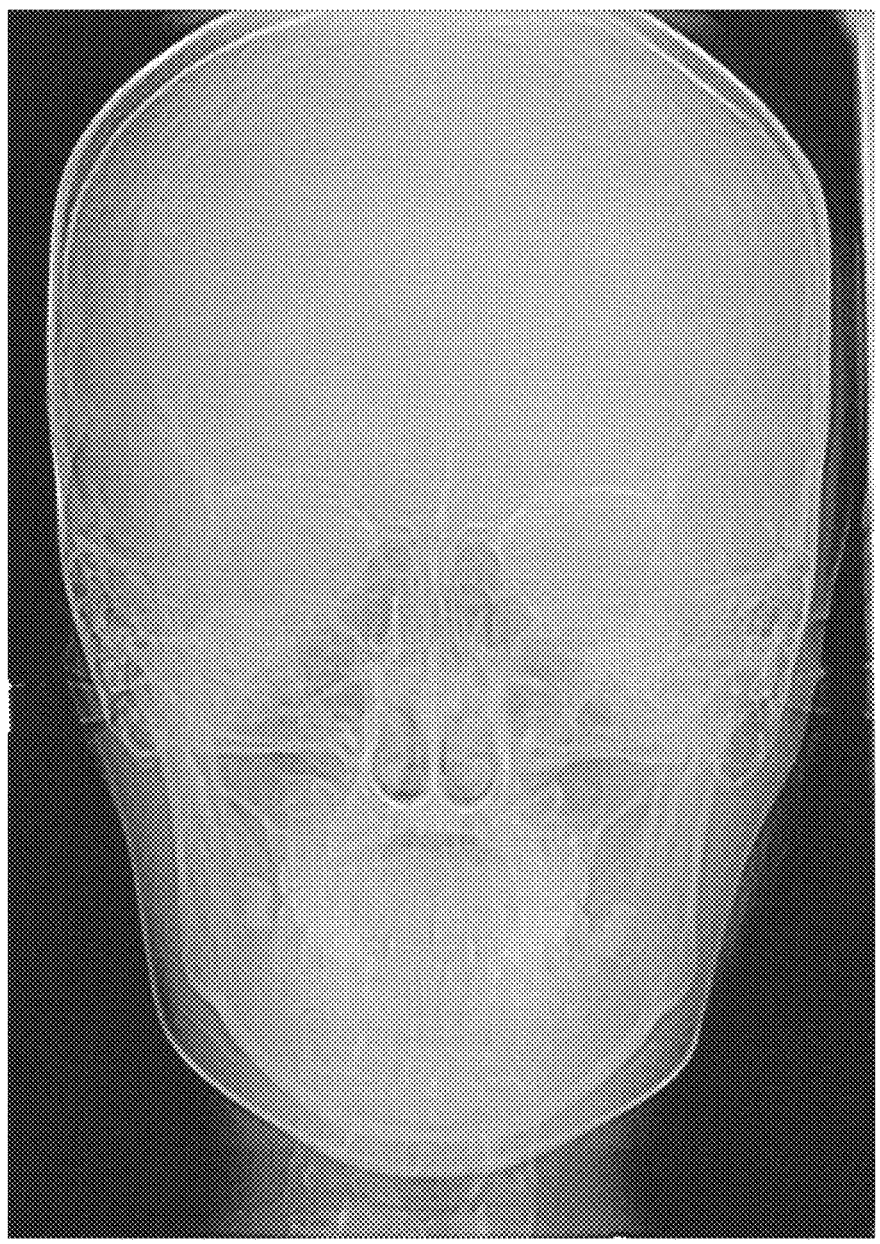
FIG. 42 A substitute picture for a drawing showing a posteroanterior cephalometric radiograph of the subject 14 taken by using the cephalometric X-ray radiographic apparatus according to the first embodiment of the present invention.
Figure 43:
FIG. 43 A substitute picture for a drawing showing a lateral cephalometric radiograph of a subject 15 taken by using the cephalometric X-ray radiographic apparatus according to the first embodiment of the present invention.
Figure 44:
FIG. 44 A substitute picture for a drawing showing a posteroanterior cephalometric radiograph of the subject 15 taken by using the cephalometric X-ray radiographic apparatus according to the first embodiment of the present invention.
Figure 45:
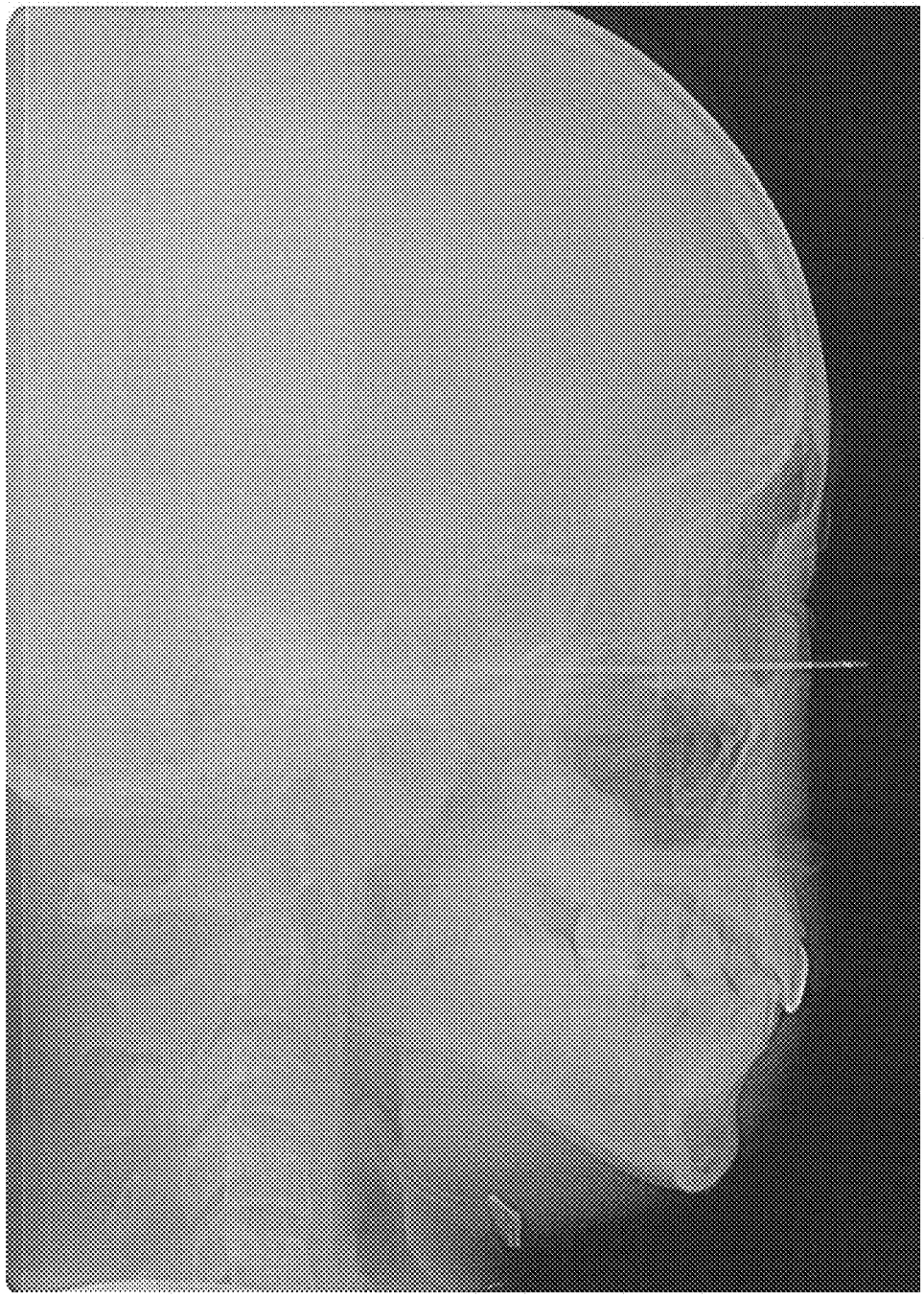
FIG. 45 A substitute picture for a drawing showing a lateral cephalometric radiograph of a subject 16 taken by using the cephalometric X-ray radiographic apparatus according to the first embodiment of the present invention.
Figure 46:
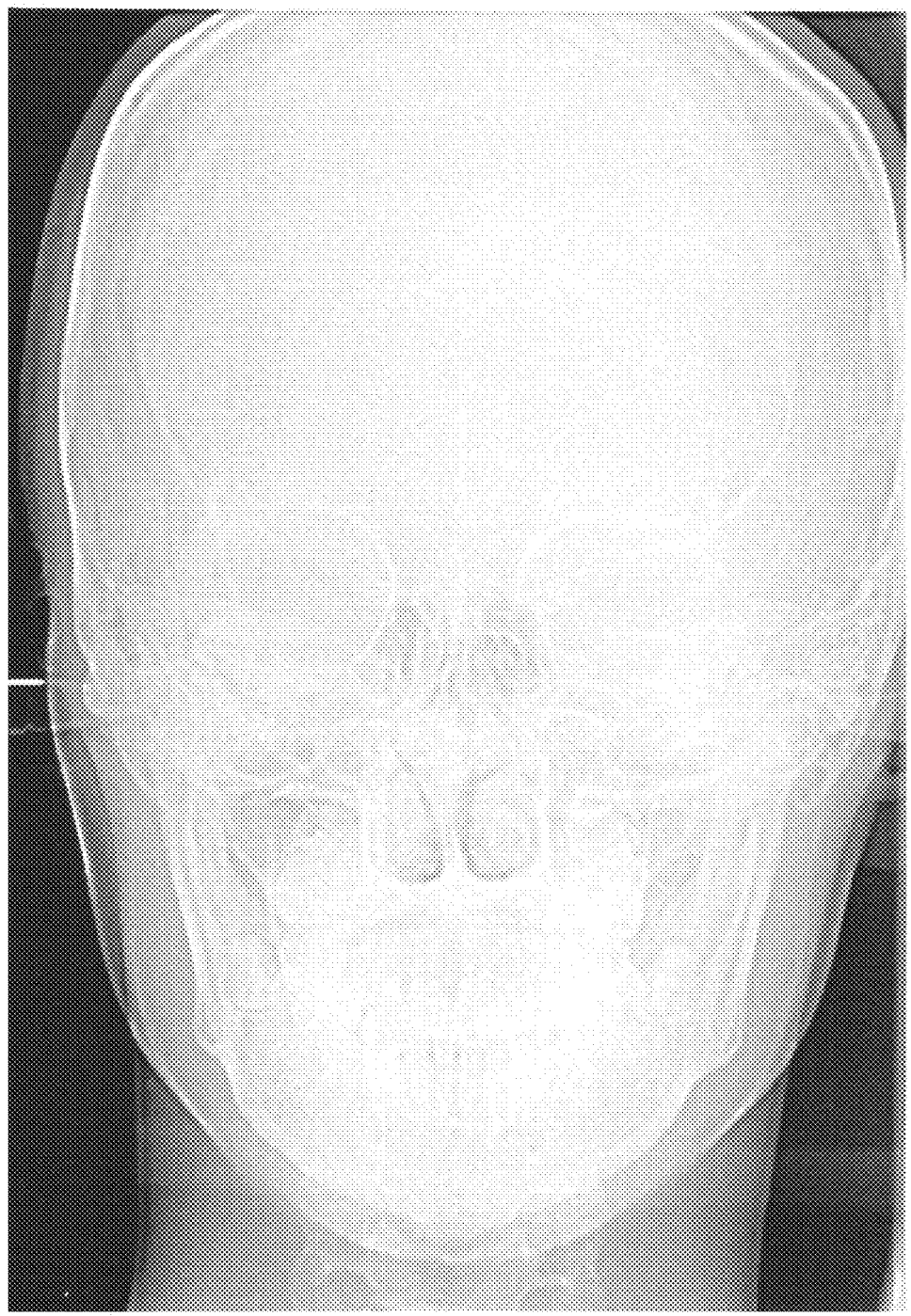
FIG. 46 A substitute picture for a drawing showing a posteroanterior cephalometric radiograph of the subject 16 taken by using the cephalometric X-ray radiographic apparatus according to the first embodiment of the present invention.
Figure 47:
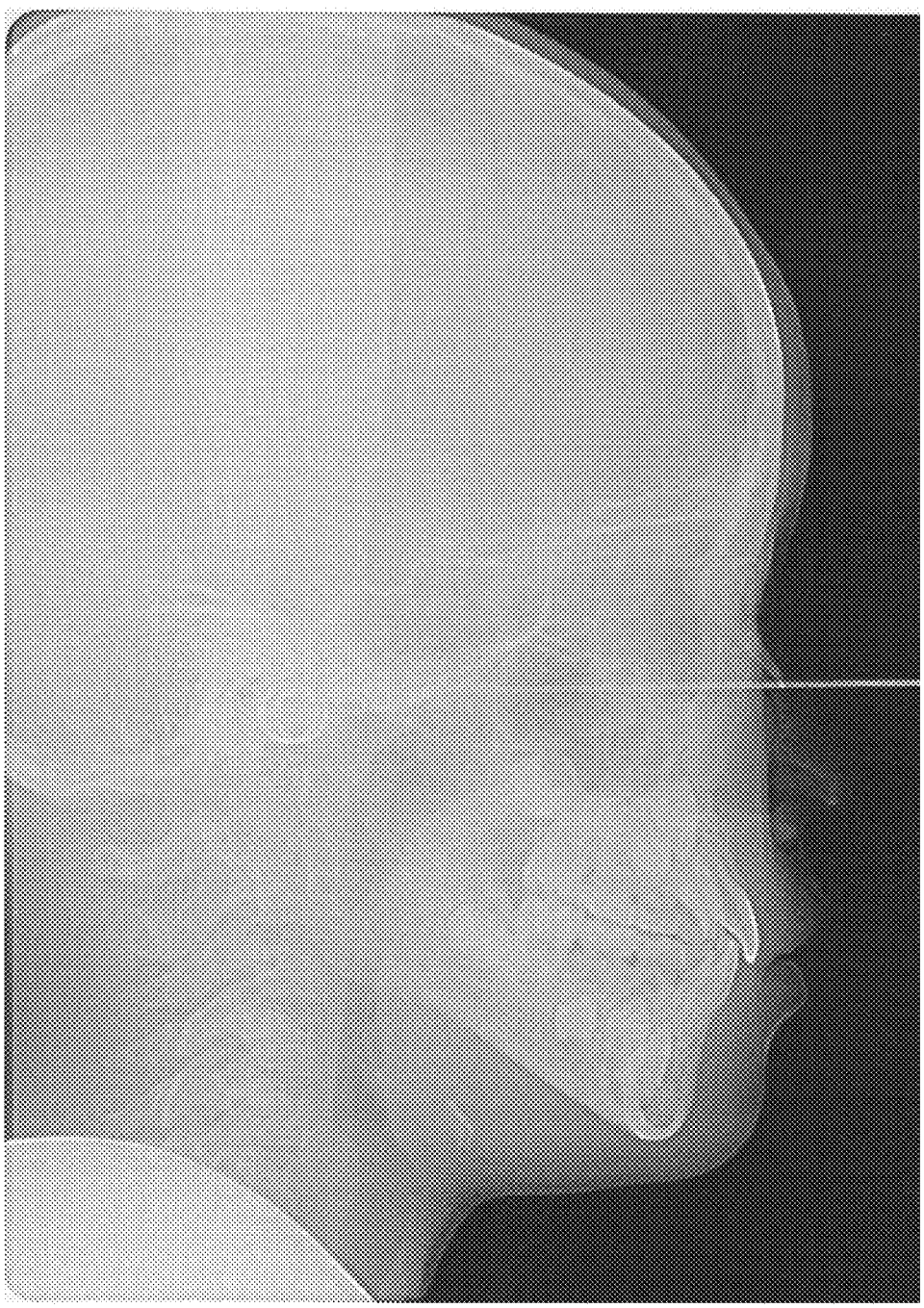
FIG. 47 A substitute picture for a drawing showing a lateral cephalometric radiograph of a subject 17 taken by using the cephalometric X-ray radiographic apparatus according to the first embodiment of the present invention.
Figure 48:
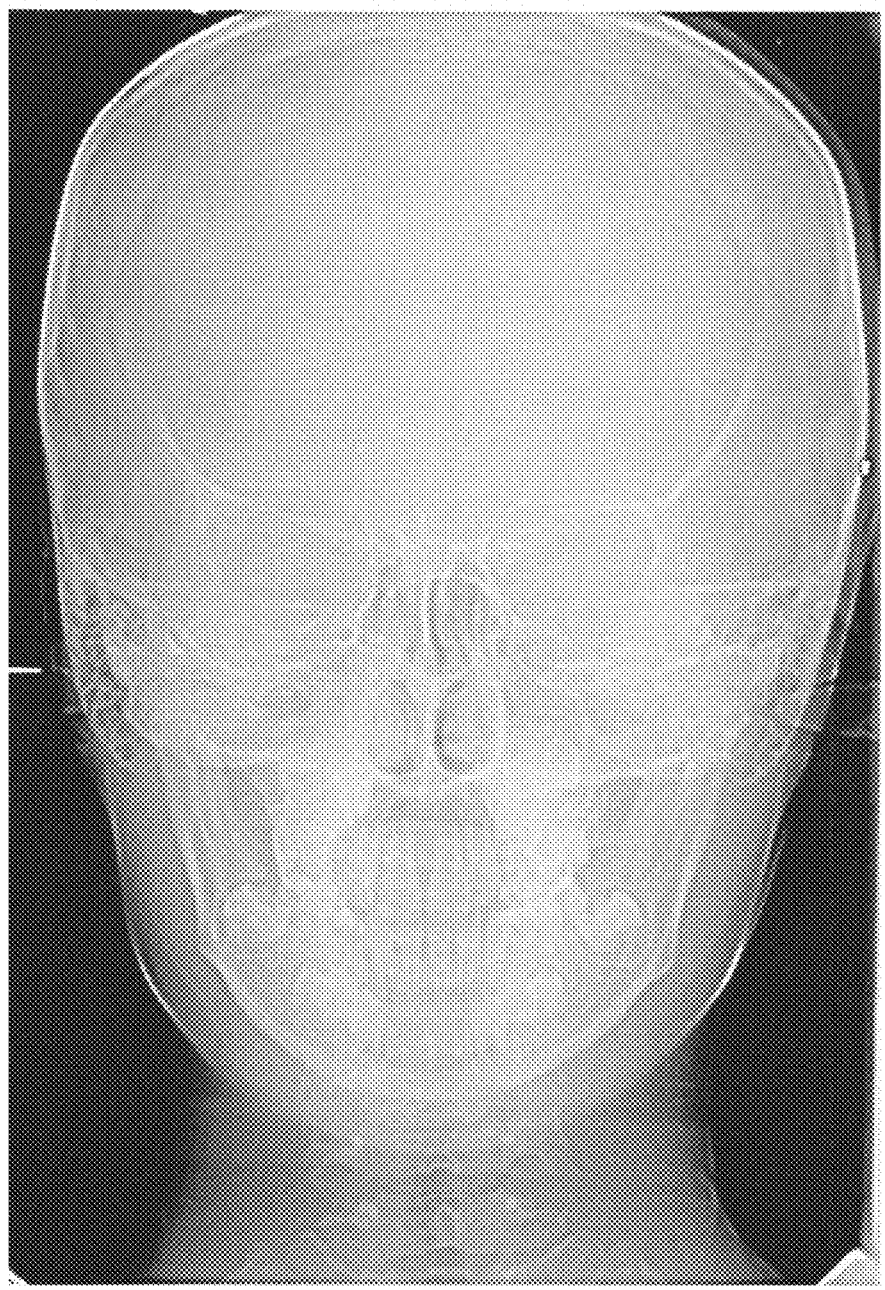
FIG. 48 A substitute picture for a drawing showing a posteroanterior cephalometric radiograph of the subject 17 taken by using the cephalometric X-ray radiographic apparatus according to the first embodiment of the present invention.
Figure 49:
FIG. 49 A substitute picture for a drawing showing a lateral cephalometric radiograph of a subject 18 taken by using the cephalometric X-ray radiographic apparatus according to the first embodiment of the present invention.
Figure 50:
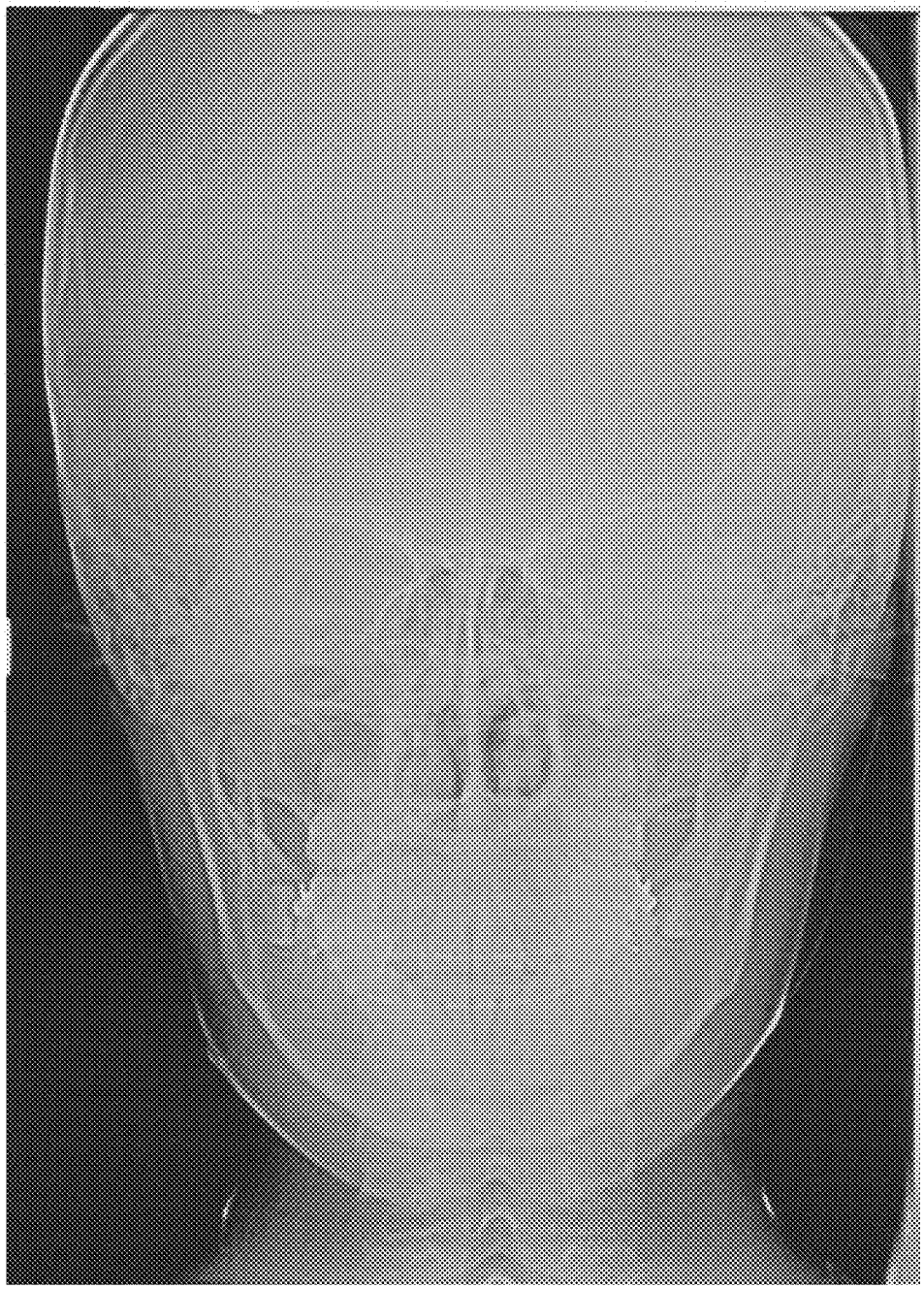
FIG. 50 A substitute picture for a drawing showing a posteroanterior cephalometric radiograph of the subject 18 taken by using the cephalometric X-ray radiographic apparatus according to the first embodiment of the present invention.

The details of the lower part of the arm tilt setting device 71 are shown in FIG. 14. FIG. 14 is a drawing looking at the lower part of the arm tilt setting device 71 provided to the edge of the upper part 13b of the arm 13 from the direction vertical to the plane of the lower part of the arm tilt setting device 71. As shown in FIG. 14, at the lower part of the arm tilt setting device 71, the angle scale 71a centered on the points $C_1$ and $C_2$ of the lower parts 12a and 13a of the arms 12 and 13 is formed, and has the function of a protractor. In FIG. 14, the angle scale 71a is formed from 0° to 90° marked every 10°, but the marking of the angle scale 71a is not limited to this, for example, may be marked every 5° or 1°, or only the angle in a specific range, for example, may be formed with an angle scale from 0° to 30°, for example. The line of a 0° of the angle scale 71a is a vertical line. The angle scale 71a is typically formed by a black colored line, for example, as the same as a general protractor, but is not limited to this. The angle scale 71a may be formed on one surface of the lower part of the arm tilt setting device 71, but is preferably formed respectively at the corresponding position on both surfaces each other. Like this, by forming the angle scale 71a at the corresponding position on the both surfaces of the lower part of the arm tilt setting device 71 each other, when looking at the angle scale 71*a* from the horizontal direction, the direction coinciding with the angle scale 71*a* of both surfaces is the horizontal direction, and if not coinciding, it can be judged to be different from the horizontal direction.

Other than those of the above constitution of the cephalometric X-ray radiographic apparatus is the same as the cephalometric X-ray radiographic apparatus according to the first embodiment.

Next, a method of taking a cephalometric radiograph of a subject using the cephalometric X-ray radiographic apparatus will be explained.

In FIG. 13, the arms 12 and 13 are made to move translatory outside in the horizontal direction, set apart at an enough distance each other, and move to a high enough position. Also, the arms 12 and 13 are made to rotate around the reference line 16 so that the inclination angle β (see FIG. 10) relative to the central X-ray of the central axis of the ear rods 17 and 18 becomes an intended angle. Under the state, as shown in FIG. 13, the head 21 of a subject is made to be positioned between the arms 12 and 13 so that the median sagittal plane is inclined at an angle γ (0°≤γ≤90°) relative to the central X-ray from the X-ray tube 11*a*. In this case, the median sagittal plane of the subject inclines relative to the floor surface. For this, in order to enable the head 21 to hold at the position, for example, the subject sits on a chair which is able to adjust the inclination angle of the sitting face relative to the floor surface, and the body is fixed by fastening a belt under the tilted state relative to the vertical line. In order to tilt the median sagittal plane of the head 21 of the subject to an angle γ relative to the central X-ray, a lower part of the arm tilt setting device 71 is used. That is, as shown in FIG. 14, using the angle scale 71*a* of the lower part of the arm tilt setting device 71, the lower parts 12*a* and 13*a* of the arms 12 and 13 are folded at an intended angle γ relative to the upper parts 12*b* and 13*b*. In FIG. 14, a case of γ=20° is shown. Under the state, by descending the arms 12 and 13 independently each other, the ear rods 17 and 18 are made to come to the height position of the right and left external acoustic openings of the head 21 of the subject. Next, the arms 12 and 13 are made to move translatory inside in the horizontal direction, the arms 12 and 13 are descended independently each other, the ear rods 17 and 18 are inserted in the right and left external acoustic openings of the head 21 of the subject, and by making the uppermost point of the ear rods 17 and 18 contact with the porion, the head 21 is fixed. The seal 21 is put on the predetermined reference point of the face of the head 21 in advance. Next, the inspector looks at the head tilt setting device 19 from the outside in the direction vertical to the head tilt setting device 19. At this time, the seal 21 also can be seen through the head tilt setting device 19. And, using the angle scale 19*a* of the head tilt setting device 19, the straight line connecting the porion with the orbitale is set at the intended angle α. And, by taking the radiograph at the position, a cephalometric radiograph can be taken.

According to the fourth embodiment, in addition to the inclination angle α in the front-rear direction of the head 21, by setting the angles β and γ respectively, a cephalometric radiograph can be taken from any direction, and by taking the cephalometric radiograph from plural directions different from each other, the cephalometric analysis can be performed three-dimensionally. Also, the cephalometric radiograph is taken from plural directions, and from the plural two-dimensional images taken like this, the three-dimensional image can be composed.

Example

By using the head tilt setting device 19, the lateral cephalometric radiographs and the posteroanterior cephalometric radiographs of the subjects 1 to 18 were taken at the position that the Frankfort plane of the head 21 is parallel to the floor surface. The radiographs were taken at the centric occlusal position or a position near to it. FIG. 15, FIG. 17, FIG. 19, FIG. 21, FIG. 23, FIG. 25, FIG. 27, FIG. 29, FIG. 31, FIG. 33, FIG. 35, FIG. 37, FIG. 39, FIG. 41, FIG. 43, FIG. 45, FIG. 47 and FIG. 49 show the lateral cephalometric radiograph of the subjects 1 to 18, respectively. Here, the lateral white lines seen in FIG. 15, FIG. 17, FIG. 19, FIG. 21, FIG. 23, FIG. 25, FIG. 27, FIG. 29, FIG. 31, FIG. 33, FIG. 35, FIG. 37, FIG. 39, FIG. 41, FIG. 43, FIG. 45, FIG. 47 and FIG. 49 are the images of the horizontal plate 20 provided at the bottom edge of the head tilt setting device 19, and show the Frankfort plane. Also, FIG. 16, FIG. 18, FIG. 20, FIG. 22, FIG. 24, FIG. 26, FIG. 28, FIG. 30, FIG. 32, FIG. 34, FIG. 36, FIG. 38, FIG. 40, FIG. 42, FIG. 44, FIG. 46, FIG. 48 and FIG. 50 show the posteroanterior cephalometric radiographs of the subjects 1 to 18, respectively.

Figure 51:
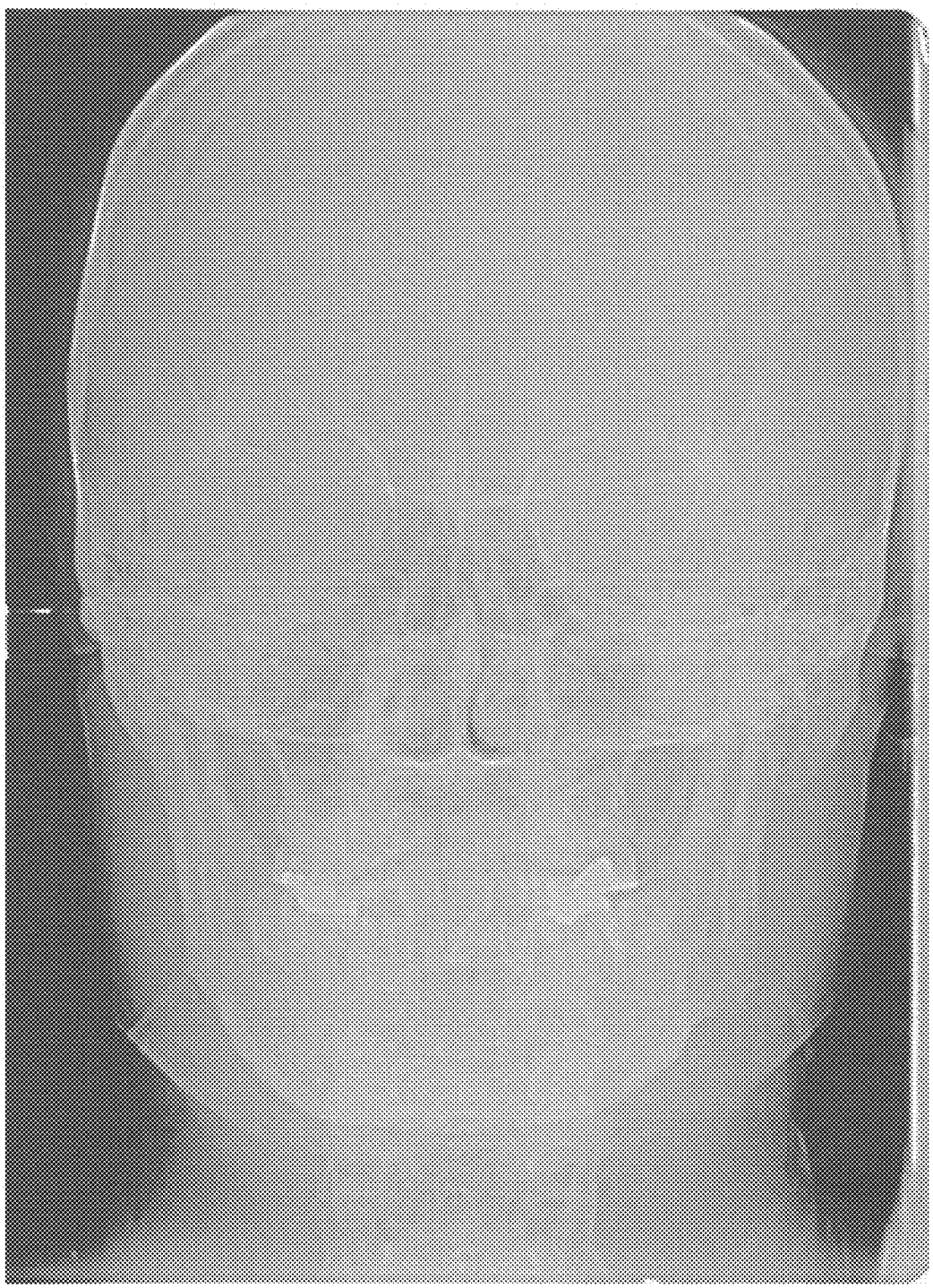
FIG. 51 A substitute picture for a drawing showing a posteroanterior cephalometric radiograph of a subject 19 taken by using the cephalometric X-ray radiographic apparatus according to the first embodiment of the present invention.
Figure 52:
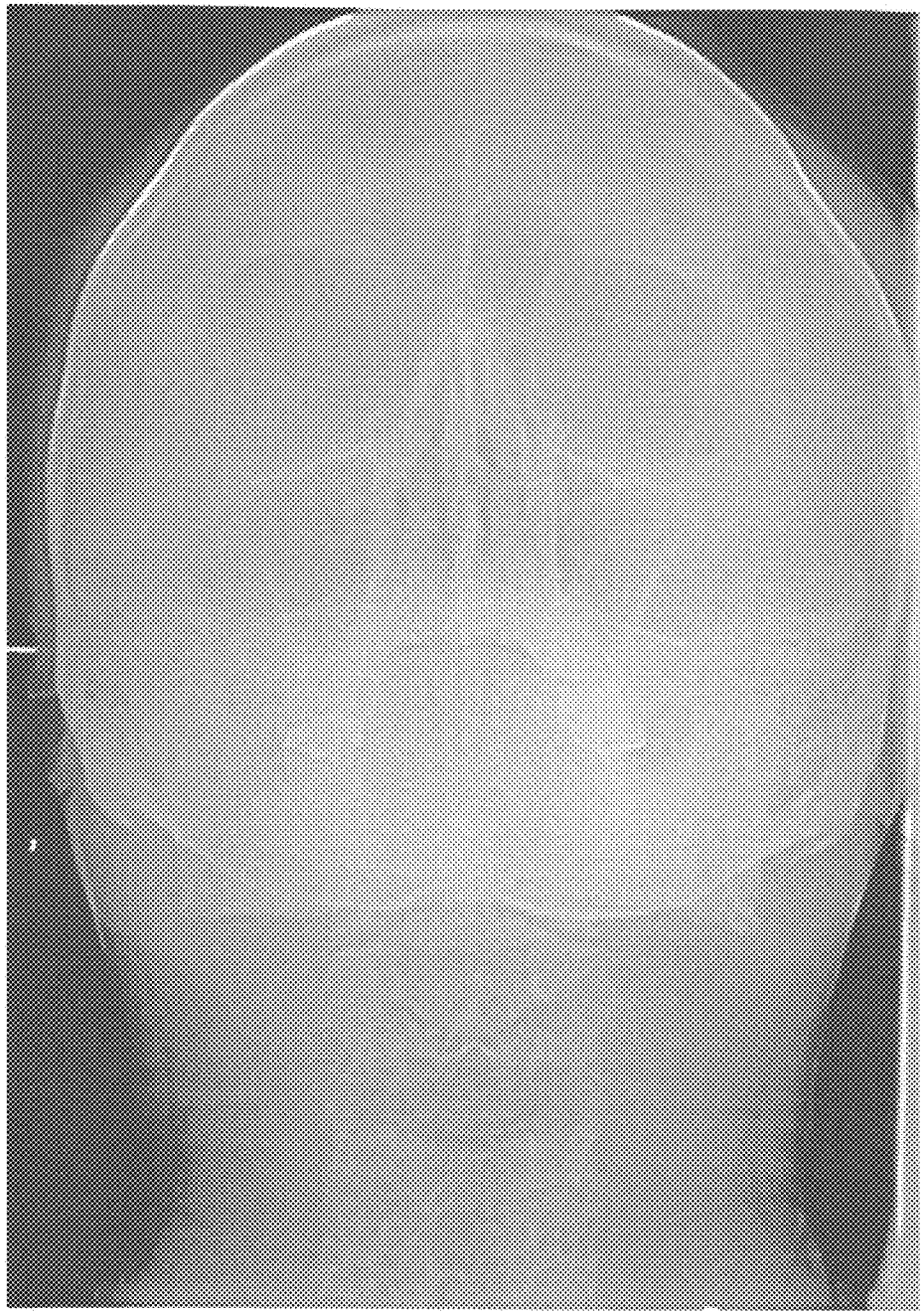
FIG. 52 A substitute picture for a drawing showing a posteroanterior cephalometric radiograph facing the face upward of the subject 19 taken by using the cephalometric X-ray radiographic apparatus according to the first embodiment of the present invention.
Figure 53:
FIG. 53 A substitute picture for a drawing showing a posteroanterior cephalometric radiograph facing the face downward of the subject 19 taken by using the cephalometric X-ray radiographic apparatus according to the first embodiment of the present invention.

FIG. 51 shows a posteroanterior cephalometric radiograph taken at the position that the Frankfort plane of the head 21 of a subject 19 is parallel to the floor surface. Also, FIG. 52 shows a posteroanterior cephalometric radiograph of the subject 19 taken, facing the face upward. Also, FIG. 53 shows a posteroanterior cephalometric radiograph of the subject 19 taken, facing the face downward.

From FIG. 15 to FIG. 50, of all of these subjects 1 to 18, it is known that the lateral cephalometric radiographs and the anteroposterior cephalometric radiographs can be taken at the position that the Frankfort plane of the head is parallel to the floor surface. Also, from FIG. 51 to FIG. 53, the posteroanterior cephalometric radiographs taken, facing the face upward and downward are quite different from the posteroanterior cephalometric radiograph taken at the position that the Frankfort plane of the head 21 is parallel to the floor surface in their impression.

5. The Fifth Embodiment

Figure 54:
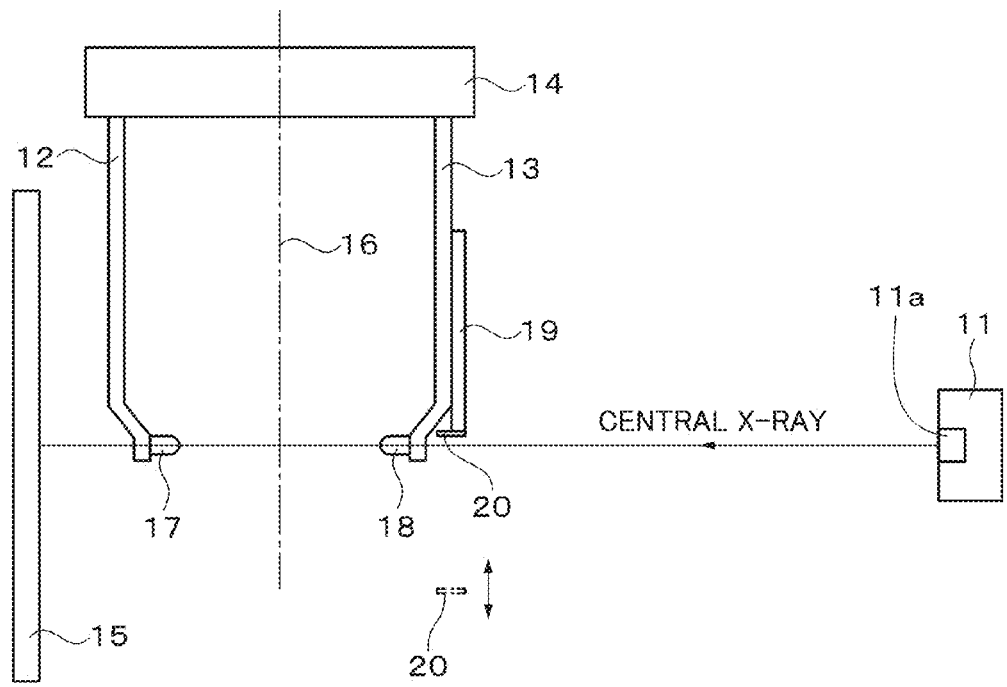
FIG. 54 A schematic drawing looking at a cephalometric X-ray radiographic apparatus according to the fifth embodiment of the present invention from the horizontal direction and the vertical direction to the central X-ray.

FIG. 54 shows the cephalometric X-ray radiographic apparatus according to the fifth embodiment. As shown in FIG. 54, in the cephalometric X-ray radiographic apparatus, the horizontal plate 20 contacts with the bottom edge surface of the head tilt setting device 19, under the state of protruding toward the inside, vertically to the head tilt setting device 19. The plan view of the present state head tilt setting device 19 and horizontal plate 20 are the same as FIG. 3. The horizontal plate 20 is constituted so as to be able to move up and down, or move in the horizontal plane, or carryout the both of them by a moving mechanism of which drawing is omitted. The moving mechanism can be set up at the arm 13, or on the floor surface, etc. The horizontal plate 20 is, for example, risen by the moving mechanism from the position just under the head tilt setting device 19 shown in a dot and dash line in FIG. 54, stopped at the time of contacting with the bottom edge surface of the head tilt setting device 19, and the state is kept held. For example, the horizontal plate 20 and the head tilt setting device 19 may be constituted so that the horizontal plate 20 engages to the bottom edge surface of the head tilt setting device 19 detachably at the time when the horizontal plate 20 contacts with the bottom edge surface. In this case, the moving mechanism can be descended after the horizontal plate 20 engages to the bottom edge surface of the head tilt setting device 19. Other than those of the above constitution of the cephalometric X-ray radiographic apparatus is the same as the first embodiment.

A method of taking a cephalometric radiograph of a subject using the cephalometric X-ray radiographic apparatus is the same as the first embodiment.

According to the fifth embodiment, the same advantages as the first embodiment can be obtained.

6. The Sixth Embodiment

Figure 55A:
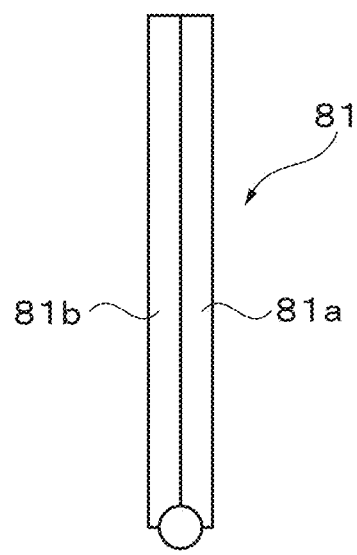
FIG. 55A A plan view showing a closed and open state of a foldable scale-like horizontal plate to be used as a horizontal plane verification mechanism in a cephalometric X-ray radiographic apparatus according to the sixth embodiment of the present invention.
Figure 55B:
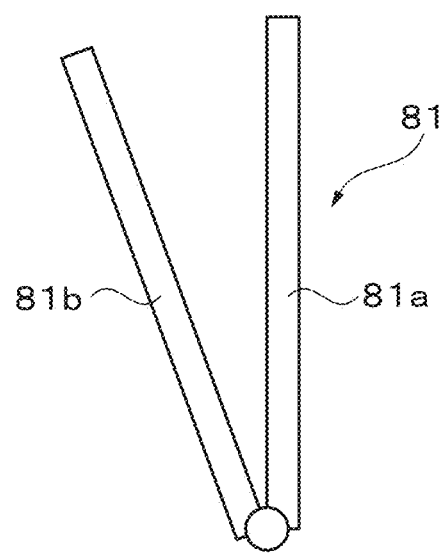
FIG. 55B A plan view showing a closed and open state of a foldable scale-like horizontal plate to be used as a horizontal plane verification mechanism in the cephalometric X-ray radiographic apparatus according to the sixth embodiment of the present invention.

FIG. 55A and FIG. 55B show a foldable scale-like horizontal plate 81 to be used as the horizontal plane verification mechanism in the cephalometric X-ray radiographic apparatus according to the sixth embodiment. Here, FIG. 55A shows the closed state of the foldable scale-like horizontal plate 81, and FIG. 55B shows the open state of the foldable scale-like horizontal plate 81. As shown in FIG. 55A and FIG. 55B, the foldable scale-like horizontal plate 81 has two long and thin strip parts 81a and 81b rotatable around the common shaft provided at one edge. As the same as the fifth embodiment, the foldable scale-like horizontal plate 81 is constituted so as to be able to move up and down or move in the horizontal plane, or carry out the both of them by a moving mechanism of which drawing is omitted. The foldable scale-like horizontal plate 81 is made to contact with the bottom edge surface of the head tilt setting device 19. In this time, for example, the longitudinal direction of the foldable scale-like horizontal plate 81 is set to be parallel to the head tilt setting device 19. The foldable scale-like horizontal plate 81 may be used to confirm the horizontal plane under the closed state as shown in FIG. 55A, or may be used to confirm the horizontal plane under the open state as shown in FIG. 55B. Also, for example, by rotating the strip part 81b outside relative to the strip part 81a under the state that the strip part 81a of the foldable scale-like horizontal plate 81 is made to contact with the bottom edge surface of the head tilt setting device 19, the front edge of the strip part 81b can be made approach to the face of the head 21 of the subject. By selecting the installation position of the foldable scale-like horizontal plate 81 relative to the head tilt setting device 19, the length of the foldable scale-like horizontal plate 81, the open angle of the foldable scale-like horizontal plate 81, etc., the front edge of the strip part 81b can be approached to the position near to the orbitale of the face of the head 21 of the subject, for example. By doing so, the tilt in the front-rear direction of the head 21 of the subject can be set correctly.

Other than those of the above constitution of the cephalometric X-ray radiographic apparatus is the same as the cephalometric X-ray radiographic apparatus according to the first embodiment. Also, a method of taking a cephalometric radiograph of a subject using the cephalometric X-ray radiographic apparatus is basically the same as the first embodiment.

According to the sixth embodiment, the same advantages as the first embodiment can be obtained.

7. The Seventh Embodiment

Figure 56:
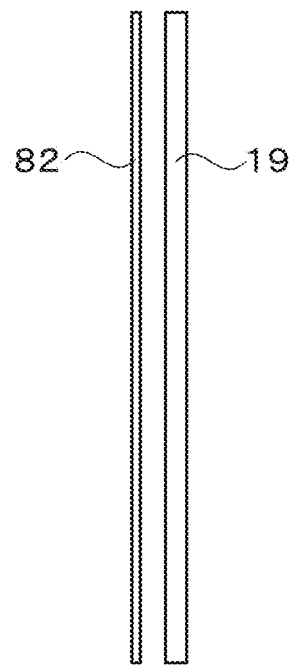
FIG. 56 A plan view showing a horizontal colored line to be used as a horizontal plane verification mechanism in a cephalometric X-ray radiographic apparatus according to the seventh embodiment of the present invention.

FIG. 56 shows a horizontal colored line 82 to be used as the horizontal plane verification mechanism in the cephalometric X-ray radiographic apparatus according to the seventh embodiment. The colored line 82 is typically provided parallel to the head tilt setting device 19, but may be provided diagonally relative to the head tilt setting device 19. The colored line 82 may be a thin linear wire having a diameter of its cross section of 0.5 mm and more and 2 mm and less, for example, made of metal such as steel, etc., carbon fiber, plastics, etc. of which surface is colored, or a linear transparent fiber made of glass or plastics, etc., colored by making a visible light such as a red light, a green light, etc. (a laser beam or a light from a light-emitting diode) wave guide from the edge surface. A visible light beam itself may be used. In this case, by using the colored line 82 instead of the horizontal plate 20, the horizontal plane can be confirmed.

Other than those of the above constitution of the cephalometric X-ray radiographic apparatus is the same as the cephalometric X-ray radiographic apparatus according to the first embodiment. Also, a method of taking a cephalometric radiograph of a subject using the cephalometric X-ray radiographic apparatus is basically the same as the first embodiment.

According to the seventh embodiment, the same advantages as the first embodiment can be obtained.

8. The Eighth Embodiment

FIG. 57 shows an optical device 83 to be used as the horizontal plane verification mechanism in the cephalometric X-ray radiographic apparatus according to the eighth embodiment. The optical device 83 includes a light source and a scanning mechanism which are able to irradiate or scan a visible light beam 85 in the horizontal plane. The visible light beam 85 is a laser beam or a beam-like light which is made from the light emitted from a light-emitting diode. As the visible light beam 85, for example, a red light beam, a green light beam, etc. is used. Around the optical device 83, an X-ray shielding cover 84 made of X-ray shielding materials such as lead, etc. to protect the optical device 83 from the incident X-ray is provided. The X-ray shielding cover 84 is appropriately designed so that the optical device 83 can be shielded from the incident X-ray in consideration of the X-ray incident direction. In this case, by using the visible light beam 85 instead of the horizontal plate 20, the horizontal plane can be confirmed. For example, when looking at the head tilt setting device 19 from the outside in the horizontal direction, the horizontal line corresponding to the angle 0° of the head tilt setting device 19 and the visible light beam 85 coincide with each other. At this time, the visible light beam 85 is irradiated or scanned on the face side of the head 21 of the subject. And if it is possible to confirm visually that the front edge of the visible light beam 85 coincides with the orbitale, the Frankfort plane of the head 21 can be judged as parallel to the floor surface. In this case, the seal 22 is not necessarily put on the face.

Other than those of the above constitution of the cephalometric X-ray radiographic apparatus is the same as the cephalometric X-ray radiographic apparatus according to the first embodiment. Also, a method of taking a cephalometric radiograph of a subject using the cephalometric X-ray radiographic apparatus is basically the same as the first embodiment.

According to the eighth embodiment, the same advantages as the first embodiment can be obtained.

9. The Ninth Embodiment

Figure 58A:
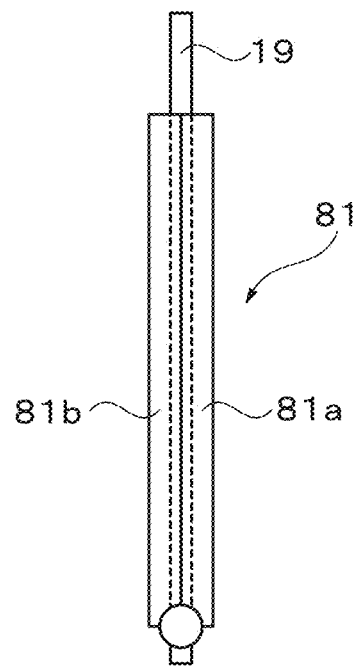
FIG. 58A A plan view looking at a closed and open state of a foldable scale-like horizontal plate as a horizontal plane verification mechanism provided on the bottom surface of the head tilt setting device from the underside in a cephalometric X-ray radiographic apparatus according to the ninth embodiment of the present invention.
Figure 58B:
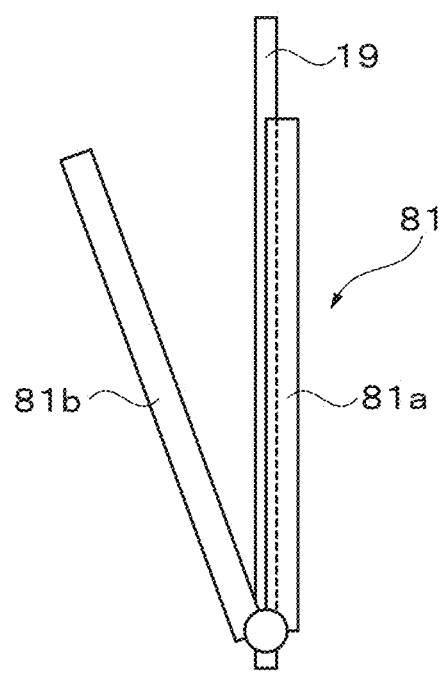
FIG. 58B A plan view looking at a closed and open state of a foldable scale-like horizontal plate as a horizontal plane verification mechanism provided on the bottom surface of the head tilt setting device from the underside in the cephalometric X-ray radiographic apparatus according to the ninth embodiment of the present invention.

FIG. 58A and FIG. 58B show drawings looking at a foldable scale-like horizontal plate 81 to be used as the horizontal plane verification mechanism in the cephalometric X-ray radiographic apparatus according to the ninth embodiment from the bottom surface of the head tilt setting device 19. Here, FIG. 58A shows the closed state of the foldable scale-like horizontal plate 81, and FIG. 58B shows the open state of the foldable scale-like horizontal plate 81. As shown in FIG. 58A and FIG. 58B, the foldable scale-like horizontal plate 81 has two thin and long strip parts 81a and 81b rotatable around the common shaft provided on the one edge. The strip part 81a of the foldable scale-like horizontal plate 81 is fixed on the bottom edge surface of the head tilt setting device 19, parallel to the head tilt setting device 19 by a method of adhesion, etc. The foldable scale-like horizontal plate 81 may be used to confirm the horizontal plane under the closed state shown in FIG. 58A or may be used to confirm the horizontal plane under the open state shown in FIG. 58B. Also, for example, by rotating the strip part 81b of the foldable scale-like horizontal plate 81 outside relative to the strip part 81a, the front edge of the strip part 81b can be approached to the face of the head 21 of the subject. By selecting the installation position of the foldable scale-like horizontal plate 81 for the head tilt setting device 19, the length of the foldable scale-like horizontal plate 81, and the open angle of the foldable scale-like horizontal plate 81, etc., the front edge of the strip part 81b can be approached to a position near to the orbitale, for example, of the face of the head 21 of the subject. By doing this, the tilt in the front-rear direction of the head 21 of the subject can be set correctly.

Other than those of the above constitution of the cephalometric X-ray radiographic apparatus is the same as the cephalometric X-ray radiographic apparatus according to the first embodiment. Also, a method of taking a cephalometric radiograph of a subject using the cephalometric X-ray radiographic apparatus is basically the same as the first embodiment.

According to the ninth embodiment, the same advantages as the first embodiment can be obtained.

10. The Tenth Embodiment

Figure 59:
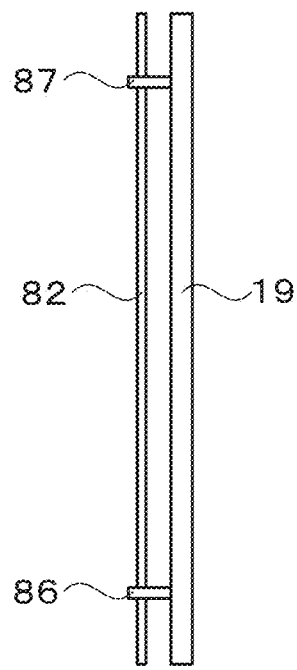
FIG. 59 A plan view showing a horizontal colored line as a horizontal plane verification mechanism provided parallel to the head tilt setting device in a cephalometric X-ray radiographic apparatus according to the tenth embodiment of the present invention.

FIG. 59 shows a horizontal colored line 82 to be used as the horizontal plane verification mechanism in the cephalometric X-ray radiographic apparatus according to the tenth embodiment. The colored line 82 is held by the supports 86 and 87 to one side surface of the head tilt setting device 19. The colored line 82 is typically provided parallel to the head tilt setting device 19, but may be provided diagonally for the head tilt setting device 19. As the colored line 82, for example, a thin linear wire having a diameter of its cross section of 0.5 mm and more and 2 mm or less, made of, for example, metal such as steel, etc., carbon fiber, plastics, etc. of which surface is colored, or a linear transparent fiber made of glass, plastics, etc. which is colored by making a visible light such as a red light, a green light, etc. (a laser beam or a light emitted from a light-emitting diode) wave guide from the edge surface is used. In this case, by using the colored line 82 instead of the horizontal plate 20, the horizontal plane can be confirmed.

Other than those of the above constitution of the cephalometric X-ray radiographic apparatus is the same as the cephalometric X-ray radiographic apparatus according to the first embodiment. Also, a method of taking a cephalometric radiograph of a subject using the cephalometric X-ray radiographic apparatus is basically the same as the first embodiment.

According to the tenth embodiment, the same advantages as the first embodiment can be obtained.

11. The Eleventh Embodiment

Figure 60:
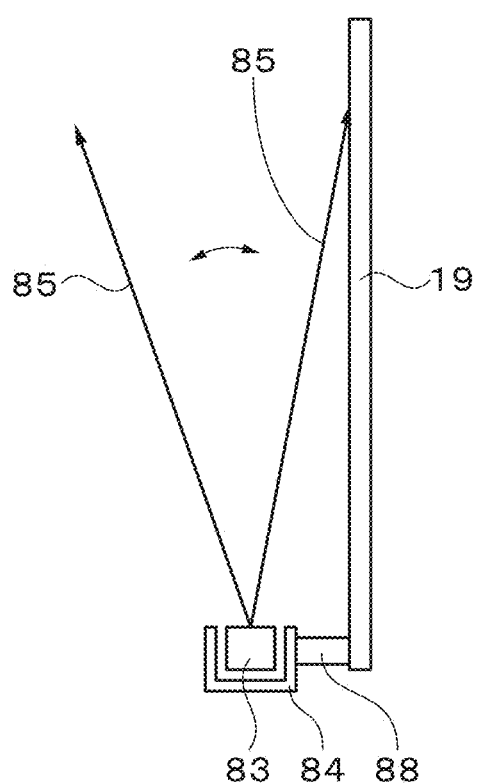
FIG. 60 A plan view showing an optical device as a horizontal plane verification mechanism provided at the head tilt setting device in a cephalometric X-ray radiographic apparatus according to the eleventh embodiment of the present invention.

FIG. 60 shows an optical device 83 to be used as the horizontal plane verification mechanism in the cephalometric X-ray radiographic apparatus according to the eleventh embodiment. The optical device 83 includes a light source and a scanning mechanism which are able to irradiate or scan a visible light beam 85 in the horizontal plane. The visible light beam 85 is a laser beam or a beam-like light which is made from the light emitted from a light-emitting diode. As the visible light beam 85, for example, a red light beam, a green light beam, etc. is used. Around the optical device 83, an X-ray shielding cover 84 made of X-ray shielding materials such as lead, etc. to protect the optical device 83 from the incident X-ray is provided. The X-ray shielding cover 84 is fixed on the side surface of the head tilt setting device 19 by the support 88. The X-ray shielding cover 84 is appropriately designed so as to be able to shield the optical device 83 from the incident X-ray in consideration of the X-ray incident direction. In this case, by using the visible light beam 85 instead of the horizontal plate 20, the horizontal plane can be confirmed. For example, when looking at the head tilt setting device 19 from the outside in the horizontal direction, the horizontal line corresponding to the angle 0° of the head tilt setting device 19 and the visible light beam 85 coincide with each other. At this time, the visible light beam 85 is irradiated or scanned on the face side of the head 21 of a subject. And if it is possible to confirm visually that the front edge of the visible light beam 85 coincides with the orbitale, it can be judged that the Frankfort plane of the head 21 is parallel to the floor surface. In this case, the seal 22 is not necessary put on the face.

Other than those of the above constitution of the cephalometric X-ray radiographic apparatus is the same as the cephalometric X-ray radiographic apparatus according to the first embodiment. Also, a method of taking a cephalometric radiograph of a subject using the cephalometric X-ray radiographic apparatus is basically the same as the first embodiment.

According to the eleventh embodiment, the same advantages as the first embodiment can be obtained.

12. The Twelfth Embodiment

Figure 61:
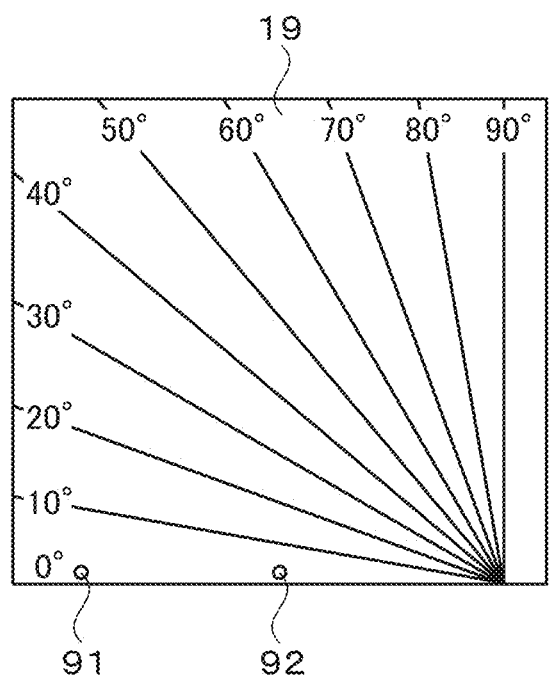
FIG. 61 A side view showing the head tilt setting device provided with a scale showing a length to be used in a cephalometric X-ray radiographic apparatus according to the twelfth embodiment of the present invention.

FIG. 61 shows the head tilt setting device 19 to be used in the cephalometric X-ray radiographic apparatus according to the twelfth embodiment. As shown in FIG. 61, the marks 91 and 92 made of X-ray shielding materials such as lead, steel, etc. are provided on the side surface of the head tilt setting device 19. The position of the marks 91 and 92 is basically arbitrarily. In order to enhance the contrast of the marks 91 and 92 on the image obtained by X-ray radiography, preferably, the images of the marks 91 and 92 are made to come to the outside region of the head 21 of a subject, but is not limit to this. In FIG. 61, the marks 91 and 92 are provided on the side surface of the bottom edge part of the head tilt setting device 19, in this case, the straight line connecting the center of the mark 91 with the center of the mark 92 is parallel to the bottom edge surface of the head tilt setting device 19. The scale showing the distance between the center of the mark 91 and the center of the mark 92, that is, the length is properly selected, but, for example, is 5 cm or 10 cm. When detecting the marks 91 and 92 by computer processing on the image obtained by X-ray radiography, preferably the marks 91 and 92 are formed so as to be detected the images of the marks 91 and 92 with a double lined outline. The marks 91 and 92 may be provided on the transparent plate constituting the head tilt setting device 19, may be buried in the transparent plate, or may be provided passing through the transparent plate. The shapes of the marks 91 and 92, when looking at the head tilt setting device 19 from the side surface, may be basically any shape, and is selected as necessary, specifically, for example, circle, triangle, square, hexagon, etc.

Other than those of the above constitution of the cephalometric X-ray radiographic apparatus is the same as the cephalometric X-ray radiographic apparatus according to the first embodiment. Also, a method of taking a cephalometric radiograph of a subject using the cephalometric X-ray radiographic apparatus is basically the same as the first embodiment.

According to the twelfth embodiment, the same advantages as the first embodiment can be obtained. In addition, the following advantages can be obtained. That is, the marks 91 and 92 made of X-ray shielding materials are provided on the head tilt setting device 19, and a scale showing the length by these marks 91 and 92 is provided. For this, when taking a radiograph of the head 21, in the transmission X-ray image to be detected by the X-ray detector 15, in addition to the image of the head 21, the images of the marks 91 and 92 21 are taken, therefore the scale showing the length is displayed on the image. In this case, the center-to-center distance of the images of the marks 91 and 92 on the transmission X-ray image is enlarged compared with the center-to-center distance of the marks 91 and 92 on the head tilt setting device 19. The enlargement factor M is M=(the distance between the X-ray tube 11a and the detection plane of the X-ray detector 15 on the central X-ray)/(the distance between the X-ray tube 11a and the marks 91 and 92 of the head tilt setting device 19 on the central X-ray). The enlargement factor m on the median sagittal plane of the head 21 is m=M×[(the distance between the X-ray tube 11a and the detection plane of the X-ray detector 15 on the central X-ray)/(the distance between the X-ray tube 11a and the median sagittal plane of the head 21 on the central X-ray)]. By using the equation, from the enlargement factor on the transmission X-ray image, the actual distance on the median sagittal plane of the head 21 can be obtained.

13. The Thirteenth Embodiment

Figure 62:
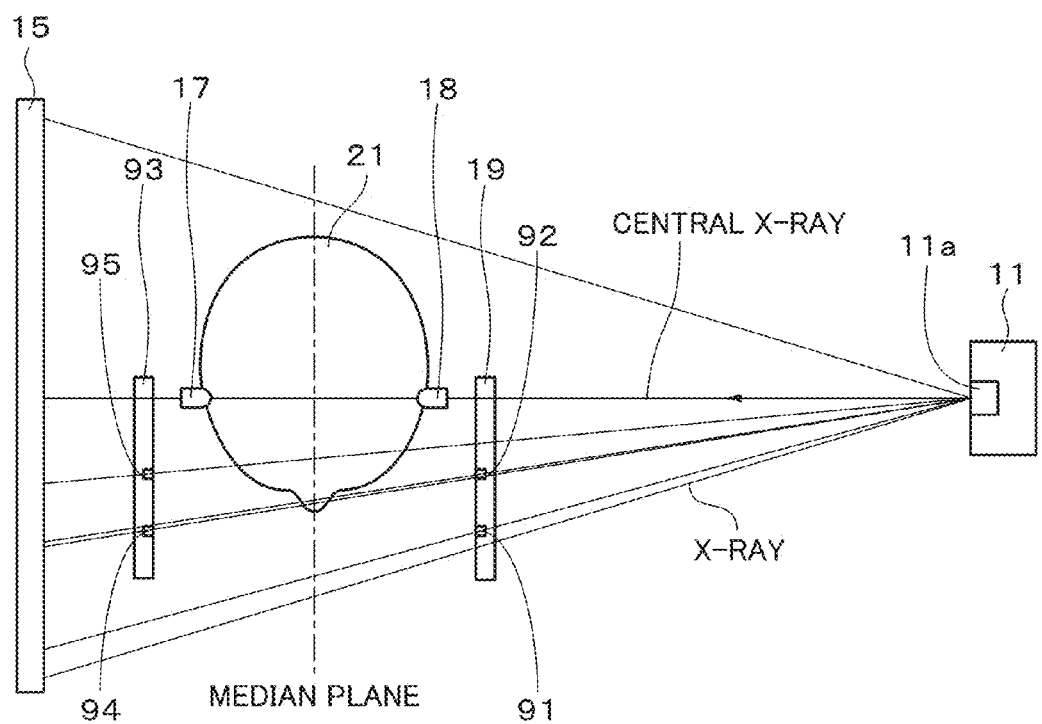
FIG. 62 A schematic drawing showing a cephalometric X-ray radiographic apparatus according to the thirteenth embodiment of the present invention.
Figure 63:
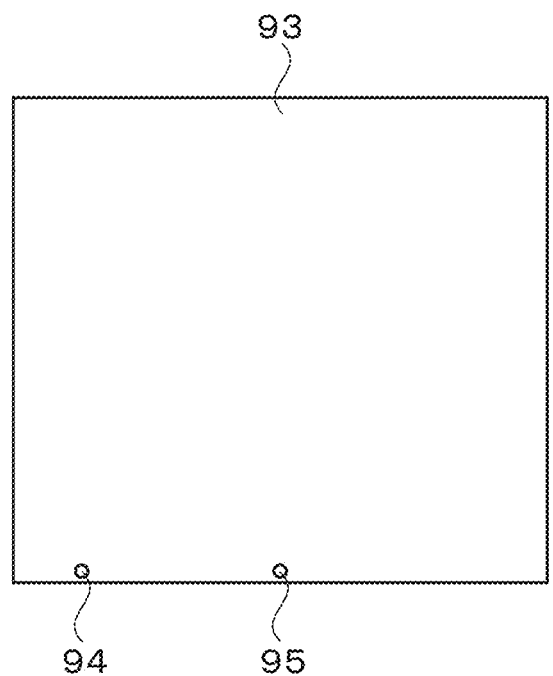
FIG. 63 A side view showing a transparent plate provided with a scale showing a length to be provided on the exterior surface of the other arm which is different from the arm provided with the head tilt setting device in the cephalometric X-ray radiographic apparatus according to the thirteenth embodiment of the present invention.

FIG. 62 shows the cephalometric X-ray radiographic apparatus according to the thirteenth embodiment. As shown in FIG. 62, in the cephalometric X-ray radiographic apparatus, in addition to the constitution of the cephalometric X-ray radiographic apparatus according to the first embodiment, a transparent plate 93 is provided on the outside surface of the arm 12 of which drawing is omitted. The transparent plate 93 is shown in FIG. 63. As shown in FIG. 63, as the same as the head tilt setting device 19 according to the twelfth embodiment, the marks 94 and 95 are provided at the transparent plate 93. These marks 94 and 95 can be provided at the same position and with the same constitution as the marks 91 and 92.

Figure 64:
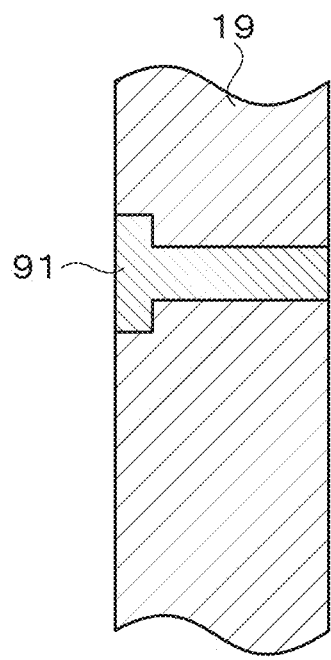
FIG. 64 A cross-sectional drawing showing a major part of the head tilt setting device in the cephalometric X-ray radiographic apparatus according to the thirteenth embodiment of the present invention.

An example of providing with the marks 91 and 92 piercing through in the thickness direction of the head tilt setting device 19 is shown in FIG. 64. As shown in FIG. 64, the mark 91 has a shape of a nail or a rivet, and is pierced through in the thickness direction of the head tilt setting device 19.

Other than those of the above constitution of the cephalometric X-ray radiographic apparatus is the same as the cephalometric X-ray radiographic apparatus according to the first embodiment. Also, a method of taking a cephalometric radiograph of a subject using the cephalometric X-ray radiographic apparatus is basically the same as the first embodiment.

According to the thirteen embodiment, the same advantages as the first embodiment can be obtained. In addition, the following advantages can be obtained. That is, the marks 91 and 92 made of X-ray shielding materials are provided on the head tilt setting device 19 provided on the outside surface of the arm 13, and a scale showing the length by these marks 91 and 92 is provided. Also, the marks 94 and 95 made of X-ray shielding materials are provided on the transparent plate 93 provided on the outside surface of the arm 12, and a scale showing the length by these marks 94 and 95 is provided. For this, when taking the cephalometric radiograph of the head 21, in the transmission X-ray image to be detected by the X-ray detector 15, in addition to the image of the head 21, the images of the marks 91 and 92 and the marks 94 and 95 are also taken. In this case, the center-to-center distance of the marks 91 and 92 on the transmission X-ray image is enlarged compared with the center-to-center distance of the marks 91 and 92 on the head tilt setting device 19. The enlargement factor $M_1$ is $M_1$=(the distance between the X-ray tube 11a and the detection plane of the X-ray detector 15 on the central X-ray)/(the distance between the X-ray tube 11a and the marks 91 and 92 of the head tilt setting device 19 on the central X-ray). Also, the center-to-center distance of the images of the marks 94 and 95 on the transmission X-ray image is enlarged compared with the center-to-center distance of the marks 94 and 95 on the transparent plate 93. The enlargement factor $M_2$ is $M_2$=(the distance between the X-ray tube 11a and the detection plane of the X-ray detector 15 on the central X-ray)/(the distance between the X-ray tube 11a and the marks 94 and 95 of the transparent plate 93 on the central X-ray). The enlargement factor m on the median sagittal plane of the head 21 is m=$(M_1+M_2)/2$. Using the equation, from the enlargement factor on the transmission X-ray image, the actual distance on the median sagittal plane of the head 21 can be obtained.

Example

Figure 65:
FIG. 65 A substitute picture for a drawing showing a lateral cephalometric radiograph of a subject 20 taken by using the cephalometric X-ray radiographic apparatus according to the twelfth embodiment of the present invention.
Figure 66:
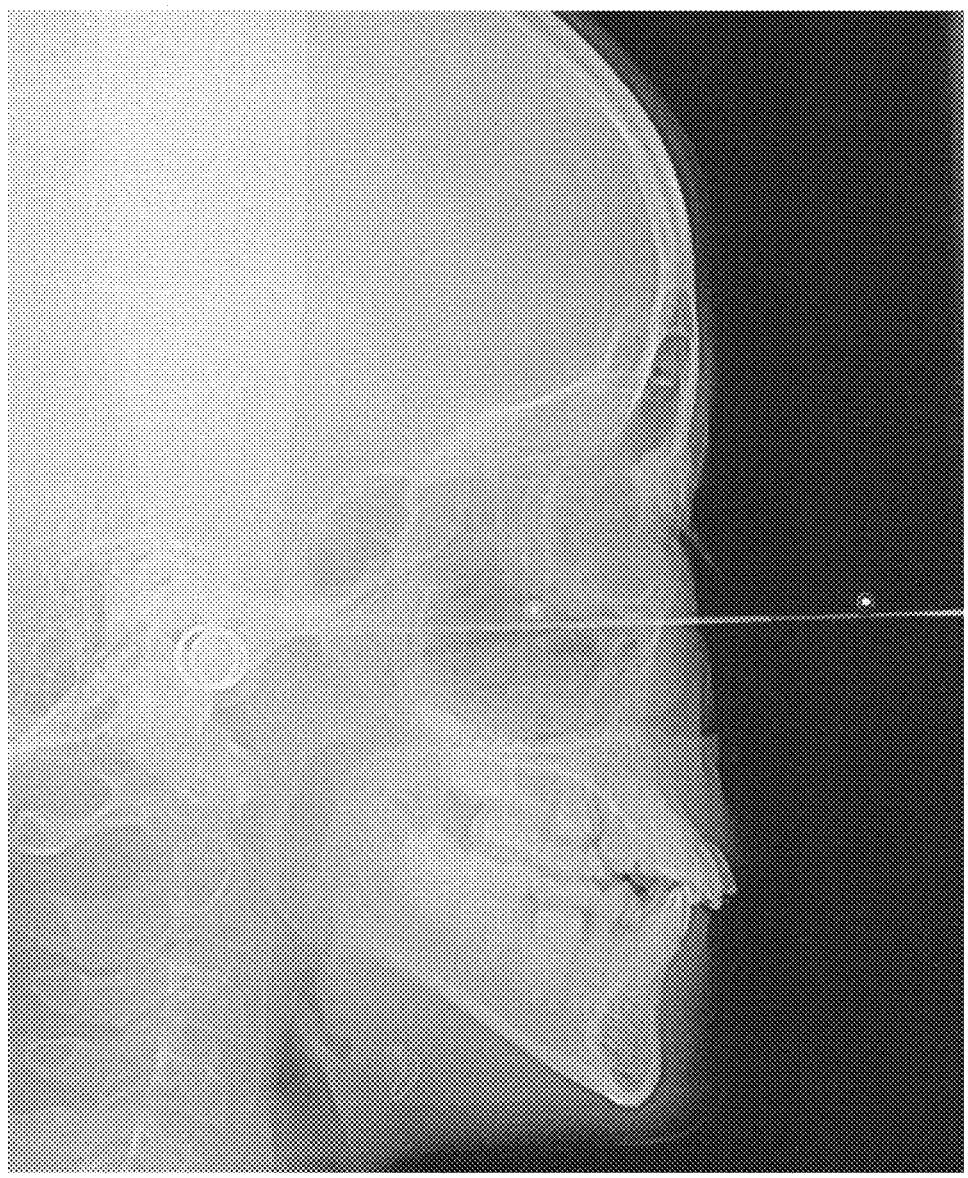
FIG. 66 A substitute picture for a drawing showing a lateral cephalometric radiograph of a subject 21 taken by using the cephalometric X-ray radiographic apparatus according to the twelfth embodiment of the present invention.
Figure 67:
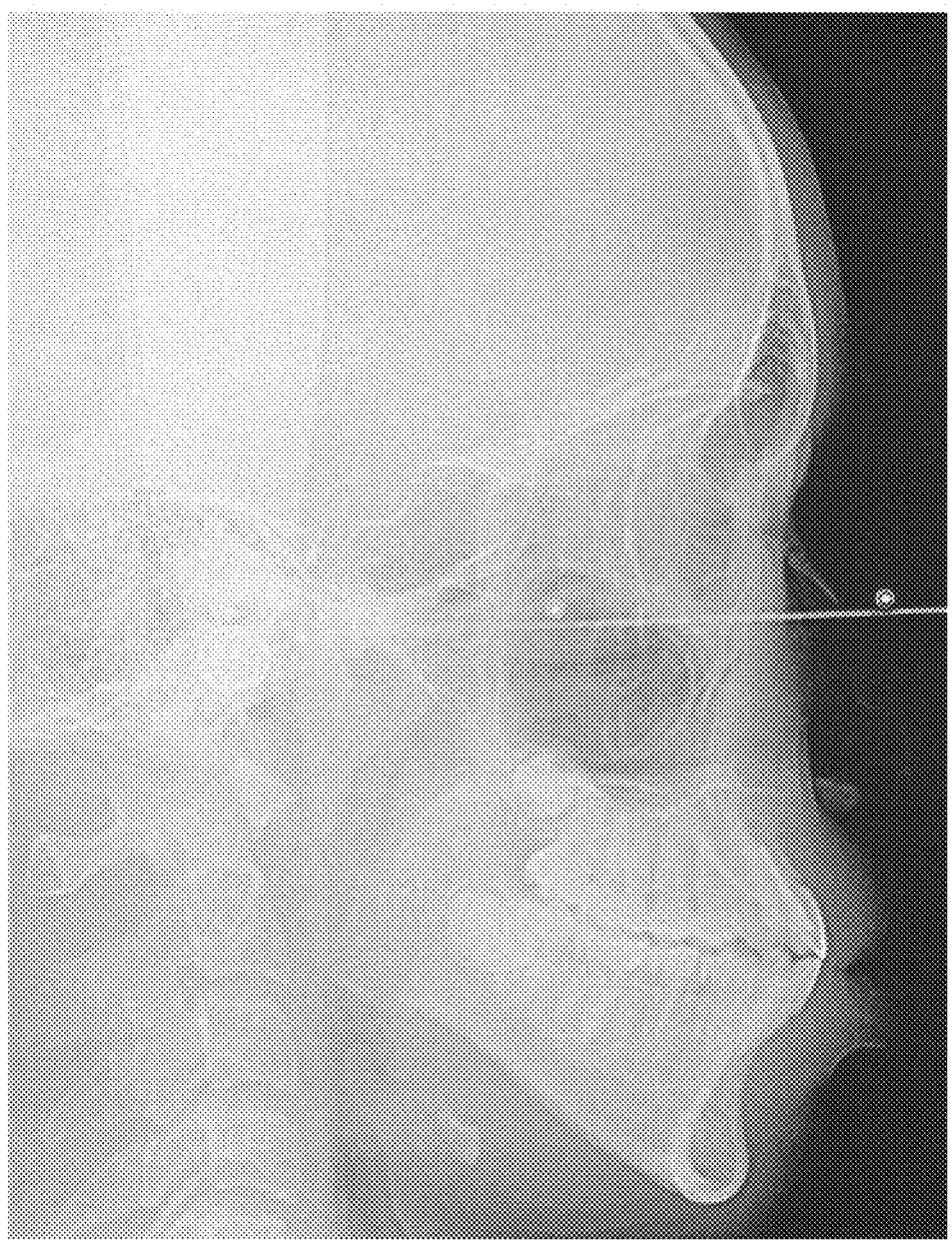
FIG. 67 A substitute picture for a drawing showing a lateral cephalometric radiograph of a subject 22 taken by using the cephalometric X-ray radiographic apparatus according to the twelfth embodiment of the present invention.

By using the head tilt setting device 19, the lateral cephalometric radiographs of subjects 20 to 22 were taken at the position that the Frankfort plane of the head 21 is parallel to the floor surface. Here, as the head tilt setting device 19, the head tilt setting device 19 provided with the marks 91 and 92 and with a scale showing the length which was used in the twelfth embodiment was used. As the marks 91 and 92, commercially available nails made of steel of which front edge was cut off were used, which were buried in the transparent plate made of acrylic. The radiographs were taken at the centric occlusal position or a position near to it. FIG. 65 to FIG. 67 show the lateral cephalometric radiographs of the subjects 20 to 22, respectively. Here, the lateral white lines seen in FIG. 65 to FIG. 67 are the images of the transparent plate 20 provided at the bottom edge of the head tilt setting device 19, and show the Frankfort plane. Also, in FIG. 65 to FIG. 67, the images of the marks 91 and 92 are observed as a double circle. Only using the commercially available nail made of steel of which front edge is cut off as the marks 91 and 92 like this, the double circle image can be obtained easily.

14. The Fourteenth Embodiment

In the first embodiment, as shown in FIG. 5, when the inspector has difficulty in looking at the seal 22 put on the predetermined reference point (the second reference point) of the face of the head 21, for example, on the orbitale from the lateral side of the head 21, it is explained that there is a case where the seal 22 is also put on the position apart from, for example, 5 to 20 mm outside in the horizontal direction from the seal 22 on the face. In the fourteenth embodiment, a method of putting the seal 22 at the position in the horizontal direction from the seal 22 put on the orbitale with high dimensional accuracy will be explained.

Figure 68:
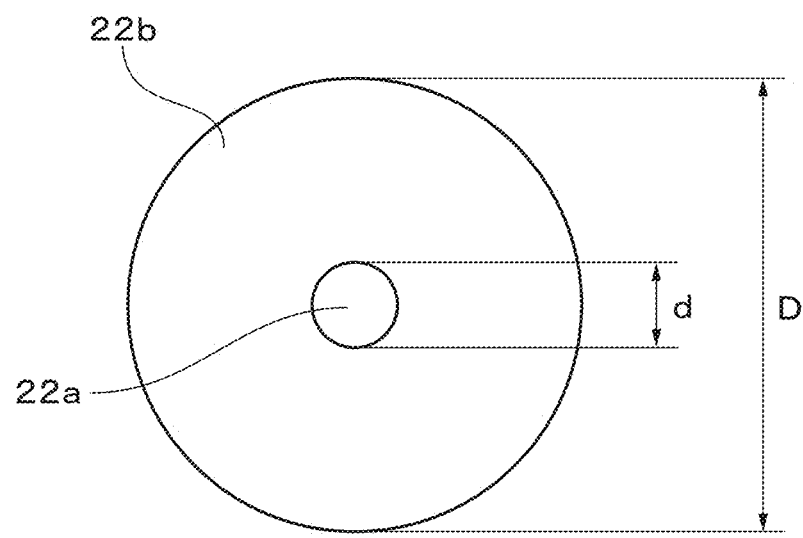
FIG. 68 A plan view showing a seal to be used in the fourteenth embodiment of the present invention.

First, as shown in FIG. 68, as the seal 22, the circular seal 22 composed of a small circular area 22a in the center and a ring-like area 22b surrounding the area 22a is used. The diameter d of the area 22a and the diameter of the outer shape (the diameter of the outer shape of the seal 22) D are selected so that the inspector can make visual confirmation of the seal 22 and the center area 22a easily. Specifically, for example, d is selected to be 1 mm and more and 2 mm and less (for example, 1.5 mm), and D is selected to be 5 mm and more and 9 mm and less (for example, 6.5 mm), but is not limited to them. Also, the colors of the area 22a and the area 22b are selected so that the inspector can make visual confirmation of the seal 22 and the center area 22a easily. Specifically, for example, white is selected for the area 22a, black for the area 22b, or black for the area 22a, red for the area 22b, but are not limited to them.

A method of putting the seal 22 at the position in the horizontal direction from the seal 22 put on the orbitale with high dimensional accuracy using the seal 22 shown in FIG. 68 will be explained.

Figure 69:
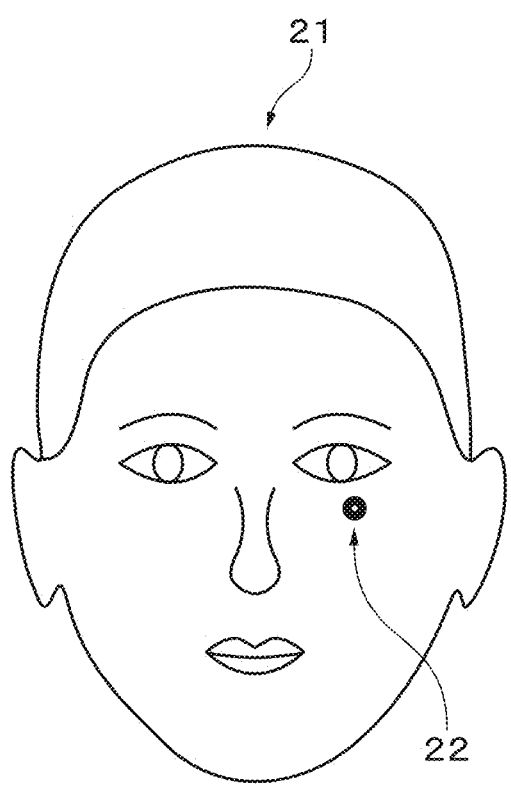
FIG. 69 A schematic drawing for explaining a method of putting a seal on the face of the head of a subject in the fourteenth embodiment of the present invention.

First, as shown in FIG. 69, by the method explained in the first embodiment, the seal 22 is put on the orbitale so that the center of the seal 22 coincides with the orbitale.

Figure 70:
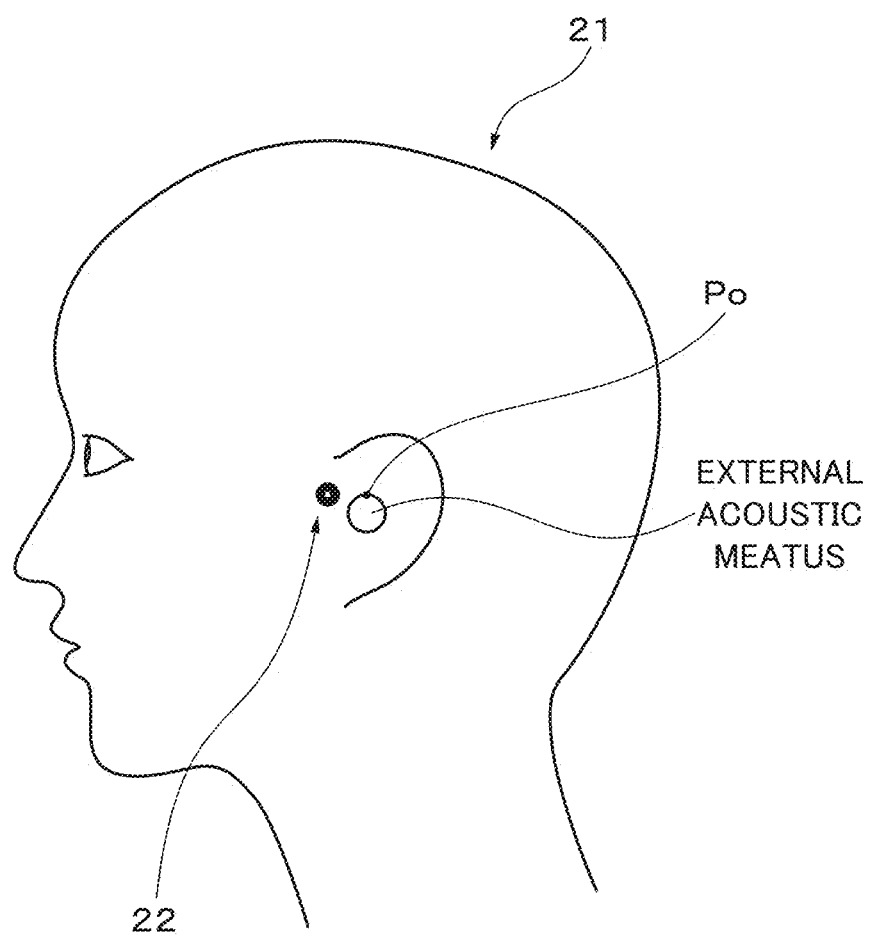
FIG. 70 A schematic drawing for explaining a method of putting a seal on the side surface of the head of a subject in the fourteenth embodiment of the present invention.

On the other hand, as shown in FIG. 70, the seal 22 is put on the position apart a small distance (for example, the position of 3 mm and more and 10 mm and less apart) in the horizontal direction of the face side from the porion.

Figure 71A:
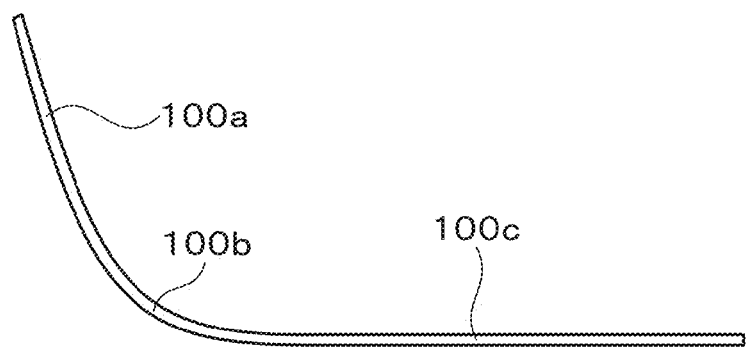
FIG. 71A A plan view showing a Frankfort plane indicator gauge to be used in the fourteenth embodiment of the present invention.
Figure 71B:
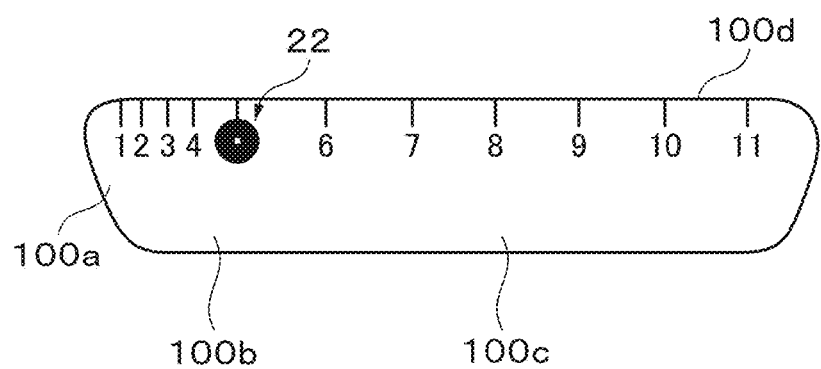
FIG. 71B A front view showing the Frankfort plane indicator gauge to be used in the fourteenth embodiment of the present invention.
Figure 71C:
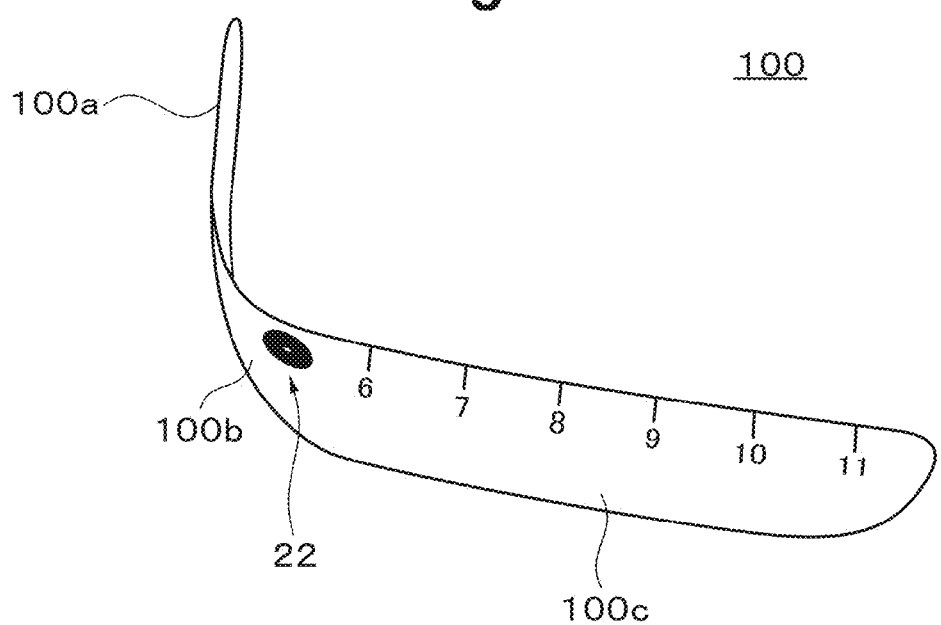
FIG. 71C A perspective view showing the Frankfort plane indicator gauge to be used in the fourteenth embodiment of the present invention.

Next, using a Frankfort plane indicator gauge 100 shown in FIG. 71A, FIG. 71B and FIG. 71C, the plane connecting the center of the seal 22 put on the orbitale with the center of the seal 22 put on a position a little apart from the porion is decided as follows. Here, FIG. 71A is the plan view, FIG. 71B is the front view, and FIG. 71C is the perspective view of the Frankfort plane indicator gauge 100. As shown in FIG. 71A, FIG. 71B and FIG. 71C, the Frankfort plane indicator gauge 100 has a curved shape so that a long and thin rectangular plate as a whole fits to the part from the part under the eyes of the face of the head 21 to ears, and consists of the nearly planar first part 100a, the curved second part 100b, and the nearly tabular third part 100c. The first part 100a is the part applying to the part of the face of the head 21 under the eyes, and the third part 100c is the part applying to the side surface of the head 21. The length of the first part 100a is shorter than the length of the third part 100c. According to the Frankfort plane indicator gauge 100, by applying force on the first part 100a and the third part 100c, making the first part 100a and the third part 100c rotate centered on the curved part 100b, the angle between the first part 100a and the third part 100c can be changed. The Frankfort plane indicator gauge 100 is formed by, for example, transparent plastic materials such as acrylic, PET, etc., but is not limited to them, and the materials to be used, and whether it is made transparent or opaque are selected as necessary. The upper edge surface 100d of the Frankfort plane indicator gauge 100 is, for example, colored in black. Also, on the upper side surface of the Frankfort plane indicator gauge 100, a scale (for example, a scale marked every mm) is marked, and the distance in the length direction of the Frankfort plane indicator gauge 100 can be measured. Giving a concrete example of the Frankfort plane indicator gauge 100, the material is acrylic, the length of the first part 100a is about 3 cm, the length of the third part 100c is about 7 cm, the length of the second part 100b is about 3 cm, the height is about 3 cm, and the thickness is about 1 mm. The size of the head 21 differs from adult or child, male or female, etc. Therefore, it is effective to prepare the plural kinds of Frankfort plane indicator gauge 100 with different sizes, select and use the size fit to the head 21 of a patient from them.

Figure 72:
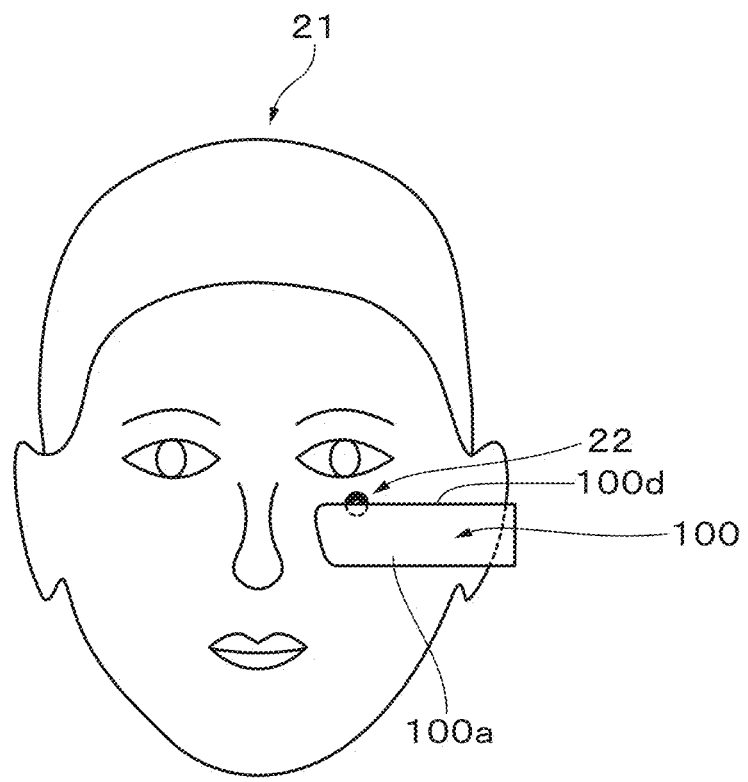
FIG. 72 A schematic drawing for explaining a method of putting a seal on the face of the head of a subject in the fourteenth embodiment of the present invention.
Figure 73:
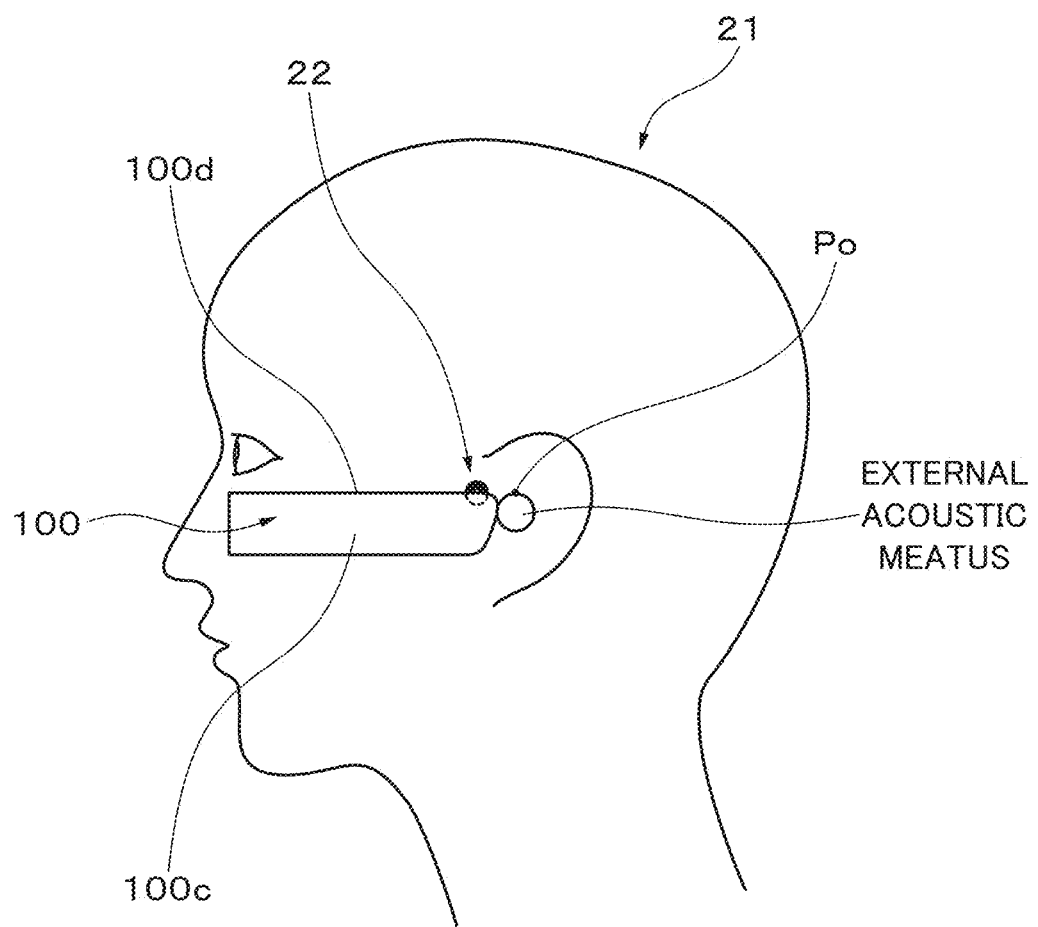
FIG. 73 A schematic drawing for explaining a method of putting a seal on the face of the head of a subject in the fourteenth embodiment of the present invention.

As shown in FIG. 72 and FIG. 73, the Frankfort plane indicator gauge 100 is lightly pushed to the face of the head 21 so that the first part 100a applies to the part under the eye of the face of the head 21, and the third part 100c applies to the side surface of the head 21. And the Frankfort plane indicator gauge 100 is positioned so that the upper edge surface 100d of the first part 100a coincides with the center of the area 22a of the seal 22 put on the orbitale, and the upper edge surface 100d of the third part 100c coincides with the center of the area 22a of the seal 22 put on near the porion.

Figure 74:
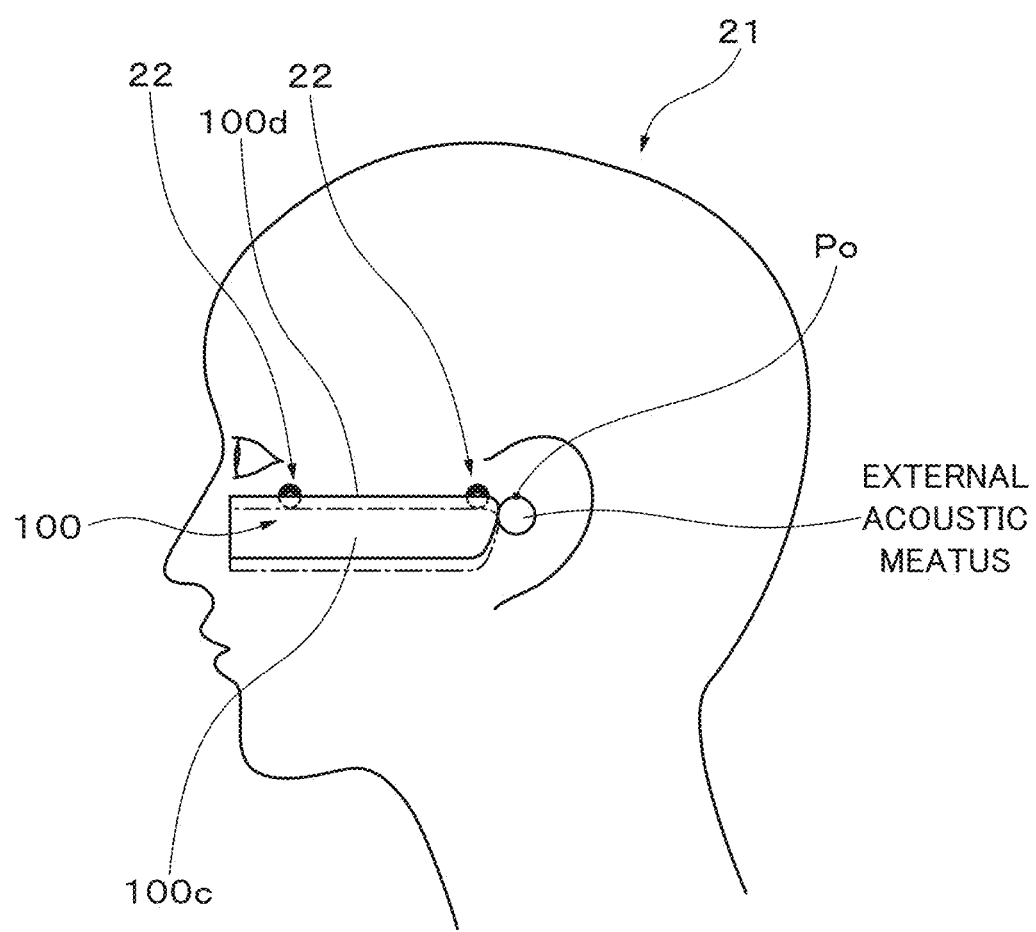
FIG. 74 A schematic drawing for explaining a method of putting a seal on the face of the head of a subject in the fourteenth embodiment of the present invention.

As shown in FIG. 74, with a care that the Frankfort plane indicator gauge 100 positioned as the above is not out of position, the third part 100c of the Frankfort plane indicator gauge 100 is slightly risen from the side surface of the head 21, so that a clearance is formed between the third part 100c and the face of the head 21. Then the seal 22 is inserted in the clearance and is put on the side surface of the head 21 so that the center of the area 22a of the seal 22 coincides with the upper edge surface 100d of the Frankfort plane indicator gauge 100. In this case, the seal 22 showing the position of putting the seal 22 may be put in advance at the side surface of the Frankfort plane indicator gauge 100 (FIG. 71B and FIG. 71C). By this, the seal 22 can be put on the position in the horizontal direction from the seal 22 put on the orbitale with high dimensional accuracy.

Or, as shown in FIG. 74 by a dot and dash line, it may be possible to position the Frankfort plane indicator gauge 100 so that the top edge surface 100d of the first part 100a coincides with the bottom edge of the seal 22 put on the orbitale and the top edge surface 100d of the third part 100c coincides with the bottom edge of the seal 22 put on near the porion, and to put the seal 22 on the side surface of the head 21 at the upper of the seal 22 put on the side surface of the Frankfort plane indicator gauge 100 in advance so that its bottom edge coincides with the upper edge surface 100d of the Frankfort plane indicator gauge 100. By this, the seal 22 can be put at the position in the horizontal direction from the seal 22 put on the orbitale with high dimensional accuracy.

According to the fourteenth embodiment, by using the seal 22 shown in FIG. 68 and the Frankfort plane indicator gauge 100 shown in FIG. 71A, FIG. 71B and FIG. 71C, the seal 22 can be put at the position in the horizontal direction from the seal 22 put on the orbitale with high dimensional accuracy.

Heretofore, embodiments and examples of the present invention have been explained specifically. However, the present invention is not limited to these embodiments and examples, but contemplates various changes and modifications based on the technical idea of the present invention.

For example, numerical numbers, configurations, materials, constitutions, procedures, etc. presented in the embodiments and examples are only examples, and the different numerical numbers, configurations, materials, constitutions, procedures, etc. may be used as necessary.

Moreover, the head tilt setting device may be, for example, a video camera taking the head of a subject from the lateral direction and a display (a liquid crystal display or an organic EL display) displaying the images taken by the video camera, and a protractor measuring the inclination angle to the horizontal line centered on the first reference point may be displayed on the display. In this case, the combination of the head tilt setting device with the horizontal plane verification mechanism can be used, and by doing so, the head tilt of a subject can be set.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

EXPLANATION OF REFERENCE NUMERALS

11 X-ray generator
11a X-ray tube
12, 13 Arm
12a, 13a Lower part
12b, 13b Upper part
14 Arm control device
15 X-ray detector
16 Reference line
17, 18 Ear rod
19 Head tilt setting device
20, 93 Horizontal plate
21 Head
22 Seal
51 Support Platform
52 Support bar
61 Support Platform
62 Support bar
63 Main part
64 Support member
71 Lower part of the arm tilt setting device
81 Foldable scale-like horizontal plate
82 Colored line
83 Optical device
84 X-ray shielding cover
85 Visible light beam
86, 87, 88 Support
91, 92, 94, 95 Mark
100 Frankfort plane indicator gauge

The invention claimed is:

1. An X-ray radiographic apparatus, comprising:
a pair of arms provided facing each other and connected to an arm control device,
ear rods respectively provided on inside surfaces facing each of the pair of arms,
a head tilt setting device for setting a tilt in a front-rear direction of a head of a subject which is provided at at least one of the pair of arms, having a transparent plate provided vertically to a central axis of the ear rods integrally with the arm, or provided vertically to the central axis of the ear rods on an exterior surface of the arm; and
a horizontal plane verification mechanism that recognizes a horizontal plane when setting the head tilt using the head tilt setting device.

2. The X-ray radiographic apparatus according to claim 1 wherein the head tilt setting device sets the head tilt so that a straight line connecting a first reference point on one of the arms or the ear rods with a second reference point on a face of the subject becomes a horizontal line or a straight line tilted at a predetermined angle to the horizontal line, when looking at the head from a lateral direction.

3. The X-ray radiographic apparatus according to claim 2 wherein the head tilt setting device has a function of a protractor measuring an inclination angle to the horizontal line centered on the first reference point.

4. The X-ray radiographic apparatus according to claim 1 wherein the horizontal plane verification mechanism comprises a horizontal plate provided protruding to an inside vertically to the transparent plate on the transparent plate, a pair of colored horizontal lines provided at a position of both surfaces facing each other of the transparent plate, a horizontal plate having a foldable scale-like constitution which is able to open and close in the horizontal plane provided on the transparent plate, an optical device which is able to irradiate or scan a visible light beam in the horizontal plane provided on the transparent plate, a horizontal colored line provided parallel to the transparent plate, a horizontal plate which is able to move up and down, or move in the horizontal plane provided outside of the transparent plate, a horizontal plate having a foldable scale-like constitution which is able to open and close in the horizontal plane provided outside of the transparent plate, an optical device which is able to irradiate or scan a visible light beam in the horizontal plane provided outside of the transparent plate, or a horizontal colored line provided parallel to the transparent plate outside of the transparent plate.

5. The X-ray radiographic apparatus according to claim 2, wherein the first reference point is an uppermost point of the ear rods.

6. The X-ray radiographic apparatus according to claim 2, wherein the second reference point is an orbitale, an orbital margin just under a center of a pupil or a center of a palpebral fissure of the subject.

7. The X-ray radiographic apparatus according to claim 1, wherein a scale showing a length made of X-ray shielding materials is provided on the transparent plate.

8. The X-ray radiographic apparatus according to claim 7, wherein the transparent plate is provided at one of the pair of arms, and another transparent plate provided with a scale showing a length made of X-ray shielding materials is provided on the other of the pair of arms.

9. The X-ray radiographic apparatus according to claim 1, wherein the X-ray radiographic apparatus is a cephalometric X-ray radiographic apparatus.

10. A method of measuring head tilt in taking a radiograph, comprising:
when taking a radiograph of a head of a subject, measuring a tilt in a front-rear direction of the head of the subject under a state that ear rods respectively provided on inside surfaces facing each of a pair of arms provided facing each other and connected to an arm control device are inserted in external acoustic openings of both ears of the subject,
using a head tilt setting device provided at at least one of the pair of arms for setting a straight line connecting a first reference point on one of the arms or the ear rods with a second reference point of a face of the subject to become a horizontal line or a straight line tilted at a predetermined angle to the horizontal line when looking at the head from a lateral direction, the head tilt setting device having a transparent plate provided vertically to a central axis of the ear rods integrally with the arm, or provided vertically to the central axis of the ear rods on an exterior surface of the arm; and
providing a horizontal plane verification mechanism that recognizes a horizontal plane when setting the head tilt using the head tilt setting device.

11. A stand for X-ray radiographic apparatus used when taking a radiograph of a head of a subject by an X-ray radiographic apparatus having a pair of arms provided facing each other and connected to an arm control device and ear rods respectively provided on inside surfaces facing each of the pair of arms, comprising:
a head tilt setting device for setting a tilt in a front-rear direction of the head of the subject under a state that the ear rods of the pair of arms are inserted in the external acoustic openings of both ears of the subject so that a straight line connecting a first reference point on one of the arms or the ear rods with a second reference point on a face of the subject becomes a horizontal line or a straight line tilted at a predetermined angle to the horizontal line when looking at the head from a lateral direction, having a transparent plate provided vertically to a central axis of the ear rods integrally with the arms, or provided vertically to the central axis of the ear rods on an exterior surface of the arm; and a horizontal plane verification mechanism that recognizes a horizontal plane when setting the head tilt using the head tilt setting device.

12. A chair for X-ray radiographic apparatus used when taking a radiograph of a head of a subject by an X-ray radiographic apparatus having a pair of arms provided facing each other and connected to an arm control device and ear rods respectively provided on inside surfaces facing each of the pair of arms, comprising:

a head tilt setting device for setting a tilt in a front-rear direction of the head of the subject under a state that the ear rods of the pair of arms are inserted in external acoustic openings of both ears of the subject so that a straight line connecting a first reference point on one of the arms or the ear rods with a second reference point on a face of the subject becomes a horizontal line or a straight line tilted at a predetermined angle to the horizontal line when looking at the head from a lateral direction, having a transparent plate provided vertically to a central axis of the ear rods integrally with the arm, or provided vertically to the central axis of the ear rods on an exterior surface of the arm; and a horizontal plane verification mechanism that recognizes a horizontal plane when setting the head tilt using the head tilt setting device.

13. A head tilt setting device to be provided at at least one of a pair of arms of an X-ray radiographic apparatus having the pair of arms provided facing each other and connected to an arm control device, and ear rods respectively provided on inside surfaces facing each of the pair of arms, used, when taking a radiograph of a head of a subject, to set a tilt in a front-rear direction of the head of the subject under a state that the ear rods of the pair of arms are inserted in external acoustic openings of both ears of the subject so that a straight line connecting a first reference point on one of the arms or the ear rods with a second reference point on a face of the subject becomes a horizontal line or a straight line tilted at a predetermined angle to the horizontal line when looking at the head from a lateral direction, comprising:

a transparent plate provided vertically to a central axis of the ear rods on an exterior surface of the arm, the transparent plate having a horizontal plane verification mechanism that recognizes a horizontal plane when setting the head tilt using the head tilt setting device, the head tilt setting device having a function of a protractor for measuring an inclination angle to the horizontal line centered on the first reference point.

* * * * *